US012703884B2

(12) United States Patent
Jiao et al.

(10) Patent No.: US 12,703,884 B2
(45) Date of Patent: Aug. 11, 2026

(54) METHOD FOR DETECTING THE MUTATION AND METHYLATION OF TUMOR-SPECIFIC GENES IN ctDNA

(71) Applicants: CANCER HOSPITAL, CHINESE ACADEMY OF MEDICAL SCIENCES, Beijing (CN); GENETRON HEALTH (BEIJING) CO, LTD, Beijing (CN)

(72) Inventors: Yuchen Jiao, Beijing (CN); Chunfeng Qu, Beijing (CN); Yuting Wang, Beijing (CN); Pei Wang, Beijing (CN); Kun Chen, Beijing (CN); Qianqian Song, Beijing (CN); Hui Liu, Beijing (CN); Jingjing Wang, Beijing (CN); Sizhen Wang, Beijing (CN)

(73) Assignees: CANCER HOSPITAL, CHINESE ACADEMY OF MEDICAL SCIENCES, Beijing (CN); GENETRON HEALTH (BEIJING) CO, LTD, Beijing (CN)

( * ) Notice: Subject to any disclaimer, the term of this patent is extended or adjusted under 35 U.S.C. 154(b) by 1155 days.

(21) Appl. No.: 17/768,891

(22) PCT Filed: Oct. 13, 2020

(86) PCT No.: PCT/CN2020/120560

§ 371 (c)(1),
(2) Date: Apr. 14, 2022

(87) PCT Pub. No.: WO2021/073490

PCT Pub. Date: Apr. 22, 2021

(65) Prior Publication Data

US 2023/0272475 A1 Aug. 31, 2023

(30) Foreign Application Priority Data

Oct. 16, 2019 (CN) ........................ 201910983038.8

(51) Int. Cl.

*C12Q 1/6886* (2018.01)
*C12N 15/10* (2006.01)
*C12Q 1/6844* (2018.01)
*C12Q 1/6869* (2018.01)

(52) U.S. Cl.

CPC ....... *C12Q 1/6886* (2013.01); *C12N 15/1065* (2013.01); *C12Q 1/6844* (2013.01); *C12Q 1/6869* (2013.01); *C12Q 2600/154* (2013.01); *C12Q 2600/156* (2013.01)

(58) Field of Classification Search

CPC ........... C12N 15/1034; C12N 15/1065; C12N 15/1093; C12Q 1/6806; C12Q 1/6844; C12Q 1/6869; C12Q 1/6886; C12Q 2600/118; C12Q 2600/154; C12Q 2600/156; C12Q 2525/191; C12Q 2525/301; C12Q 2525/155; C12Q 2525/30; C12Q 2531/107; C12Q 2537/143; C12Q 2521/301; C40B 40/06; C40B 50/00; C40B 50/06

See application file for complete search history.

(56) References Cited

U.S. PATENT DOCUMENTS

2016/0319345 A1* 11/2016 Gnerre .................. G16B 30/00

FOREIGN PATENT DOCUMENTS

| | | | | |
|---|---|---|---|---|
| CN | 102877136 A | 1/2013 | | |
| CN | 107223159 A | 9/2017 | | |
| CN | 107723352 A | 2/2018 | | |
| CN | 108103060 A | 6/2018 | | |
| CN | 109790198 A | 5/2019 | | |
| WO | WO-2018035125 A1 * | 2/2018 | .......... | C12Q 1/6876 |

OTHER PUBLICATIONS

Bonora et al. (PLS One, 2019, 14(4):e0214368) (Year: 2019).*

First Office Action is corresponding Chinese Application No. 201910983038.8; mailed Sep. 10, 2021; 17 pgs.

International Search Report issue in corresponding International Application No. PCT/CN2020/120560; mailed Jan. 18, 2021; 7 pgs.

Li, Qiaoling; "Detection of Rare Mutations Using Unique Barcode Combined Region Target Capture"; South China University of Technology, Master Thesis; Apr. 15, 2016; 68 pgs. (Eng. Abstract provided).

* cited by examiner

*Primary Examiner* — Jeremy C Flinders

(74) *Attorney, Agent, or Firm* — HAUPTMAN HAM, LLP

(57) ABSTRACT

The present invention discloses a method for detecting the mutation and methylation of tumor-specific genes in ctDNA, and this method can simultaneously detect the mutation (including point mutation, insertion-deletion mutation, HBV integration and other mutation forms) and/or methylation of tumor-specific genes in ctDNA in one sample. Not only the sample size requirement is low, but the MC library prepared by this method can support 10-20 subsequent detections. The results of each test can represent the mutation status of all the original ctDNA specimens and the methylation modification status of the region covered by the restriction sites, without reducing the sensitivity and specificity. The present invention has important clinical significance for early tumor screening, disease tracking, efficacy evaluation, prognosis prediction and the like, and has great application value.

9 Claims, 2 Drawing Sheets

Specification includes a Sequence Listing.

SEQUENCE LISTING

<160> NUMBER OF SEQ ID NOS: 429

<210> SEQ ID NO 1
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 1
gacacgacgc tcttccgatc tnnnnnnnnc cactagtagc ct 42

<210> SEQ ID NO 2
<211> LENGTH: 41
<212> TYPE: DNA
<213> ORGANISM: Artificial sequence
<220> FEATURE:
<223> OTHER INFORMATION: Synthesized

<400> SEQUENCE: 2
ggctactagt ggctgtctct tatacacatc tccgagccca c 41

```
<210> SEQ ID NO 3
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 3

gacacgacgc tcttccgatc tnnnnnnnng gactgtgtcg gt                         42


<210> SEQ ID NO 4
<211> LENGTH: 41
<212> TYPE: DNA
<213> ORGANISM: Artificial sequence
<220> FEATURE:
<223> OTHER INFORMATION: Synthesized

<400> SEQUENCE: 4

ccgacacagt ccctgtctct tatacacatc tccgagccca c                          41


<210> SEQ ID NO 5
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 5

gacacgacgc tcttccgatc tnnnnnnnng gtactgacag gt                         42


<210> SEQ ID NO 6
<211> LENGTH: 41
<212> TYPE: DNA
<213> ORGANISM: Artificial sequence
<220> FEATURE:
<223> OTHER INFORMATION: Synthesized

<400> SEQUENCE: 6

cctgtcagta ccctgtctct tatacacatc tccgagccca c                          41


<210> SEQ ID NO 7
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 7

gacacgacgc tcttccgatc tnnnnnnnnc ctagtacagc ct                         42


<210> SEQ ID NO 8
<211> LENGTH: 41
<212> TYPE: DNA
<213> ORGANISM: Artificial sequence
<220> FEATURE:
<223> OTHER INFORMATION: Synthesized
```

<400> SEQUENCE: 8
ggctgtacta ggctgtctct tatacacatc tccgagccca c 41

<210> SEQ ID NO 9
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 9
gacacgacgc tcttccgatc tnnnnnnnng gtagtcagag gt 42

<210> SEQ ID NO 10
<211> LENGTH: 41
<212> TYPE: DNA
<213> ORGANISM: Artificial sequence
<220> FEATURE:
<223> OTHER INFORMATION: Synthesized

<400> SEQUENCE: 10
cctctgacta ccctgtctct tatacacatc tccgagccca c 41

<210> SEQ ID NO 11
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 11
gacacgacgc tcttccgatc tnnnnnnnnt tctcacgtgt tt 42

<210> SEQ ID NO 12
<211> LENGTH: 41
<212> TYPE: DNA
<213> ORGANISM: Artificial sequence
<220> FEATURE:
<223> OTHER INFORMATION: Synthesized

<400> SEQUENCE: 12
aacacgtgag aactgtctct tatacacatc tccgagccca c 41

<210> SEQ ID NO 13
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 13
gacacgacgc tcttccgatc tnnnnnnnna actccacgta at 42

<210> SEQ ID NO 14
<211> LENGTH: 41

<212> TYPE: DNA
<213> ORGANISM: Artificial sequence
<220> FEATURE:
<223> OTHER INFORMATION: Synthesized

<400> SEQUENCE: 14
ttacgtggag ttctgtctct tatacacatc tccgagccca c 41

<210> SEQ ID NO 15
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 15
gacacgacgc tcttccgatc tnnnnnnnnt tctcgagaat tt 42

<210> SEQ ID NO 16
<211> LENGTH: 41
<212> TYPE: DNA
<213> ORGANISM: Artificial sequence
<220> FEATURE:
<223> OTHER INFORMATION: Synthesized

<400> SEQUENCE: 16
aattctcgag aactgtctct tatacacatc tccgagccca c 41

<210> SEQ ID NO 17
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 17
gacacgacgc tcttccgatc tnnnnnnnna aactcttcca at 42

<210> SEQ ID NO 18
<211> LENGTH: 41
<212> TYPE: DNA
<213> ORGANISM: Artificial sequence
<220> FEATURE:
<223> OTHER INFORMATION: Synthesized

<400> SEQUENCE: 18
ttggaagagt ttctgtctct tatacacatc tccgagccca c 41

<210> SEQ ID NO 19
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 19
gacacgacgc tcttccgatc tnnnnnnnnt tggaacgtct tt 42

<210> SEQ ID NO 20
<211> LENGTH: 41
<212> TYPE: DNA
<213> ORGANISM: Artificial sequence
<220> FEATURE:
<223> OTHER INFORMATION: Synthesized

<400> SEQUENCE: 20
aagacgttcc aactgtctct tatacacatc tccgagccca c 41

<210> SEQ ID NO 21
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 21
gacacgacgc tcttccgatc tnnnnnnnnc cggactcctc ct 42

<210> SEQ ID NO 22
<211> LENGTH: 41
<212> TYPE: DNA
<213> ORGANISM: Artificial sequence
<220> FEATURE:
<223> OTHER INFORMATION: Synthesized

<400> SEQUENCE: 22
ggaggagtcc ggctgtctct tatacacatc tccgagccca c 41

<210> SEQ ID NO 23
<211> LENGTH: 42
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (22)..(29)
<223> OTHER INFORMATION: n is a, c, g, or t

<400> SEQUENCE: 23
gacacgacgc tcttccgatc tnnnnnnnna aggaggagta at 42

<210> SEQ ID NO 24
<211> LENGTH: 41
<212> TYPE: DNA
<213> ORGANISM: Artificial sequence
<220> FEATURE:
<223> OTHER INFORMATION: Synthesized

<400> SEQUENCE: 24
ttactcctcc ttctgtctct tatacacatc tccgagccca c 41

<210> SEQ ID NO 25
<211> LENGTH: 19
<212> TYPE: DNA
<213> ORGANISM: Artificial sequence
<220> FEATURE:
<223> OTHER INFORMATION: Synthesized

<400> SEQUENCE: 25
gacacgacgc tcttccgat 19

<210> SEQ ID NO 26
<211> LENGTH: 22
<212> TYPE: DNA
<213> ORGANISM: Artificial sequence
<220> FEATURE:
<223> OTHER INFORMATION: Synthesized

<400> SEQUENCE: 26
gtgggctcgg agatgtgtat aa 22

<210> SEQ ID NO 27
<211> LENGTH: 27
<212> TYPE: DNA
<213> ORGANISM: Artificial sequence
<220> FEATURE:
<223> OTHER INFORMATION: Synthesized

<400> SEQUENCE: 27
tctttcccta cacgacgctc ttccgat 27

<210> SEQ ID NO 28
<211> LENGTH: 20
<212> TYPE: DNA
<213> ORGANISM: Artificial sequence
<220> FEATURE:
<223> OTHER INFORMATION: Synthesized

<400> SEQUENCE: 28
tgtattaggg tgcagcgctc 20

<210> SEQ ID NO 29
<211> LENGTH: 18
<212> TYPE: DNA
<213> ORGANISM: Artificial sequence
<220> FEATURE:
<223> OTHER INFORMATION: Synthesized

<400> SEQUENCE: 29
cgctcggatc tggacctg 18

<210> SEQ ID NO 30
<211> LENGTH: 19
<212> TYPE: DNA
<213> ORGANISM: Artificial sequence
<220> FEATURE:
<223> OTHER INFORMATION: Synthesized

<400> SEQUENCE: 30
tggagccctg tgactcgaa 19

<210> SEQ ID NO 31
<211> LENGTH: 21
<212> TYPE: DNA
<213> ORGANISM: Artificial sequence
<220> FEATURE:
<223> OTHER INFORMATION: Synthesized

<400> SEQUENCE: 31
gtgaccagga catggatgag g 21

<210> SEQ ID NO 32
<211> LENGTH: 21
<212> TYPE: DNA

<213> ORGANISM: Artificial sequence
<220> FEATURE:
<223> OTHER INFORMATION: Synthesized

<400> SEQUENCE: 32
tcctccagta gacggtacag c 21

<210> SEQ ID NO 33
<211> LENGTH: 18
<212> TYPE: DNA
<213> ORGANISM: Artificial sequence
<220> FEATURE:
<223> OTHER INFORMATION: Synthesized

<400> SEQUENCE: 33
tgctgcttgt ccccacac 18

<210> SEQ ID NO 34
<211> LENGTH: 18
<212> TYPE: DNA
<213> ORGANISM: Artificial sequence
<220> FEATURE:
<223> OTHER INFORMATION: Synthesized

<400> SEQUENCE: 34
ccgcttggca ccacttcc 18

<210> SEQ ID NO 35
<211> LENGTH: 18
<212> TYPE: DNA
<213> ORGANISM: Artificial sequence
<220> FEATURE:
<223> OTHER INFORMATION: Synthesized

<400> SEQUENCE: 35
ggcacgggaa gcacgtac 18

<210> SEQ ID NO 36
<211> LENGTH: 18
<212> TYPE: DNA
<213> ORGANISM: Artificial sequence
<220> FEATURE:
<223> OTHER INFORMATION: Synthesized

<400> SEQUENCE: 36
ccttgcagtg ggaaggtg 18

<210> SEQ ID NO 37
<211> LENGTH: 23
<212> TYPE: DNA
<213> ORGANISM: Artificial sequence
<220> FEATURE:
<223> OTHER INFORMATION: Synthesized

<400> SEQUENCE: 37
gacagaaaag cggctgttag tca 23

<210> SEQ ID NO 38
<211> LENGTH: 19
<212> TYPE: DNA
<213> ORGANISM: Artificial sequence
<220> FEATURE:
<223> OTHER INFORMATION: Synthesized

<400> SEQUENCE: 38
ccgacctcag ctacagcat 19

<210> SEQ ID NO 39
<211> LENGTH: 21
<212> TYPE: DNA
<213> ORGANISM: Artificial sequence
<220> FEATURE:
<223> OTHER INFORMATION: Synthesized

<400> SEQUENCE: 39
acttgagcaa cccggagtct g 21

<210> SEQ ID NO 40
<211> LENGTH: 20
<212> TYPE: DNA
<213> ORGANISM: Artificial sequence
<220> FEATURE:
<223> OTHER INFORMATION: Synthesized

<400> SEQUENCE: 40
ctcctagctc tgcagtccga 20

<210> SEQ ID NO 41
<211> LENGTH: 18
<212> TYPE: DNA
<213> ORGANISM: Artificial sequence
<220> FEATURE:
<223> OTHER INFORMATION: Synthesized

<400> SEQUENCE: 41
gcgcctggct ccatttcc 18

<210> SEQ ID NO 42
<211> LENGTH: 21
<212> TYPE: DNA
<213> ORGANISM: Artificial sequence
<220> FEATURE:
<223> OTHER INFORMATION: Synthesized

<400> SEQUENCE: 42
cgcctgagaa cctgcaaaga g 21

<210> SEQ ID NO 43
<211> LENGTH: 18
<212> TYPE: DNA
<213> ORGANISM: Artificial sequence
<220> FEATURE:
<223> OTHER INFORMATION: Synthesized

<400> SEQUENCE: 43
gtccagggag caatgcgt 18

<210> SEQ ID NO 44
<211> LENGTH: 19
<212> TYPE: DNA
<213> ORGANISM: Artificial sequence
<220> FEATURE:
<223> OTHER INFORMATION: Synthesized

<400> SEQUENCE: 44
cgggttaccc cacagccta 19

<210> SEQ ID NO 45
<211> LENGTH: 18
<212> TYPE: DNA
<213> ORGANISM: Artificial sequence
<220> FEATURE:

<223> OTHER INFORMATION: Synthesized

<400> SEQUENCE: 45
ggctcccagt ggattcgc 18

<210> SEQ ID NO 46
<211> LENGTH: 18
<212> TYPE: DNA
<213> ORGANISM: Artificial sequence
<220> FEATURE:
<223> OTHER INFORMATION: Synthesized

<400> SEQUENCE: 46
gtcctgcccc ttcacctt 18

<210> SEQ ID NO 47
<211> LENGTH: 22
<212> TYPE: DNA
<213> ORGANISM: Artificial sequence
<220> FEATURE:
<223> OTHER INFORMATION: Synthesized

<400> SEQUENCE: 47
ccgactactg cctcacccat at 22

<210> SEQ ID NO 48
<211> LENGTH: 26
<212> TYPE: DNA
<213> ORGANISM: Artificial sequence
<220> FEATURE:
<223> OTHER INFORMATION: Synthesized

<400> SEQUENCE: 48
gggtttttct tgttgacaag aatcct 26

<210> SEQ ID NO 49
<211> LENGTH: 22
<212> TYPE: DNA
<213> ORGANISM: Artificial sequence
<220> FEATURE:
<223> OTHER INFORMATION: Synthesized

<400> SEQUENCE: 49
ccaacctcca atcactcacc aa 22

<210> SEQ ID NO 50
<211> LENGTH: 28
<212> TYPE: DNA
<213> ORGANISM: Artificial sequence
<220> FEATURE:
<223> OTHER INFORMATION: Synthesized

<400> SEQUENCE: 50
ggcgttttat catattcctc ttcatcct 28

<210> SEQ ID NO 51
<211> LENGTH: 26
<212> TYPE: DNA
<213> ORGANISM: Artificial sequence
<220> FEATURE:
<223> OTHER INFORMATION: Synthesized

<400> SEQUENCE: 51
ctacttccag gaacatcaac taccag 26

<210> SEQ ID NO 52
<211> LENGTH: 23
<212> TYPE: DNA
<213> ORGANISM: Artificial sequence
<220> FEATURE:
<223> OTHER INFORMATION: Synthesized

<400> SEQUENCE: 52
ctgcacttgt attcccatcc cat 23

<210> SEQ ID NO 53
<211> LENGTH: 27
<212> TYPE: DNA
<213> ORGANISM: Artificial sequence
<220> FEATURE:
<223> OTHER INFORMATION: Synthesized

<400> SEQUENCE: 53
tcagtttact agtgccattt gttcagt 27

<210> SEQ ID NO 54
<211> LENGTH: 28
<212> TYPE: DNA
<213> ORGANISM: Artificial sequence
<220> FEATURE:
<223> OTHER INFORMATION: Synthesized

<400> SEQUENCE: 54
tacaacatct tgagtccctt tttacctc 28

<210> SEQ ID NO 55
<211> LENGTH: 23
<212> TYPE: DNA
<213> ORGANISM: Artificial sequence
<220> FEATURE:
<223> OTHER INFORMATION: Synthesized

<400> SEQUENCE: 55
agaattgtgg gtcttttggg ctt 23

<210> SEQ ID NO 56
<211> LENGTH: 30
<212> TYPE: DNA
<213> ORGANISM: Artificial sequence
<220> FEATURE:
<223> OTHER INFORMATION: Synthesized

<400> SEQUENCE: 56
tgtaaacaat atctgaacct ttaccctgtt 30

<210> SEQ ID NO 57
<211> LENGTH: 20
<212> TYPE: DNA
<213> ORGANISM: Artificial sequence
<220> FEATURE:
<223> OTHER INFORMATION: Synthesized

<400> SEQUENCE: 57
gcatgcgtgg aacctttgtg 20

<210> SEQ ID NO 58
<211> LENGTH: 23
<212> TYPE: DNA
<213> ORGANISM: Artificial sequence
<220> FEATURE:
<223> OTHER INFORMATION: Synthesized

<400> SEQUENCE: 58
aactctgttg tcctctctcg gaa 23

<210> SEQ ID NO 59
<211> LENGTH: 18
<212> TYPE: DNA
<213> ORGANISM: Artificial sequence
<220> FEATURE:
<223> OTHER INFORMATION: Synthesized

<400> SEQUENCE: 59
ctgaatcccg cggacgac 18

<210> SEQ ID NO 60
<211> LENGTH: 21
<212> TYPE: DNA
<213> ORGANISM: Artificial sequence
<220> FEATURE:
<223> OTHER INFORMATION: Synthesized

<400> SEQUENCE: 60
ccgtctgtgc cttctcatct g 21

<210> SEQ ID NO 61
<211> LENGTH: 19
<212> TYPE: DNA
<213> ORGANISM: Artificial sequence
<220> FEATURE:
<223> OTHER INFORMATION: Synthesized

<400> SEQUENCE: 61
gaacgcccac caggtcttg 19

<210> SEQ ID NO 62
<211> LENGTH: 24
<212> TYPE: DNA
<213> ORGANISM: Artificial sequence
<220> FEATURE:
<223> OTHER INFORMATION: Synthesized

<400> SEQUENCE: 62
ccttgaggcg tacttcaaag actg 24

<210> SEQ ID NO 63
<211> LENGTH: 23
<212> TYPE: DNA
<213> ORGANISM: Artificial sequence
<220> FEATURE:
<223> OTHER INFORMATION: Synthesized

<400> SEQUENCE: 63
ggaggctgta ggcataaatt ggt 23

<210> SEQ ID NO 64
<211> LENGTH: 22
<212> TYPE: DNA
<213> ORGANISM: Artificial sequence
<220> FEATURE:
<223> OTHER INFORMATION: Synthesized

<400> SEQUENCE: 64
gtcctactgt tcaagcctcc aa 22

<210> SEQ ID NO 65
<211> LENGTH: 22

<212> TYPE: DNA
<213> ORGANISM: Artificial sequence
<220> FEATURE:
<223> OTHER INFORMATION: Synthesized

<400> SEQUENCE: 65
gggcttctgt ggagttactc tc 22

<210> SEQ ID NO 66
<211> LENGTH: 22
<212> TYPE: DNA
<213> ORGANISM: Artificial sequence
<220> FEATURE:
<223> OTHER INFORMATION: Synthesized

<400> SEQUENCE: 66
ttgtatcggg aggccttaga gt 22

<210> SEQ ID NO 67
<211> LENGTH: 21
<212> TYPE: DNA
<213> ORGANISM: Artificial sequence
<220> FEATURE:
<223> OTHER INFORMATION: Synthesized

<400> SEQUENCE: 67
ttctgtgttg gggtgagttg a 21

<210> SEQ ID NO 68
<211> LENGTH: 25
<212> TYPE: DNA
<213> ORGANISM: Artificial sequence
<220> FEATURE:
<223> OTHER INFORMATION: Synthesized

<400> SEQUENCE: 68
ccagcatcca gggaattagt agtca 25

<210> SEQ ID NO 69
<211> LENGTH: 27
<212> TYPE: DNA
<213> ORGANISM: Artificial sequence
<220> FEATURE:
<223> OTHER INFORMATION: Synthesized

<400> SEQUENCE: 69
ttcctgtctt acctttggaa gagaaac 27

<210> SEQ ID NO 70
<211> LENGTH: 25
<212> TYPE: DNA
<213> ORGANISM: Artificial sequence
<220> FEATURE:
<223> OTHER INFORMATION: Synthesized

<400> SEQUENCE: 70
ccggaaacta ctgttgttag acgta 25

<210> SEQ ID NO 71
<211> LENGTH: 23
<212> TYPE: DNA
<213> ORGANISM: Artificial sequence
<220> FEATURE:
<223> OTHER INFORMATION: Synthesized

<400> SEQUENCE: 71
cgtcgcagaa gatctcaatc tcg 23

<210> SEQ ID NO 72
<211> LENGTH: 28
<212> TYPE: DNA
<213> ORGANISM: Artificial sequence
<220> FEATURE:
<223> OTHER INFORMATION: Synthesized

<400> SEQUENCE: 72
aaactccctc ctttcctaac attcattt 28

<210> SEQ ID NO 73
<211> LENGTH: 26
<212> TYPE: DNA
<213> ORGANISM: Artificial sequence
<220> FEATURE:
<223> OTHER INFORMATION: Synthesized

<400> SEQUENCE: 73
tatgcctgct aggttctatc ctaacc 26

<210> SEQ ID NO 74
<211> LENGTH: 27
<212> TYPE: DNA
<213> ORGANISM: Artificial sequence
<220> FEATURE:
<223> OTHER INFORMATION: Synthesized

<400> SEQUENCE: 74
ggcattattt acatactctg tggaagg 27

<210> SEQ ID NO 75
<211> LENGTH: 22
<212> TYPE: DNA
<213> ORGANISM: Artificial sequence
<220> FEATURE:
<223> OTHER INFORMATION: Synthesized

<400> SEQUENCE: 75
gttggtcttc caaacctcga ca 22

<210> SEQ ID NO 76
<211> LENGTH: 22
<212> TYPE: DNA
<213> ORGANISM: Artificial sequence
<220> FEATURE:
<223> OTHER INFORMATION: Synthesized

<400> SEQUENCE: 76
ttcaacccca acaaggatca ct 22

<210> SEQ ID NO 77
<211> LENGTH: 20
<212> TYPE: DNA
<213> ORGANISM: Artificial sequence
<220> FEATURE:
<223> OTHER INFORMATION: Synthesized

<400> SEQUENCE: 77
ttccaccaat cggcagtcag 20

<210> SEQ ID NO 78
<211> LENGTH: 21
<212> TYPE: DNA
<213> ORGANISM: Artificial sequence
<220> FEATURE:
<223> OTHER INFORMATION: Synthesized

<400> SEQUENCE: 78
gccctgctca gaatactgtc t 21

<210> SEQ ID NO 79
<211> LENGTH: 20
<212> TYPE: DNA
<213> ORGANISM: Artificial sequence
<220> FEATURE:
<223> OTHER INFORMATION: Synthesized

<400> SEQUENCE: 79
attcgcagtc ccaaatctcc 20

<210> SEQ ID NO 80
<211> LENGTH: 21
<212> TYPE: DNA
<213> ORGANISM: Artificial sequence
<220> FEATURE:
<223> OTHER INFORMATION: Synthesized

<400> SEQUENCE: 80
catcttcctc tgcatcctgc t 21

<210> SEQ ID NO 81
<211> LENGTH: 22
<212> TYPE: DNA
<213> ORGANISM: Artificial sequence
<220> FEATURE:
<223> OTHER INFORMATION: Synthesized

<400> SEQUENCE: 81
ttccaggatc atcaaccacc ag 22

<210> SEQ ID NO 82
<211> LENGTH: 18
<212> TYPE: DNA
<213> ORGANISM: Artificial sequence
<220> FEATURE:
<223> OTHER INFORMATION: Synthesized

<400> SEQUENCE: 82
gtccctttat gccgctgt 18

<210> SEQ ID NO 83
<211> LENGTH: 29
<212> TYPE: DNA
<213> ORGANISM: Artificial sequence
<220> FEATURE:
<223> OTHER INFORMATION: Synthesized

<400> SEQUENCE: 83
acccttataa agaatttgga gctactgtg 29

<210> SEQ ID NO 84
<211> LENGTH: 22
<212> TYPE: DNA
<213> ORGANISM: Artificial sequence
<220> FEATURE:
<223> OTHER INFORMATION: Synthesized

<400> SEQUENCE: 84
ctcctgaaca ttgctcacct ca 22

<210> SEQ ID NO 85
<211> LENGTH: 18
<212> TYPE: DNA
<213> ORGANISM: Artificial sequence
<220> FEATURE:
<223> OTHER INFORMATION: Synthesized

<400> SEQUENCE: 85
agactgcctt ccgggtca 18

<210> SEQ ID NO 86
<211> LENGTH: 22
<212> TYPE: DNA
<213> ORGANISM: Artificial sequence
<220> FEATURE:
<223> OTHER INFORMATION: Synthesized

<400> SEQUENCE: 86
cctgtgggaa gcgaaaattc ca 22

<210> SEQ ID NO 87
<211> LENGTH: 19
<212> TYPE: DNA
<213> ORGANISM: Artificial sequence
<220> FEATURE:
<223> OTHER INFORMATION: Synthesized

<400> SEQUENCE: 87
acctggtcct ctgactgct 19

<210> SEQ ID NO 88
<211> LENGTH: 24
<212> TYPE: DNA
<213> ORGANISM: Artificial sequence
<220> FEATURE:
<223> OTHER INFORMATION: Synthesized

<400> SEQUENCE: 88
aagcaatgga tgatttgatg ctgt 24

<210> SEQ ID NO 89
<211> LENGTH: 20
<212> TYPE: DNA
<213> ORGANISM: Artificial sequence
<220> FEATURE:
<223> OTHER INFORMATION: Synthesized

<400> SEQUENCE: 89
gacccaggtc cagatgaagc 20

<210> SEQ ID NO 90
<211> LENGTH: 18
<212> TYPE: DNA
<213> ORGANISM: Artificial sequence
<220> FEATURE:
<223> OTHER INFORMATION: Synthesized

<400> SEQUENCE: 90
tcctggcccc tgtcatct 18

<210> SEQ ID NO 91
<211> LENGTH: 22
<212> TYPE: DNA
<213> ORGANISM: Artificial sequence
<220> FEATURE:
<223> OTHER INFORMATION: Synthesized

<400> SEQUENCE: 91
gtgccctgac tttcaactct gt 22

<210> SEQ ID NO 92
<211> LENGTH: 18
<212> TYPE: DNA
<213> ORGANISM: Artificial sequence
<220> FEATURE:
<223> OTHER INFORMATION: Synthesized

<400> SEQUENCE: 92
caactggcca agacctgc 18

<210> SEQ ID NO 93
<211> LENGTH: 20
<212> TYPE: DNA
<213> ORGANISM: Artificial sequence
<220> FEATURE:
<223> OTHER INFORMATION: Synthesized

<400> SEQUENCE: 93
cgccatggcc atctacaagc 20

<210> SEQ ID NO 94
<211> LENGTH: 18
<212> TYPE: DNA
<213> ORGANISM: Artificial sequence
<220> FEATURE:
<223> OTHER INFORMATION: Synthesized

<400> SEQUENCE: 94
ggtccccagg cctctgat 18

<210> SEQ ID NO 95
<211> LENGTH: 22
<212> TYPE: DNA
<213> ORGANISM: Artificial sequence
<220> FEATURE:
<223> OTHER INFORMATION: Synthesized

<400> SEQUENCE: 95
gagtggaagg aaatttgcgt gt 22

<210> SEQ ID NO 96
<211> LENGTH: 19
<212> TYPE: DNA
<213> ORGANISM: Artificial sequence
<220> FEATURE:
<223> OTHER INFORMATION: Synthesized

<400> SEQUENCE: 96
gcactggcct catcttggg 19

<210> SEQ ID NO 97
<211> LENGTH: 26
<212> TYPE: DNA
<213> ORGANISM: Artificial sequence
<220> FEATURE:
<223> OTHER INFORMATION: Synthesized

<400> SEQUENCE: 97
ccatccacta caactacatg tgtaac 26

<210> SEQ ID NO 98

<211> LENGTH: 24
<212> TYPE: DNA
<213> ORGANISM: Artificial sequence
<220> FEATURE:
<223> OTHER INFORMATION: Synthesized

<400> SEQUENCE: 98
tttccttact gcctcttgct tctc 24

<210> SEQ ID NO 99
<211> LENGTH: 20
<212> TYPE: DNA
<213> ORGANISM: Artificial sequence
<220> FEATURE:
<223> OTHER INFORMATION: Synthesized

<400> SEQUENCE: 99
gggacggaac agctttgagg 20

<210> SEQ ID NO 100
<211> LENGTH: 23
<212> TYPE: DNA
<213> ORGANISM: Artificial sequence
<220> FEATURE:
<223> OTHER INFORMATION: Synthesized

<400> SEQUENCE: 100
cacagaggaa gagaatctcc gca 23

<210> SEQ ID NO 101
<211> LENGTH: 26
<212> TYPE: DNA
<213> ORGANISM: Artificial sequence
<220> FEATURE:
<223> OTHER INFORMATION: Synthesized

<400> SEQUENCE: 101
tgcctcagat tcacttttat cacctt 26

<210> SEQ ID NO 102
<211> LENGTH: 30
<212> TYPE: DNA
<213> ORGANISM: Artificial sequence
<220> FEATURE:
<223> OTHER INFORMATION: Synthesized

<400> SEQUENCE: 102
ctcaggtact gtgtatatac ttacttctcc 30

<210> SEQ ID NO 103
<211> LENGTH: 19
<212> TYPE: DNA
<213> ORGANISM: Artificial sequence
<220> FEATURE:
<223> OTHER INFORMATION: Synthesized

<400> SEQUENCE: 103
cgtgagcgct tcgagatgt 19

<210> SEQ ID NO 104
<211> LENGTH: 22
<212> TYPE: DNA
<213> ORGANISM: Artificial sequence
<220> FEATURE:
<223> OTHER INFORMATION: Synthesized

<400> SEQUENCE: 104
gtgatgtcat ctctcctccc tg 22

<210> SEQ ID NO 105
<211> LENGTH: 25
<212> TYPE: DNA
<213> ORGANISM: Artificial sequence
<220> FEATURE:
<223> OTHER INFORMATION: Synthesized

<400> SEQUENCE: 105
tgaagtccaa aaagggtcag tctac 25

<210> SEQ ID NO 106
<211> LENGTH: 20
<212> TYPE: DNA
<213> ORGANISM: Artificial sequence
<220> FEATURE:
<223> OTHER INFORMATION: Synthesized

<400> SEQUENCE: 106
gggagcatct tcggtgaaac 20

<210> SEQ ID NO 107
<211> LENGTH: 22
<212> TYPE: DNA
<213> ORGANISM: Artificial sequence
<220> FEATURE:
<223> OTHER INFORMATION: Synthesized

<400> SEQUENCE: 107
caggcttatc ccatcttggt ca 22

<210> SEQ ID NO 108
<211> LENGTH: 18
<212> TYPE: DNA
<213> ORGANISM: Artificial sequence
<220> FEATURE:
<223> OTHER INFORMATION: Synthesized

<400> SEQUENCE: 108
ttggtggctg gcttggtc 18

<210> SEQ ID NO 109
<211> LENGTH: 21
<212> TYPE: DNA
<213> ORGANISM: Artificial sequence
<220> FEATURE:
<223> OTHER INFORMATION: Synthesized

<400> SEQUENCE: 109
gctgtaccgt ctactggagg a 21

<210> SEQ ID NO 110
<211> LENGTH: 21
<212> TYPE: DNA
<213> ORGANISM: Artificial sequence
<220> FEATURE:
<223> OTHER INFORMATION: Synthesized

<400> SEQUENCE: 110
gcttgttctc cagctctcgg a 21

<210> SEQ ID NO 111
<211> LENGTH: 18
<212> TYPE: DNA

<213> ORGANISM: Artificial sequence
<220> FEATURE:
<223> OTHER INFORMATION: Synthesized

<400> SEQUENCE: 111
gggaagtggt gccaagcg 18

<210> SEQ ID NO 112
<211> LENGTH: 18
<212> TYPE: DNA
<213> ORGANISM: Artificial sequence
<220> FEATURE:
<223> OTHER INFORMATION: Synthesized

<400> SEQUENCE: 112
gcacacgctg tacgtgct 18

<210> SEQ ID NO 113
<211> LENGTH: 18
<212> TYPE: DNA
<213> ORGANISM: Artificial sequence
<220> FEATURE:
<223> OTHER INFORMATION: Synthesized

<400> SEQUENCE: 113
gcctccacct gctccttg 18

<210> SEQ ID NO 114
<211> LENGTH: 22
<212> TYPE: DNA
<213> ORGANISM: Artificial sequence
<220> FEATURE:
<223> OTHER INFORMATION: Synthesized

<400> SEQUENCE: 114
ccctcaatga tccactgcat ga 22

<210> SEQ ID NO 115
<211> LENGTH: 24
<212> TYPE: DNA
<213> ORGANISM: Artificial sequence
<220> FEATURE:
<223> OTHER INFORMATION: Synthesized

<400> SEQUENCE: 115
ctcatacagg acttgggagg tatc 24

<210> SEQ ID NO 116
<211> LENGTH: 18
<212> TYPE: DNA
<213> ORGANISM: Artificial sequence
<220> FEATURE:
<223> OTHER INFORMATION: Synthesized

<400> SEQUENCE: 116
cacaaccgca ggacagct 18

<210> SEQ ID NO 117
<211> LENGTH: 18
<212> TYPE: DNA
<213> ORGANISM: Artificial sequence
<220> FEATURE:
<223> OTHER INFORMATION: Synthesized

<400> SEQUENCE: 117
ctccaagcct cggactgc 18

<210> SEQ ID NO 118
<211> LENGTH: 19
<212> TYPE: DNA
<213> ORGANISM: Artificial sequence
<220> FEATURE:
<223> OTHER INFORMATION: Synthesized

<400> SEQUENCE: 118
gcctcacacc agccacaac 19

<210> SEQ ID NO 119
<211> LENGTH: 20
<212> TYPE: DNA
<213> ORGANISM: Artificial sequence
<220> FEATURE:
<223> OTHER INFORMATION: Synthesized

<400> SEQUENCE: 119
tccccaccat gagcaaacca 20

<210> SEQ ID NO 120
<211> LENGTH: 18
<212> TYPE: DNA
<213> ORGANISM: Artificial sequence
<220> FEATURE:
<223> OTHER INFORMATION: Synthesized

<400> SEQUENCE: 120
gtgcctccct gcaacact 18

<210> SEQ ID NO 121
<211> LENGTH: 18
<212> TYPE: DNA
<213> ORGANISM: Artificial sequence
<220> FEATURE:
<223> OTHER INFORMATION: Synthesized

<400> SEQUENCE: 121
gcaccacgaa tgccggac 18

<210> SEQ ID NO 122
<211> LENGTH: 18
<212> TYPE: DNA
<213> ORGANISM: Artificial sequence
<220> FEATURE:
<223> OTHER INFORMATION: Synthesized

<400> SEQUENCE: 122
gtggggtaac ccgaggga 18

<210> SEQ ID NO 123
<211> LENGTH: 18
<212> TYPE: DNA
<213> ORGANISM: Artificial sequence
<220> FEATURE:
<223> OTHER INFORMATION: Synthesized

<400> SEQUENCE: 123
gaggaggcgg agctggaa 18

<210> SEQ ID NO 124
<211> LENGTH: 18
<212> TYPE: DNA
<213> ORGANISM: Artificial sequence
<220> FEATURE:

<223> OTHER INFORMATION: Synthesized

<400> SEQUENCE: 124
agcgctgcct gaaactcg 18

<210> SEQ ID NO 125
<211> LENGTH: 17
<212> TYPE: DNA
<213> ORGANISM: Artificial sequence
<220> FEATURE:
<223> OTHER INFORMATION: Synthesized

<400> SEQUENCE: 125
cgcacgaacg tggccag 17

<210> SEQ ID NO 126
<211> LENGTH: 19
<212> TYPE: DNA
<213> ORGANISM: Artificial sequence
<220> FEATURE:
<223> OTHER INFORMATION: Synthesized

<400> SEQUENCE: 126
gagccaccag caggaaagt 19

<210> SEQ ID NO 127
<211> LENGTH: 24
<212> TYPE: DNA
<213> ORGANISM: Artificial sequence
<220> FEATURE:
<223> OTHER INFORMATION: Synthesized

<400> SEQUENCE: 127
ctaggaatcc tgatgttgtg ctct 24

<210> SEQ ID NO 128
<211> LENGTH: 22
<212> TYPE: DNA
<213> ORGANISM: Artificial sequence
<220> FEATURE:
<223> OTHER INFORMATION: Synthesized

<400> SEQUENCE: 128
cgcgagtcta gactctgtgg ta 22

<210> SEQ ID NO 129
<211> LENGTH: 24
<212> TYPE: DNA
<213> ORGANISM: Artificial sequence
<220> FEATURE:
<223> OTHER INFORMATION: Synthesized

<400> SEQUENCE: 129
atagccagga caaattggag gaca 24

<210> SEQ ID NO 130
<211> LENGTH: 21
<212> TYPE: DNA
<213> ORGANISM: Artificial sequence
<220> FEATURE:
<223> OTHER INFORMATION: Synthesized

<400> SEQUENCE: 130
gacaaacggg caacatacct t 21

<210> SEQ ID NO 131
<211> LENGTH: 23
<212> TYPE: DNA
<213> ORGANISM: Artificial sequence
<220> FEATURE:
<223> OTHER INFORMATION: Synthesized

<400> SEQUENCE: 131
ccgaaggttt tgtacagcaa caa 23

<210> SEQ ID NO 132
<211> LENGTH: 23
<212> TYPE: DNA
<213> ORGANISM: Artificial sequence
<220> FEATURE:
<223> OTHER INFORMATION: Synthesized

<400> SEQUENCE: 132
ctgagccagg agaaacggac tga 23

<210> SEQ ID NO 133
<211> LENGTH: 26
<212> TYPE: DNA
<213> ORGANISM: Artificial sequence
<220> FEATURE:
<223> OTHER INFORMATION: Synthesized

<400> SEQUENCE: 133
gggactcaag atgttgtaca gacttg 26

<210> SEQ ID NO 134
<211> LENGTH: 21
<212> TYPE: DNA
<213> ORGANISM: Artificial sequence
<220> FEATURE:
<223> OTHER INFORMATION: Synthesized

<400> SEQUENCE: 134
gttaagggag tagccccaac g 21

<210> SEQ ID NO 135
<211> LENGTH: 25
<212> TYPE: DNA
<213> ORGANISM: Artificial sequence
<220> FEATURE:
<223> OTHER INFORMATION: Synthesized

<400> SEQUENCE: 135
caggcagttt tcgaaaacat tgctt 25

<210> SEQ ID NO 136
<211> LENGTH: 27
<212> TYPE: DNA
<213> ORGANISM: Artificial sequence
<220> FEATURE:
<223> OTHER INFORMATION: Synthesized

<400> SEQUENCE: 136
ttaaagcagg atagccacat tgtgtaa 27

<210> SEQ ID NO 137
<211> LENGTH: 25
<212> TYPE: DNA
<213> ORGANISM: Artificial sequence
<220> FEATURE:
<223> OTHER INFORMATION: Synthesized

<400> SEQUENCE: 137
ggcaacaggg taaaggttca gatat 25

<210> SEQ ID NO 138
<211> LENGTH: 19
<212> TYPE: DNA
<213> ORGANISM: Artificial sequence
<220> FEATURE:
<223> OTHER INFORMATION: Synthesized

<400> SEQUENCE: 138
ccacaaaggt tccacgcat 19

<210> SEQ ID NO 139
<211> LENGTH: 24
<212> TYPE: DNA
<213> ORGANISM: Artificial sequence
<220> FEATURE:
<223> OTHER INFORMATION: Synthesized

<400> SEQUENCE: 139
tggaaaggaa gtgtacttcc gaga 24

<210> SEQ ID NO 140
<211> LENGTH: 18
<212> TYPE: DNA
<213> ORGANISM: Artificial sequence
<220> FEATURE:
<223> OTHER INFORMATION: Synthesized

<400> SEQUENCE: 140
gtcgtccgcg ggattcag 18

<210> SEQ ID NO 141
<211> LENGTH: 18
<212> TYPE: DNA
<213> ORGANISM: Artificial sequence
<220> FEATURE:
<223> OTHER INFORMATION: Synthesized

<400> SEQUENCE: 141
aaggcacaga cggggaga 18

<210> SEQ ID NO 142
<211> LENGTH: 18
<212> TYPE: DNA
<213> ORGANISM: Artificial sequence
<220> FEATURE:
<223> OTHER INFORMATION: Synthesized

<400> SEQUENCE: 142
tcacggtggt ctccatgc 18

<210> SEQ ID NO 143
<211> LENGTH: 22
<212> TYPE: DNA
<213> ORGANISM: Artificial sequence
<220> FEATURE:
<223> OTHER INFORMATION: Synthesized

<400> SEQUENCE: 143
ggtcgttgac attgctgaga gt 22

<210> SEQ ID NO 144
<211> LENGTH: 22

<212> TYPE: DNA
<213> ORGANISM: Artificial sequence
<220> FEATURE:
<223> OTHER INFORMATION: Synthesized

<400> SEQUENCE: 144
aacctaatct cctcccccaa ct 22

<210> SEQ ID NO 145
<211> LENGTH: 23
<212> TYPE: DNA
<213> ORGANISM: Artificial sequence
<220> FEATURE:
<223> OTHER INFORMATION: Synthesized

<400> SEQUENCE: 145
gcagaggtga aaaagttgca tgg 23

<210> SEQ ID NO 146
<211> LENGTH: 18
<212> TYPE: DNA
<213> ORGANISM: Artificial sequence
<220> FEATURE:
<223> OTHER INFORMATION: Synthesized

<400> SEQUENCE: 146
ccacccaagg cacagctt 18

<210> SEQ ID NO 147
<211> LENGTH: 18
<212> TYPE: DNA
<213> ORGANISM: Artificial sequence
<220> FEATURE:
<223> OTHER INFORMATION: Synthesized

<400> SEQUENCE: 147
actccacaga agccccaa 18

<210> SEQ ID NO 148
<211> LENGTH: 20
<212> TYPE: DNA
<213> ORGANISM: Artificial sequence
<220> FEATURE:
<223> OTHER INFORMATION: Synthesized

<400> SEQUENCE: 148
gcctcccgat acaaagcaga 20

<210> SEQ ID NO 149
<211> LENGTH: 24
<212> TYPE: DNA
<213> ORGANISM: Artificial sequence
<220> FEATURE:
<223> OTHER INFORMATION: Synthesized

<400> SEQUENCE: 149
gattcatcaa ctcaccccaa caca 24

<210> SEQ ID NO 150
<211> LENGTH: 27
<212> TYPE: DNA
<213> ORGANISM: Artificial sequence
<220> FEATURE:
<223> OTHER INFORMATION: Synthesized

<400> SEQUENCE: 150
acatagctga ctactaattc cctggat 27

<210> SEQ ID NO 151
<211> LENGTH: 25
<212> TYPE: DNA
<213> ORGANISM: Artificial sequence
<220> FEATURE:
<223> OTHER INFORMATION: Synthesized

<400> SEQUENCE: 151
atccacactc caaaagacac caaat 25

<210> SEQ ID NO 152
<211> LENGTH: 22
<212> TYPE: DNA
<213> ORGANISM: Artificial sequence
<220> FEATURE:
<223> OTHER INFORMATION: Synthesized

<400> SEQUENCE: 152
gcgagggagt tcttcttcta gg 22

<210> SEQ ID NO 153
<211> LENGTH: 25
<212> TYPE: DNA
<213> ORGANISM: Artificial sequence
<220> FEATURE:
<223> OTHER INFORMATION: Synthesized

<400> SEQUENCE: 153
cagtaaagtt tcccaccttg tgagt 25

<210> SEQ ID NO 154
<211> LENGTH: 27
<212> TYPE: DNA
<213> ORGANISM: Artificial sequence
<220> FEATURE:
<223> OTHER INFORMATION: Synthesized

<400> SEQUENCE: 154
cctcctgtaa atgaatgtta ggaaagg 27

<210> SEQ ID NO 155
<211> LENGTH: 26
<212> TYPE: DNA
<213> ORGANISM: Artificial sequence
<220> FEATURE:
<223> OTHER INFORMATION: Synthesized

<400> SEQUENCE: 155
gtttaatgcc tttatccaag ggcaaa 26

<210> SEQ ID NO 156
<211> LENGTH: 27
<212> TYPE: DNA
<213> ORGANISM: Artificial sequence
<220> FEATURE:
<223> OTHER INFORMATION: Synthesized

<400> SEQUENCE: 156
ctcttatata gaatcccagc cttccac 27

<210> SEQ ID NO 157
<211> LENGTH: 22
<212> TYPE: DNA
<213> ORGANISM: Artificial sequence
<220> FEATURE:
<223> OTHER INFORMATION: Synthesized

<400> SEQUENCE: 157
cttgtcgagg tttggaagac ca 22

<210> SEQ ID NO 158
<211> LENGTH: 20
<212> TYPE: DNA
<213> ORGANISM: Artificial sequence
<220> FEATURE:
<223> OTHER INFORMATION: Synthesized

<400> SEQUENCE: 158
gtttgagttg gctccgaacg 20

<210> SEQ ID NO 159
<211> LENGTH: 18
<212> TYPE: DNA
<213> ORGANISM: Artificial sequence
<220> FEATURE:
<223> OTHER INFORMATION: Synthesized

<400> SEQUENCE: 159
ctgagggctc caccccaa 18

<210> SEQ ID NO 160
<211> LENGTH: 23
<212> TYPE: DNA
<213> ORGANISM: Artificial sequence
<220> FEATURE:
<223> OTHER INFORMATION: Synthesized

<400> SEQUENCE: 160
gtgaagagat gggagtaggc tgt 23

<210> SEQ ID NO 161
<211> LENGTH: 26
<212> TYPE: DNA
<213> ORGANISM: Artificial sequence
<220> FEATURE:
<223> OTHER INFORMATION: Synthesized

<400> SEQUENCE: 161
cccatctttt tgttttgtga gggttt 26

<210> SEQ ID NO 162
<211> LENGTH: 26
<212> TYPE: DNA
<213> ORGANISM: Artificial sequence
<220> FEATURE:
<223> OTHER INFORMATION: Synthesized

<400> SEQUENCE: 162
ttaaagcagg atatccacat tgcgta 26

<210> SEQ ID NO 163
<211> LENGTH: 22
<212> TYPE: DNA
<213> ORGANISM: Artificial sequence
<220> FEATURE:
<223> OTHER INFORMATION: Synthesized

<400> SEQUENCE: 163
ttgctgaaag tccaagagtc ct 22

<210> SEQ ID NO 164
<211> LENGTH: 23
<212> TYPE: DNA
<213> ORGANISM: Artificial sequence
<220> FEATURE:
<223> OTHER INFORMATION: Synthesized

<400> SEQUENCE: 164
ggtgagcaat gttcaggaga ttc 23

<210> SEQ ID NO 165
<211> LENGTH: 22
<212> TYPE: DNA
<213> ORGANISM: Artificial sequence
<220> FEATURE:
<223> OTHER INFORMATION: Synthesized

<400> SEQUENCE: 165
actactagat ccctggacgc tg 22

<210> SEQ ID NO 166
<211> LENGTH: 23
<212> TYPE: DNA
<213> ORGANISM: Artificial sequence
<220> FEATURE:
<223> OTHER INFORMATION: Synthesized

<400> SEQUENCE: 166
ggtggagata agggagtagg ctg 23

<210> SEQ ID NO 167
<211> LENGTH: 20
<212> TYPE: DNA
<213> ORGANISM: Artificial sequence
<220> FEATURE:
<223> OTHER INFORMATION: Synthesized

<400> SEQUENCE: 167
tgcccttcca atggatccac 20

<210> SEQ ID NO 168
<211> LENGTH: 18
<212> TYPE: DNA
<213> ORGANISM: Artificial sequence
<220> FEATURE:
<223> OTHER INFORMATION: Synthesized

<400> SEQUENCE: 168
gtccccagcc caaccctt 18

<210> SEQ ID NO 169
<211> LENGTH: 20
<212> TYPE: DNA
<213> ORGANISM: Artificial sequence
<220> FEATURE:
<223> OTHER INFORMATION: Synthesized

<400> SEQUENCE: 169
ctctggcatt ctgggagctt 20

<210> SEQ ID NO 170
<211> LENGTH: 22
<212> TYPE: DNA
<213> ORGANISM: Artificial sequence
<220> FEATURE:
<223> OTHER INFORMATION: Synthesized

<400> SEQUENCE: 170
tggtaggttt tctgggaagg ga 22

<210> SEQ ID NO 171
<211> LENGTH: 21
<212> TYPE: DNA
<213> ORGANISM: Artificial sequence
<220> FEATURE:
<223> OTHER INFORMATION: Synthesized

<400> SEQUENCE: 171
tgtcccagaa tgcaagaagc c 21

<210> SEQ ID NO 172
<211> LENGTH: 24
<212> TYPE: DNA
<213> ORGANISM: Artificial sequence
<220> FEATURE:
<223> OTHER INFORMATION: Synthesized

<400> SEQUENCE: 172
ggcattgaag tctcatggaa gcca 24

<210> SEQ ID NO 173
<211> LENGTH: 20
<212> TYPE: DNA
<213> ORGANISM: Artificial sequence
<220> FEATURE:
<223> OTHER INFORMATION: Synthesized

<400> SEQUENCE: 173
acctccgtca tgtgctgtga 20

<210> SEQ ID NO 174
<211> LENGTH: 21
<212> TYPE: DNA
<213> ORGANISM: Artificial sequence
<220> FEATURE:
<223> OTHER INFORMATION: Synthesized

<400> SEQUENCE: 174
ctcaccatcg ctatctgagc a 21

<210> SEQ ID NO 175
<211> LENGTH: 18
<212> TYPE: DNA
<213> ORGANISM: Artificial sequence
<220> FEATURE:
<223> OTHER INFORMATION: Synthesized

<400> SEQUENCE: 175
gcaaccagcc ctgtcgtc 18

<210> SEQ ID NO 176
<211> LENGTH: 21
<212> TYPE: DNA
<213> ORGANISM: Artificial sequence
<220> FEATURE:
<223> OTHER INFORMATION: Synthesized

<400> SEQUENCE: 176
gcaccaccac actatgtcga a 21

<210> SEQ ID NO 177

<211> LENGTH: 21
<212> TYPE: DNA
<213> ORGANISM: Artificial sequence
<220> FEATURE:
<223> OTHER INFORMATION: Synthesized

<400> SEQUENCE: 177
ttaacccctc ctcccagaga c 21

<210> SEQ ID NO 178
<211> LENGTH: 24
<212> TYPE: DNA
<213> ORGANISM: Artificial sequence
<220> FEATURE:
<223> OTHER INFORMATION: Synthesized

<400> SEQUENCE: 178
ttccagtgtg atgatggtga ggat 24

<210> SEQ ID NO 179
<211> LENGTH: 18
<212> TYPE: DNA
<213> ORGANISM: Artificial sequence
<220> FEATURE:
<223> OTHER INFORMATION: Synthesized

<400> SEQUENCE: 179
cagcaggcca gtgtgcag 18

<210> SEQ ID NO 180
<211> LENGTH: 18
<212> TYPE: DNA
<213> ORGANISM: Artificial sequence
<220> FEATURE:
<223> OTHER INFORMATION: Synthesized

<400> SEQUENCE: 180
ccggtctctc ccaggaca 18

<210> SEQ ID NO 181
<211> LENGTH: 20
<212> TYPE: DNA
<213> ORGANISM: Artificial sequence
<220> FEATURE:
<223> OTHER INFORMATION: Synthesized

<400> SEQUENCE: 181
gtgaggctcc cctttcttgc 20

<210> SEQ ID NO 182
<211> LENGTH: 19
<212> TYPE: DNA
<213> ORGANISM: Artificial sequence
<220> FEATURE:
<223> OTHER INFORMATION: Synthesized

<400> SEQUENCE: 182
tggtctcctc caccgcttc 19

<210> SEQ ID NO 183
<211> LENGTH: 26
<212> TYPE: DNA
<213> ORGANISM: Artificial sequence
<220> FEATURE:
<223> OTHER INFORMATION: Synthesized

<400> SEQUENCE: 183
gaaactttcc acttgataag aggtcc 26

<210> SEQ ID NO 184
<211> LENGTH: 18
<212> TYPE: DNA
<213> ORGANISM: Artificial sequence
<220> FEATURE:
<223> OTHER INFORMATION: Synthesized

<400> SEQUENCE: 184 ctccccctg gctccttc 18

<210> SEQ ID NO 185
<211> LENGTH: 19
<212> TYPE: DNA
<213> ORGANISM: Artificial sequence
<220> FEATURE:
<223> OTHER INFORMATION: Synthesized

<400> SEQUENCE: 185
ggggagtagg gccaggaag 19

<210> SEQ ID NO 186
<211> LENGTH: 23
<212> TYPE: DNA
<213> ORGANISM: Artificial sequence
<220> FEATURE:
<223> OTHER INFORMATION: Synthesized

<400> SEQUENCE: 186
gcccttctgt cttgaacatg agt 23

<210> SEQ ID NO 187
<211> LENGTH: 18
<212> TYPE: DNA
<213> ORGANISM: Artificial sequence
<220> FEATURE:
<223> OTHER INFORMATION: Synthesized

<400> SEQUENCE: 187
gtgggaggct gtcagtgg 18

<210> SEQ ID NO 188
<211> LENGTH: 16
<212> TYPE: DNA
<213> ORGANISM: Artificial sequence
<220> FEATURE:
<223> OTHER INFORMATION: Synthesized

<400> SEQUENCE: 188
gccacccgga cgcttc 16

<210> SEQ ID NO 189
<211> LENGTH: 21
<212> TYPE: DNA
<213> ORGANISM: Artificial sequence
<220> FEATURE:
<223> OTHER INFORMATION: Synthesized

<400> SEQUENCE: 189
caaacgaaac cccacacgaa c 21

<210> SEQ ID NO 190
<211> LENGTH: 17
<212> TYPE: DNA

<213> ORGANISM: Artificial sequence
<220> FEATURE:
<223> OTHER INFORMATION: Synthesized

<400> SEQUENCE: 190
gcggagggag cgagttc 17

<210> SEQ ID NO 191
<211> LENGTH: 20
<212> TYPE: DNA
<213> ORGANISM: Artificial sequence
<220> FEATURE:
<223> OTHER INFORMATION: Synthesized

<400> SEQUENCE: 191
aacatagtcc ccgctggcta 20

<210> SEQ ID NO 192
<211> LENGTH: 18
<212> TYPE: DNA
<213> ORGANISM: Artificial sequence
<220> FEATURE:
<223> OTHER INFORMATION: Synthesized

<400> SEQUENCE: 192
ggagcgctca aacccaca 18

<210> SEQ ID NO 193
<211> LENGTH: 18
<212> TYPE: DNA
<213> ORGANISM: Artificial sequence
<220> FEATURE:
<223> OTHER INFORMATION: Synthesized

<400> SEQUENCE: 193
tacaactggc ccgtgtgg 18

<210> SEQ ID NO 194
<211> LENGTH: 20
<212> TYPE: DNA
<213> ORGANISM: Artificial sequence
<220> FEATURE:
<223> OTHER INFORMATION: Synthesized

<400> SEQUENCE: 194
gtccttcttc gcctggcatc 20

<210> SEQ ID NO 195
<211> LENGTH: 17
<212> TYPE: DNA
<213> ORGANISM: Artificial sequence
<220> FEATURE:
<223> OTHER INFORMATION: Synthesized

<400> SEQUENCE: 195
tgggctggga gaccgtg 17

<210> SEQ ID NO 196
<211> LENGTH: 19
<212> TYPE: DNA
<213> ORGANISM: Artificial sequence
<220> FEATURE:
<223> OTHER INFORMATION: Synthesized

<400> SEQUENCE: 196
ccaccggctc ttcaagctc 19

<210> SEQ ID NO 197
<211> LENGTH: 16
<212> TYPE: DNA
<213> ORGANISM: Artificial sequence
<220> FEATURE:
<223> OTHER INFORMATION: Synthesized

<400> SEQUENCE: 197
catcgtcgcc gctgca 16

<210> SEQ ID NO 198
<211> LENGTH: 20
<212> TYPE: DNA
<213> ORGANISM: Artificial sequence
<220> FEATURE:
<223> OTHER INFORMATION: Synthesized

<400> SEQUENCE: 198
aacgcatagg aggggtggaa 20

<210> SEQ ID NO 199
<211> LENGTH: 22
<212> TYPE: DNA
<213> ORGANISM: Artificial sequence
<220> FEATURE:
<223> OTHER INFORMATION: Synthesized

<400> SEQUENCE: 199
cctttgggtt gggagaagaa aa 22

<210> SEQ ID NO 200
<211> LENGTH: 18
<212> TYPE: DNA
<213> ORGANISM: Artificial sequence
<220> FEATURE:
<223> OTHER INFORMATION: Synthesized

<400> SEQUENCE: 200
cacccgccgt gtacgttt 18

<210> SEQ ID NO 201
<211> LENGTH: 20
<212> TYPE: DNA
<213> ORGANISM: Artificial sequence
<220> FEATURE:
<223> OTHER INFORMATION: Synthesized

<400> SEQUENCE: 201
cggaatcggg gtctaagtgg 20

<210> SEQ ID NO 202
<211> LENGTH: 18
<212> TYPE: DNA
<213> ORGANISM: Artificial sequence
<220> FEATURE:
<223> OTHER INFORMATION: Synthesized

<400> SEQUENCE: 202
cctagcgatc agggcacc 18

<210> SEQ ID NO 203
<211> LENGTH: 20
<212> TYPE: DNA
<213> ORGANISM: Artificial sequence
<220> FEATURE:

<223> OTHER INFORMATION: Synthesized

<400> SEQUENCE: 203
gatgagagag cagtctgcgt 20

<210> SEQ ID NO 204
<211> LENGTH: 20
<212> TYPE: DNA
<213> ORGANISM: Artificial sequence
<220> FEATURE:
<223> OTHER INFORMATION: Synthesized

<400> SEQUENCE: 204
cgttctcgcg ctctgcttac 20

<210> SEQ ID NO 205
<211> LENGTH: 16
<212> TYPE: DNA
<213> ORGANISM: Artificial sequence
<220> FEATURE:
<223> OTHER INFORMATION: Synthesized

<400> SEQUENCE: 205
gacccccgct gctcac 16

<210> SEQ ID NO 206
<211> LENGTH: 17
<212> TYPE: DNA
<213> ORGANISM: Artificial sequence
<220> FEATURE:
<223> OTHER INFORMATION: Synthesized

<400> SEQUENCE: 206
ccccctaagc cgctgtt 17

<210> SEQ ID NO 207
<211> LENGTH: 18
<212> TYPE: DNA
<213> ORGANISM: Artificial sequence
<220> FEATURE:
<223> OTHER INFORMATION: Synthesized

<400> SEQUENCE: 207
ccacacgggc cagttgta 18

<210> SEQ ID NO 208
<211> LENGTH: 22
<212> TYPE: DNA
<213> ORGANISM: Artificial sequence
<220> FEATURE:
<223> OTHER INFORMATION: Synthesized

<400> SEQUENCE: 208
tggccgtttt cgaagaggta ga 22

<210> SEQ ID NO 209
<211> LENGTH: 17
<212> TYPE: DNA
<213> ORGANISM: Artificial sequence
<220> FEATURE:
<223> OTHER INFORMATION: Synthesized

<400> SEQUENCE: 209
caccgttggg ctggtcc 17

<210> SEQ ID NO 210
<211> LENGTH: 19
<212> TYPE: DNA
<213> ORGANISM: Artificial sequence
<220> FEATURE:
<223> OTHER INFORMATION: Synthesized

<400> SEQUENCE: 210
cgagcttgaa gagccggtg 19

<210> SEQ ID NO 211
<211> LENGTH: 17
<212> TYPE: DNA
<213> ORGANISM: Artificial sequence
<220> FEATURE:
<223> OTHER INFORMATION: Synthesized

<400> SEQUENCE: 211
cgcccacccg agttcct 17

<210> SEQ ID NO 212
<211> LENGTH: 16
<212> TYPE: DNA
<213> ORGANISM: Artificial sequence
<220> FEATURE:
<223> OTHER INFORMATION: Synthesized

<400> SEQUENCE: 212
tggccgggac tggagg 16

<210> SEQ ID NO 213
<211> LENGTH: 22
<212> TYPE: DNA
<213> ORGANISM: Artificial sequence
<220> FEATURE:
<223> OTHER INFORMATION: Synthesized

<400> SEQUENCE: 213
ggtaatacgt tccggcactt cg 22

<210> SEQ ID NO 214
<211> LENGTH: 19
<212> TYPE: DNA
<213> ORGANISM: Artificial sequence
<220> FEATURE:
<223> OTHER INFORMATION: Synthesized

<400> SEQUENCE: 214
gcccccactt tccaactcc 19

<210> SEQ ID NO 215
<211> LENGTH: 18
<212> TYPE: DNA
<213> ORGANISM: Artificial sequence
<220> FEATURE:
<223> OTHER INFORMATION: Synthesized

<400> SEQUENCE: 215
gcggttccga agtccctg 18

<210> SEQ ID NO 216
<211> LENGTH: 17
<212> TYPE: DNA
<213> ORGANISM: Artificial sequence
<220> FEATURE:
<223> OTHER INFORMATION: Synthesized

<400> SEQUENCE: 216
ctctccagcc ctcggtg 17

<210> SEQ ID NO 217
<211> LENGTH: 50
<212> TYPE: DNA
<213> ORGANISM: Artificial sequence
<220> FEATURE:
<223> OTHER INFORMATION: Synthesized

<400> SEQUENCE: 217
aatgatacgg cgaccaccga gatctacact ctttccctac acgacgctct 50

<210> SEQ ID NO 218
<211> LENGTH: 24
<212> TYPE: DNA
<213> ORGANISM: Artificial sequence
<220> FEATURE:
<223> OTHER INFORMATION: Synthesized

<400> SEQUENCE: 218
caagcagaag acggcatacg agat 24

<210> SEQ ID NO 219
<211> LENGTH: 28
<212> TYPE: DNA
<213> ORGANISM: Artificial sequence
<220> FEATURE:
<223> OTHER INFORMATION: Synthesized

<400> SEQUENCE: 219
gtgactggag ttccttggca cccgagaa 28

<210> SEQ ID NO 220
<211> LENGTH: 38
<212> TYPE: DNA
<213> ORGANISM: Artificial sequence
<220> FEATURE:
<223> OTHER INFORMATION: Synthesized

<400> SEQUENCE: 220
cttggcaccc gagaattcca ttgttccttg acgcagag 38

<210> SEQ ID NO 221
<211> LENGTH: 40
<212> TYPE: DNA
<213> ORGANISM: Artificial sequence
<220> FEATURE:
<223> OTHER INFORMATION: Synthesized

<400> SEQUENCE: 221
cttggcaccc gagaattcca gacctggggt atgagcctga 40

<210> SEQ ID NO 222
<211> LENGTH: 38
<212> TYPE: DNA
<213> ORGANISM: Artificial sequence
<220> FEATURE:
<223> OTHER INFORMATION: Synthesized

<400> SEQUENCE: 222
cttggcaccc gagaattcca aggctgaagc tggcgaga 38

<210> SEQ ID NO 223
<211> LENGTH: 40

<212> TYPE: DNA
<213> ORGANISM: Artificial sequence
<220> FEATURE:
<223> OTHER INFORMATION: Synthesized

<400> SEQUENCE: 223
cttggcaccc gagaattcca tgaggacgat ggcagagacg 40

<210> SEQ ID NO 224
<211> LENGTH: 40
<212> TYPE: DNA
<213> ORGANISM: Artificial sequence
<220> FEATURE:
<223> OTHER INFORMATION: Synthesized

<400> SEQUENCE: 224
cttggcaccc gagaattcca gtacagcgaa ggcagagagt 40

<210> SEQ ID NO 225
<211> LENGTH: 41
<212> TYPE: DNA
<213> ORGANISM: Artificial sequence
<220> FEATURE:
<223> OTHER INFORMATION: Synthesized

<400> SEQUENCE: 225
cttggcaccc gagaattcca cacacaggag gaggaaggtg a 41

<210> SEQ ID NO 226
<211> LENGTH: 39
<212> TYPE: DNA
<213> ORGANISM: Artificial sequence
<220> FEATURE:
<223> OTHER INFORMATION: Synthesized

<400> SEQUENCE: 226
cttggcaccc gagaattcca tgtgtggaca tgggctgtg 39

<210> SEQ ID NO 227
<211> LENGTH: 38
<212> TYPE: DNA
<213> ORGANISM: Artificial sequence
<220> FEATURE:
<223> OTHER INFORMATION: Synthesized

<400> SEQUENCE: 227
cttggcaccc gagaattcca acccaagtca ggggcgaa 38

<210> SEQ ID NO 228
<211> LENGTH: 44
<212> TYPE: DNA
<213> ORGANISM: Artificial sequence
<220> FEATURE:
<223> OTHER INFORMATION: Synthesized

<400> SEQUENCE: 228
cttggcaccc gagaattcca gcgtgcaaaa gaaatgccaa gaag 44

<210> SEQ ID NO 229
<211> LENGTH: 41
<212> TYPE: DNA
<213> ORGANISM: Artificial sequence
<220> FEATURE:
<223> OTHER INFORMATION: Synthesized

<400> SEQUENCE: 229
cttggcaccc gagaattcca tagtcactgg cagcaacagt c 41

<210> SEQ ID NO 230
<211> LENGTH: 38
<212> TYPE: DNA
<213> ORGANISM: Artificial sequence
<220> FEATURE:
<223> OTHER INFORMATION: Synthesized

<400> SEQUENCE: 230
cttggcaccc gagaattcca ctgcaaggcc tcgggaga 38

<210> SEQ ID NO 231
<211> LENGTH: 41
<212> TYPE: DNA
<213> ORGANISM: Artificial sequence
<220> FEATURE:
<223> OTHER INFORMATION: Synthesized

<400> SEQUENCE: 231
cttggcaccc gagaattcca attcctggga agtcctcagc t 41

<210> SEQ ID NO 232
<211> LENGTH: 38
<212> TYPE: DNA
<213> ORGANISM: Artificial sequence
<220> FEATURE:
<223> OTHER INFORMATION: Synthesized

<400> SEQUENCE: 232
cttggcaccc gagaattcca gcttggagcc aggtgcct 38

<210> SEQ ID NO 233
<211> LENGTH: 43
<212> TYPE: DNA
<213> ORGANISM: Artificial sequence
<220> FEATURE:
<223> OTHER INFORMATION: Synthesized

<400> SEQUENCE: 233
cttggcaccc gagaattcca catttcccac cctttctcga cgg 43

<210> SEQ ID NO 234
<211> LENGTH: 38
<212> TYPE: DNA
<213> ORGANISM: Artificial sequence
<220> FEATURE:
<223> OTHER INFORMATION: Synthesized

<400> SEQUENCE: 234
cttggcaccc gagaattcca acgggcctgt gtcaagga 38

<210> SEQ ID NO 235
<211> LENGTH: 38
<212> TYPE: DNA
<213> ORGANISM: Artificial sequence
<220> FEATURE:
<223> OTHER INFORMATION: Synthesized

<400> SEQUENCE: 235
cttggcaccc gagaattcca atgcgtcctc gggttcgt 38

<210> SEQ ID NO 236
<211> LENGTH: 38
<212> TYPE: DNA
<213> ORGANISM: Artificial sequence
<220> FEATURE:
<223> OTHER INFORMATION: Synthesized

<400> SEQUENCE: 236
cttggcaccc gagaattcca agcctaggcc gattcgac 38

<210> SEQ ID NO 237
<211> LENGTH: 38
<212> TYPE: DNA
<213> ORGANISM: Artificial sequence
<220> FEATURE:
<223> OTHER INFORMATION: Synthesized

<400> SEQUENCE: 237
cttggcaccc gagaattcca gattcgcggg cacagacg 38

<210> SEQ ID NO 238
<211> LENGTH: 38
<212> TYPE: DNA
<213> ORGANISM: Artificial sequence
<220> FEATURE:
<223> OTHER INFORMATION: Synthesized

<400> SEQUENCE: 238
cttggcaccc gagaattcca ttccagctcc gcctcctc 38

<210> SEQ ID NO 239
<211> LENGTH: 44
<212> TYPE: DNA
<213> ORGANISM: Artificial sequence
<220> FEATURE:
<223> OTHER INFORMATION: Synthesized

<400> SEQUENCE: 239
cttggcaccc gagaattcca cccatatcgt caatcttctc gagg 44

<210> SEQ ID NO 240
<211> LENGTH: 45
<212> TYPE: DNA
<213> ORGANISM: Artificial sequence
<220> FEATURE:
<223> OTHER INFORMATION: Synthesized

<400> SEQUENCE: 240
cttggcaccc gagaattcca tcacagtacc acagagtcta gactc 45

<210> SEQ ID NO 241
<211> LENGTH: 44
<212> TYPE: DNA
<213> ORGANISM: Artificial sequence
<220> FEATURE:
<223> OTHER INFORMATION: Synthesized

<400> SEQUENCE: 241
cttggcaccc gagaattcca aacctcttgt cctccaattt gtcc 44

<210> SEQ ID NO 242
<211> LENGTH: 42
<212> TYPE: DNA
<213> ORGANISM: Artificial sequence
<220> FEATURE:
<223> OTHER INFORMATION: Synthesized

<400> SEQUENCE: 242
cttggcaccc gagaattcca cctgctgcta tgcctcatct tc 42

<210> SEQ ID NO 243
<211> LENGTH: 39
<212> TYPE: DNA
<213> ORGANISM: Artificial sequence
<220> FEATURE:
<223> OTHER INFORMATION: Synthesized

<400> SEQUENCE: 243
cttggcaccc gagaattcca cacgggacca tgcaagacc 39

<210> SEQ ID NO 244
<211> LENGTH: 42
<212> TYPE: DNA
<213> ORGANISM: Artificial sequence
<220> FEATURE:
<223> OTHER INFORMATION: Synthesized

<400> SEQUENCE: 244
cttggcaccc gagaattcca tgggctttcg caagattcct at 42

<210> SEQ ID NO 245
<211> LENGTH: 39
<212> TYPE: DNA
<213> ORGANISM: Artificial sequence
<220> FEATURE:
<223> OTHER INFORMATION: Synthesized

<400> SEQUENCE: 245
cttggcaccc gagaattcca cgtagggctt tcccccact 39

<210> SEQ ID NO 246
<211> LENGTH: 51
<212> TYPE: DNA
<213> ORGANISM: Artificial sequence
<220> FEATURE:
<223> OTHER INFORMATION: Synthesized

<400> SEQUENCE: 246
cttggcaccc gagaattcca cctctattac caattttctt ttgtctttgg g 51

<210> SEQ ID NO 247
<211> LENGTH: 42
<212> TYPE: DNA
<213> ORGANISM: Artificial sequence
<220> FEATURE:
<223> OTHER INFORMATION: Synthesized

<400> SEQUENCE: 247
cttggcaccc gagaattcca acacaatgtg gctatcctgc tt 42

<210> SEQ ID NO 248
<211> LENGTH: 38
<212> TYPE: DNA
<213> ORGANISM: Artificial sequence
<220> FEATURE:
<223> OTHER INFORMATION: Synthesized

<400> SEQUENCE: 248
cttggcaccc gagaattcca ggcaacggtc aggtctct 38

<210> SEQ ID NO 249
<211> LENGTH: 43
<212> TYPE: DNA
<213> ORGANISM: Artificial sequence
<220> FEATURE:
<223> OTHER INFORMATION: Synthesized

<400> SEQUENCE: 249
cttggcaccc gagaattcca ctctgccgat ccatactgcg gaa 43

<210> SEQ ID NO 250
<211> LENGTH: 42
<212> TYPE: DNA
<213> ORGANISM: Artificial sequence
<220> FEATURE:
<223> OTHER INFORMATION: Synthesized

<400> SEQUENCE: 250
cttggcaccc gagaattcca cacttccttt ccatggctgc ta 42

<210> SEQ ID NO 251
<211> LENGTH: 39
<212> TYPE: DNA
<213> ORGANISM: Artificial sequence
<220> FEATURE:
<223> OTHER INFORMATION: Synthesized

<400> SEQUENCE: 251
cttggcaccc gagaattcca ccgtttggga ctctaccgt 39

<210> SEQ ID NO 252
<211> LENGTH: 38
<212> TYPE: DNA
<213> ORGANISM: Artificial sequence
<220> FEATURE:
<223> OTHER INFORMATION: Synthesized

<400> SEQUENCE: 252
cttggcaccc gagaattcca cgtgtgcact tcgcttca 38

<210> SEQ ID NO 253
<211> LENGTH: 44
<212> TYPE: DNA
<213> ORGANISM: Artificial sequence
<220> FEATURE:
<223> OTHER INFORMATION: Synthesized

<400> SEQUENCE: 253
cttggcaccc gagaattcca ttgcccaagg tcttacataa gagg 44

<210> SEQ ID NO 254
<211> LENGTH: 45
<212> TYPE: DNA
<213> ORGANISM: Artificial sequence
<220> FEATURE:
<223> OTHER INFORMATION: Synthesized

<400> SEQUENCE: 254
cttggcaccc gagaattcca gtttgtttaa ggactgggag gagtt 45

<210> SEQ ID NO 255
<211> LENGTH: 41
<212> TYPE: DNA
<213> ORGANISM: Artificial sequence
<220> FEATURE:
<223> OTHER INFORMATION: Synthesized

<400> SEQUENCE: 255
cttggcaccc gagaattcca ggtctgttca ccagcaccat g 41

<210> SEQ ID NO 256

<211> LENGTH: 38
<212> TYPE: DNA
<213> ORGANISM: Artificial sequence
<220> FEATURE:
<223> OTHER INFORMATION: Synthesized

<400> SEQUENCE: 256
cttggcaccc gagaattcca ctgtgccttg ggtggctt 38

<210> SEQ ID NO 257
<211> LENGTH: 47
<212> TYPE: DNA
<213> ORGANISM: Artificial sequence
<220> FEATURE:
<223> OTHER INFORMATION: Synthesized

<400> SEQUENCE: 257
cttggcaccc gagaattcca ttgccttctg atttctttcc ttctatt 47

<210> SEQ ID NO 258
<211> LENGTH: 43
<212> TYPE: DNA
<213> ORGANISM: Artificial sequence
<220> FEATURE:
<223> OTHER INFORMATION: Synthesized

<400> SEQUENCE: 258
cttggcaccc gagaattcca gagtctccgg aacattgttc acc 43

<210> SEQ ID NO 259
<211> LENGTH: 41
<212> TYPE: DNA
<213> ORGANISM: Artificial sequence
<220> FEATURE:
<223> OTHER INFORMATION: Synthesized

<400> SEQUENCE: 259
cttggcaccc gagaattcca agttgatgaa tctggccacc t 41

<210> SEQ ID NO 260
<211> LENGTH: 48
<212> TYPE: DNA
<213> ORGANISM: Artificial sequence
<220> FEATURE:
<223> OTHER INFORMATION: Synthesized

<400> SEQUENCE: 260
cttggcaccc gagaattcca cagctatgtt aatgttaata tgggccta 48

<210> SEQ ID NO 261
<211> LENGTH: 46
<212> TYPE: DNA
<213> ORGANISM: Artificial sequence
<220> FEATURE:
<223> OTHER INFORMATION: Synthesized

<400> SEQUENCE: 261
cttggcaccc gagaattcca tatttggtgt cttttggagt gtggat 46

<210> SEQ ID NO 262
<211> LENGTH: 41
<212> TYPE: DNA
<213> ORGANISM: Artificial sequence
<220> FEATURE:
<223> OTHER INFORMATION: Synthesized

<400> SEQUENCE: 262
cttggcaccc gagaattcca tagaggcagg tcccctagaa g 41

<210> SEQ ID NO 263
<211> LENGTH: 46
<212> TYPE: DNA
<213> ORGANISM: Artificial sequence
<220> FEATURE:
<223> OTHER INFORMATION: Synthesized

<400> SEQUENCE: 263
cttggcaccc gagaattcca caatgttagt atcccttgga ctcaca 46

<210> SEQ ID NO 264
<211> LENGTH: 47
<212> TYPE: DNA
<213> ORGANISM: Artificial sequence
<220> FEATURE:
<223> OTHER INFORMATION: Synthesized

<400> SEQUENCE: 264
cttggcaccc gagaattcca acaggaggac attattgata gatgtca 47

<210> SEQ ID NO 265
<211> LENGTH: 43
<212> TYPE: DNA
<213> ORGANISM: Artificial sequence
<220> FEATURE:
<223> OTHER INFORMATION: Synthesized

<400> SEQUENCE: 265
cttggcaccc gagaattcca aaccttacca agtatttgcc ctt 43

<210> SEQ ID NO 266
<211> LENGTH: 45
<212> TYPE: DNA
<213> ORGANISM: Artificial sequence
<220> FEATURE:
<223> OTHER INFORMATION: Synthesized

<400> SEQUENCE: 266
cttggcaccc gagaattcca tctgtggaag gctgggattc tatat 45

<210> SEQ ID NO 267
<211> LENGTH: 42
<212> TYPE: DNA
<213> ORGANISM: Artificial sequence
<220> FEATURE:
<223> OTHER INFORMATION: Synthesized

<400> SEQUENCE: 267
cttggcaccc gagaattcca gggacaaatc tttctgttcc ca 42

<210> SEQ ID NO 268
<211> LENGTH: 39
<212> TYPE: DNA
<213> ORGANISM: Artificial sequence
<220> FEATURE:
<223> OTHER INFORMATION: Synthesized

<400> SEQUENCE: 268
cttggcaccc gagaattcca ggccagaggc aaatcaggt 39

<210> SEQ ID NO 269
<211> LENGTH: 42
<212> TYPE: DNA

<213> ORGANISM: Artificial sequence
<220> FEATURE:
<223> OTHER INFORMATION: Synthesized

<400> SEQUENCE: 269
cttggcaccc gagaattcca cagtcaggaa gacagcctac tc 42

<210> SEQ ID NO 270
<211> LENGTH: 44
<212> TYPE: DNA
<213> ORGANISM: Artificial sequence
<220> FEATURE:
<223> OTHER INFORMATION: Synthesized

<400> SEQUENCE: 270
cttggcaccc gagaattcca aatactgtct ctgccatatc gtca 44

<210> SEQ ID NO 271
<211> LENGTH: 42
<212> TYPE: DNA
<213> ORGANISM: Artificial sequence
<220> FEATURE:
<223> OTHER INFORMATION: Synthesized

<400> SEQUENCE: 271
cttggcaccc gagaattcca gtgtgtttca tgagtgggag ga 42

<210> SEQ ID NO 272
<211> LENGTH: 44
<212> TYPE: DNA
<213> ORGANISM: Artificial sequence
<220> FEATURE:
<223> OTHER INFORMATION: Synthesized

<400> SEQUENCE: 272
cttggcaccc gagaattcca tttgccttct gacttctttc cgtc 44

<210> SEQ ID NO 273
<211> LENGTH: 40
<212> TYPE: DNA
<213> ORGANISM: Artificial sequence
<220> FEATURE:
<223> OTHER INFORMATION: Synthesized

<400> SEQUENCE: 273
cttggcaccc gagaattcca cacagcactc aggcaagcta 40

<210> SEQ ID NO 274
<211> LENGTH: 39
<212> TYPE: DNA
<213> ORGANISM: Artificial sequence
<220> FEATURE:
<223> OTHER INFORMATION: Synthesized

<400> SEQUENCE: 274
cttggcaccc gagaattcca gtcactgcca tggaggagc 39

<210> SEQ ID NO 275
<211> LENGTH: 40
<212> TYPE: DNA
<213> ORGANISM: Artificial sequence
<220> FEATURE:
<223> OTHER INFORMATION: Synthesized

<400> SEQUENCE: 275
cttggcaccc gagaattcca ccatgggact gactttctgc 40

<210> SEQ ID NO 276
<211> LENGTH: 43
<212> TYPE: DNA
<213> ORGANISM: Artificial sequence
<220> FEATURE:
<223> OTHER INFORMATION: Synthesized

<400> SEQUENCE: 276
cttggcaccc gagaattcca actgctcttt tcacccatct aca 43

<210> SEQ ID NO 277
<211> LENGTH: 41
<212> TYPE: DNA
<213> ORGANISM: Artificial sequence
<220> FEATURE:
<223> OTHER INFORMATION: Synthesized

<400> SEQUENCE: 277
cttggcaccc gagaattcca tgtccccgga cgatattgaa c 41

<210> SEQ ID NO 278
<211> LENGTH: 42
<212> TYPE: DNA
<213> ORGANISM: Artificial sequence
<220> FEATURE:
<223> OTHER INFORMATION: Synthesized

<400> SEQUENCE: 278
cttggcaccc gagaattcca cagatgaagc tcccagaatg cc 42

<210> SEQ ID NO 279
<211> LENGTH: 42
<212> TYPE: DNA
<213> ORGANISM: Artificial sequence
<220> FEATURE:
<223> OTHER INFORMATION: Synthesized

<400> SEQUENCE: 279
cttggcaccc gagaattcca tgtcatcttc tgtcccttcc ca 42

<210> SEQ ID NO 280
<211> LENGTH: 44
<212> TYPE: DNA
<213> ORGANISM: Artificial sequence
<220> FEATURE:
<223> OTHER INFORMATION: Synthesized

<400> SEQUENCE: 280
cttggcaccc gagaattcca caactctgtc tccttcctct tcct 44

<210> SEQ ID NO 281
<211> LENGTH: 39
<212> TYPE: DNA
<213> ORGANISM: Artificial sequence
<220> FEATURE:
<223> OTHER INFORMATION: Synthesized

<400> SEQUENCE: 281
cttggcaccc gagaattcca tgtgcagctg tgggttgat 39

<210> SEQ ID NO 282
<211> LENGTH: 42
<212> TYPE: DNA
<213> ORGANISM: Artificial sequence
<220> FEATURE:

<223> OTHER INFORMATION: Synthesized

<400> SEQUENCE: 282
cttggcaccc gagaattcca caagcagtca cagcacatga cg 42

<210> SEQ ID NO 283
<211> LENGTH: 43
<212> TYPE: DNA
<213> ORGANISM: Artificial sequence
<220> FEATURE:
<223> OTHER INFORMATION: Synthesized

<400> SEQUENCE: 283
cttggcaccc gagaattcca cctctgattc ctcactgatt gct 43

<210> SEQ ID NO 284
<211> LENGTH: 42
<212> TYPE: DNA
<213> ORGANISM: Artificial sequence
<220> FEATURE:
<223> OTHER INFORMATION: Synthesized

<400> SEQUENCE: 284
cttggcaccc gagaattcca ttgcgtgtgg agtatttgga tg 42

<210> SEQ ID NO 285
<211> LENGTH: 42
<212> TYPE: DNA
<213> ORGANISM: Artificial sequence
<220> FEATURE:
<223> OTHER INFORMATION: Synthesized

<400> SEQUENCE: 285
cttggcaccc gagaattcca tcttgggcct gtgttatctc ct 42

<210> SEQ ID NO 286
<211> LENGTH: 44
<212> TYPE: DNA
<213> ORGANISM: Artificial sequence
<220> FEATURE:
<223> OTHER INFORMATION: Synthesized

<400> SEQUENCE: 286
cttggcaccc gagaattcca acatgtgtaa cagttcctgc atgg 44

<210> SEQ ID NO 287
<211> LENGTH: 46
<212> TYPE: DNA
<213> ORGANISM: Artificial sequence
<220> FEATURE:
<223> OTHER INFORMATION: Synthesized

<400> SEQUENCE: 287
cttggcaccc gagaattcca cttgcttctc ttttcctatc ctgagt 46

<210> SEQ ID NO 288
<211> LENGTH: 41
<212> TYPE: DNA
<213> ORGANISM: Artificial sequence
<220> FEATURE:
<223> OTHER INFORMATION: Synthesized

<400> SEQUENCE: 288
cttggcaccc gagaattcca ctttgaggtg cgtgtttgtg c 41

<210> SEQ ID NO 289
<211> LENGTH: 39
<212> TYPE: DNA
<213> ORGANISM: Artificial sequence
<220> FEATURE:
<223> OTHER INFORMATION: Synthesized

<400> SEQUENCE: 289
cttggcaccc gagaattcca gcaagaaagg ggagcctca 39

<210> SEQ ID NO 290
<211> LENGTH: 43
<212> TYPE: DNA
<213> ORGANISM: Artificial sequence
<220> FEATURE:
<223> OTHER INFORMATION: Synthesized

<400> SEQUENCE: 290
cttggcaccc gagaattcca atcacctttc cttgcctctt tcc 43

<210> SEQ ID NO 291
<211> LENGTH: 40
<212> TYPE: DNA
<213> ORGANISM: Artificial sequence
<220> FEATURE:
<223> OTHER INFORMATION: Synthesized

<400> SEQUENCE: 291
cttggcaccc gagaattcca ttctcccct cctctgttgc 40

<210> SEQ ID NO 292
<211> LENGTH: 41
<212> TYPE: DNA
<213> ORGANISM: Artificial sequence
<220> FEATURE:
<223> OTHER INFORMATION: Synthesized

<400> SEQUENCE: 292
cttggcaccc gagaattcca cttcgagatg ttccgagagc t 41

<210> SEQ ID NO 293
<211> LENGTH: 41
<212> TYPE: DNA
<213> ORGANISM: Artificial sequence
<220> FEATURE:
<223> OTHER INFORMATION: Synthesized

<400> SEQUENCE: 293
cttggcaccc gagaattcca cctccctgct tctgtctcct a 41

<210> SEQ ID NO 294
<211> LENGTH: 40
<212> TYPE: DNA
<213> ORGANISM: Artificial sequence
<220> FEATURE:
<223> OTHER INFORMATION: Synthesized

<400> SEQUENCE: 294
cttggcaccc gagaattcca tcagtctacc tcccgccata 40

<210> SEQ ID NO 295
<211> LENGTH: 40
<212> TYPE: DNA
<213> ORGANISM: Artificial sequence
<220> FEATURE:
<223> OTHER INFORMATION: Synthesized

<400> SEQUENCE: 295
cttggcaccc gagaattcca gaaacttgct ccgaggtcca 40

<210> SEQ ID NO 296
<211> LENGTH: 40
<212> TYPE: DNA
<213> ORGANISM: Artificial sequence
<220> FEATURE:
<223> OTHER INFORMATION: Synthesized

<400> SEQUENCE: 296
cttggcaccc gagaattcca catccagcag ggaatgcagt 40

<210> SEQ ID NO 297
<211> LENGTH: 44
<212> TYPE: DNA
<213> ORGANISM: Artificial sequence
<220> FEATURE:
<223> OTHER INFORMATION: Synthesized

<400> SEQUENCE: 297
cttggcaccc gagaattcca gacacgatgc cattgttatc aaga 44

<210> SEQ ID NO 298
<211> LENGTH: 40
<212> TYPE: DNA
<213> ORGANISM: Artificial sequence
<220> FEATURE:
<223> OTHER INFORMATION: Synthesized

<400> SEQUENCE: 298
cttggcaccc gagaattcca ctgtctccag gagcagcttc 40

<210> SEQ ID NO 299
<211> LENGTH: 42
<212> TYPE: DNA
<213> ORGANISM: Artificial sequence
<220> FEATURE:
<223> OTHER INFORMATION: Synthesized

<400> SEQUENCE: 299
cttggcaccc gagaattcca cggaggtgag tacagaaagt gg 42

<210> SEQ ID NO 300
<211> LENGTH: 39
<212> TYPE: DNA
<213> ORGANISM: Artificial sequence
<220> FEATURE:
<223> OTHER INFORMATION: Synthesized

<400> SEQUENCE: 300
cttggcaccc gagaattcca ggaggcagct tgtgacacg 39

<210> SEQ ID NO 301
<211> LENGTH: 40
<212> TYPE: DNA
<213> ORGANISM: Artificial sequence
<220> FEATURE:
<223> OTHER INFORMATION: Synthesized

<400> SEQUENCE: 301
cttggcaccc gagaattcca ctcgtccagg atgctctcag 40

<210> SEQ ID NO 302
<211> LENGTH: 38

<212> TYPE: DNA
<213> ORGANISM: Artificial sequence
<220> FEATURE:
<223> OTHER INFORMATION: Synthesized

<400> SEQUENCE: 302
cttggcaccc gagaattcca gtggtggacg tggtggtg 38

<210> SEQ ID NO 303
<211> LENGTH: 44
<212> TYPE: DNA
<213> ORGANISM: Artificial sequence
<220> FEATURE:
<223> OTHER INFORMATION: Synthesized

<400> SEQUENCE: 303
cttggcaccc gagaattcca tgattttctg gttcttctcc gcat 44

<210> SEQ ID NO 304
<211> LENGTH: 44
<212> TYPE: DNA
<213> ORGANISM: Artificial sequence
<220> FEATURE:
<223> OTHER INFORMATION: Synthesized

<400> SEQUENCE: 304
cttggcaccc gagaattcca gaggtatcca catcctcttc ctca 44

<210> SEQ ID NO 305
<211> LENGTH: 40
<212> TYPE: DNA
<213> ORGANISM: Artificial sequence
<220> FEATURE:
<223> OTHER INFORMATION: Synthesized

<400> SEQUENCE: 305
cttggcaccc gagaattcca aggacttccc aggaatccag 40

<210> SEQ ID NO 306
<211> LENGTH: 38
<212> TYPE: DNA
<213> ORGANISM: Artificial sequence
<220> FEATURE:
<223> OTHER INFORMATION: Synthesized

<400> SEQUENCE: 306
cttggcaccc gagaattcca agctaggagg cccgactt 38

<210> SEQ ID NO 307
<211> LENGTH: 38
<212> TYPE: DNA
<213> ORGANISM: Artificial sequence
<220> FEATURE:
<223> OTHER INFORMATION: Synthesized

<400> SEQUENCE: 307
cttggcaccc gagaattcca acaacggcct tgaccctg 38

<210> SEQ ID NO 308
<211> LENGTH: 43
<212> TYPE: DNA
<213> ORGANISM: Artificial sequence
<220> FEATURE:
<223> OTHER INFORMATION: Synthesized

<400> SEQUENCE: 308
cttggcaccc gagaattcca ccaccccaaa tctgttaatc acc 43

<210> SEQ ID NO 309
<211> LENGTH: 40
<212> TYPE: DNA
<213> ORGANISM: Artificial sequence
<220> FEATURE:
<223> OTHER INFORMATION: Synthesized

<400> SEQUENCE: 309
cttggcaccc gagaattcca aacacttccc cgcgacttgg 40

<210> SEQ ID NO 310
<211> LENGTH: 38
<212> TYPE: DNA
<213> ORGANISM: Artificial sequence
<220> FEATURE:
<223> OTHER INFORMATION: Synthesized

<400> SEQUENCE: 310
cttggcaccc gagaattcca cgtgaagggg aggacgga 38

<210> SEQ ID NO 311
<211> LENGTH: 38
<212> TYPE: DNA
<213> ORGANISM: Artificial sequence
<220> FEATURE:
<223> OTHER INFORMATION: Synthesized

<400> SEQUENCE: 311
cttggcaccc gagaattcca ggggccatga tgtggagg 38

<210> SEQ ID NO 312
<211> LENGTH: 38
<212> TYPE: DNA
<213> ORGANISM: Artificial sequence
<220> FEATURE:
<223> OTHER INFORMATION: Synthesized

<400> SEQUENCE: 312
cttggcaccc gagaattcca aaggtgaagg ggcaggac 38

<210> SEQ ID NO 313
<211> LENGTH: 38
<212> TYPE: DNA
<213> ORGANISM: Artificial sequence
<220> FEATURE:
<223> OTHER INFORMATION: Synthesized

<400> SEQUENCE: 313
cttggcaccc gagaattcca gcggaaagga aggggagg 38

<210> SEQ ID NO 314
<211> LENGTH: 37
<212> TYPE: DNA
<213> ORGANISM: Artificial sequence
<220> FEATURE:
<223> OTHER INFORMATION: Synthesized

<400> SEQUENCE: 314
cttggcaccc gagaattcca gcagcacctc gcggtag 37

<210> SEQ ID NO 315
<211> LENGTH: 42
<212> TYPE: DNA
<213> ORGANISM: Artificial sequence
<220> FEATURE:
<223> OTHER INFORMATION: Synthesized

<400> SEQUENCE: 315
cttggcaccc gagaattcca ggaaagtata ggcccctcac tc 42

<210> SEQ ID NO 316
<211> LENGTH: 38
<212> TYPE: DNA
<213> ORGANISM: Artificial sequence
<220> FEATURE:
<223> OTHER INFORMATION: Synthesized

<400> SEQUENCE: 316
cttggcaccc gagaattcca ctctccatgt tcggggca 38

<210> SEQ ID NO 317
<211> LENGTH: 47
<212> TYPE: DNA
<213> ORGANISM: Artificial sequence
<220> FEATURE:
<223> OTHER INFORMATION: Synthesized

<400> SEQUENCE: 317
cttggcaccc gagaattcca gaggattctt gtcaacaaga aaaaccc 47

<210> SEQ ID NO 318
<211> LENGTH: 43
<212> TYPE: DNA
<213> ORGANISM: Artificial sequence
<220> FEATURE:
<223> OTHER INFORMATION: Synthesized

<400> SEQUENCE: 318
cttggcaccc gagaattcca acaagaggtt ggtgagtgat tgg 43

<210> SEQ ID NO 319
<211> LENGTH: 46
<212> TYPE: DNA
<213> ORGANISM: Artificial sequence
<220> FEATURE:
<223> OTHER INFORMATION: Synthesized

<400> SEQUENCE: 319
cttggcaccc gagaattcca gtccagaaga accaacaaga agatga 46

<210> SEQ ID NO 320
<211> LENGTH: 45
<212> TYPE: DNA
<213> ORGANISM: Artificial sequence
<220> FEATURE:
<223> OTHER INFORMATION: Synthesized

<400> SEQUENCE: 320
cttggcaccc gagaattcca catagaggtt ccttgagcag gaatc 45

<210> SEQ ID NO 321
<211> LENGTH: 43
<212> TYPE: DNA
<213> ORGANISM: Artificial sequence
<220> FEATURE:
<223> OTHER INFORMATION: Synthesized

<400> SEQUENCE: 321
cttggcaccc gagaattcca cactcccata ggaatcttgc gaa 43

<210> SEQ ID NO 322
<211> LENGTH: 43
<212> TYPE: DNA
<213> ORGANISM: Artificial sequence
<220> FEATURE:
<223> OTHER INFORMATION: Synthesized

<400> SEQUENCE: 322
cttggcaccc gagaattcca cccccaatac cacatcatcc ata 43

<210> SEQ ID NO 323
<211> LENGTH: 47
<212> TYPE: DNA
<213> ORGANISM: Artificial sequence
<220> FEATURE:
<223> OTHER INFORMATION: Synthesized

<400> SEQUENCE: 323
cttggcaccc gagaattcca agggttcaaa tgtataccca aagacaa 47

<210> SEQ ID NO 324
<211> LENGTH: 48
<212> TYPE: DNA
<213> ORGANISM: Artificial sequence
<220> FEATURE:
<223> OTHER INFORMATION: Synthesized

<400> SEQUENCE: 324
cttggcaccc gagaattcca agttttagta caatatgttc ttgcggta 48

<210> SEQ ID NO 325
<211> LENGTH: 41
<212> TYPE: DNA
<213> ORGANISM: Artificial sequence
<220> FEATURE:
<223> OTHER INFORMATION: Synthesized

<400> SEQUENCE: 325
cttggcaccc gagaattcca cattgtgtaa aaggggcagc a 41

<210> SEQ ID NO 326
<211> LENGTH: 46
<212> TYPE: DNA
<213> ORGANISM: Artificial sequence
<220> FEATURE:
<223> OTHER INFORMATION: Synthesized

<400> SEQUENCE: 326
cttggcaccc gagaattcca tgtttacaca gaaaggcctt gtaagt 46

<210> SEQ ID NO 327
<211> LENGTH: 39
<212> TYPE: DNA
<213> ORGANISM: Artificial sequence
<220> FEATURE:
<223> OTHER INFORMATION: Synthesized

<400> SEQUENCE: 327
cttggcaccc gagaattcca catgcggcga tggccaata 39

<210> SEQ ID NO 328
<211> LENGTH: 45
<212> TYPE: DNA
<213> ORGANISM: Artificial sequence
<220> FEATURE:
<223> OTHER INFORMATION: Synthesized

<400> SEQUENCE: 328
cttggcaccc gagaattcca ttccgagaga ggacaacaga gttgt 45

<210> SEQ ID NO 329
<211> LENGTH: 41
<212> TYPE: DNA
<213> ORGANISM: Artificial sequence
<220> FEATURE:
<223> OTHER INFORMATION: Synthesized

<400> SEQUENCE: 329
cttggcaccc gagaattcca gacgggacgt aaacaaagga c 41

<210> SEQ ID NO 330
<211> LENGTH: 40
<212> TYPE: DNA
<213> ORGANISM: Artificial sequence
<220> FEATURE:
<223> OTHER INFORMATION: Synthesized

<400> SEQUENCE: 330
cttggcaccc gagaattcca ggagaccgcg taaagagagg 40

<210> SEQ ID NO 331
<211> LENGTH: 40
<212> TYPE: DNA
<213> ORGANISM: Artificial sequence
<220> FEATURE:
<223> OTHER INFORMATION: Synthesized

<400> SEQUENCE: 331
cttggcaccc gagaattcca gtgcagaggt gaagcgaagt 40

<210> SEQ ID NO 332
<211> LENGTH: 45
<212> TYPE: DNA
<213> ORGANISM: Artificial sequence
<220> FEATURE:
<223> OTHER INFORMATION: Synthesized

<400> SEQUENCE: 332
cttggcaccc gagaattcca tccaagagtc ctcttatgta agacc 45

<210> SEQ ID NO 333
<211> LENGTH: 43
<212> TYPE: DNA
<213> ORGANISM: Artificial sequence
<220> FEATURE:
<223> OTHER INFORMATION: Synthesized

<400> SEQUENCE: 333
cttggcaccc gagaattcca caactcctcc cagtccttaa aca 43

<210> SEQ ID NO 334
<211> LENGTH: 40
<212> TYPE: DNA
<213> ORGANISM: Artificial sequence
<220> FEATURE:
<223> OTHER INFORMATION: Synthesized

<400> SEQUENCE: 334
cttggcaccc gagaattcca ggtgctggtg aacagaccaa 40

<210> SEQ ID NO 335

<211> LENGTH: 42
<212> TYPE: DNA
<213> ORGANISM: Artificial sequence
<220> FEATURE:
<223> OTHER INFORMATION: Synthesized

<400> SEQUENCE: 335
cttggcaccc gagaattcca cttggaggct tgaacagtag ga 42

<210> SEQ ID NO 336
<211> LENGTH: 45
<212> TYPE: DNA
<213> ORGANISM: Artificial sequence
<220> FEATURE:
<223> OTHER INFORMATION: Synthesized

<400> SEQUENCE: 336
cttggcaccc gagaattcca aattctttat acgggtcaat gtcca 45

<210> SEQ ID NO 337
<211> LENGTH: 38
<212> TYPE: DNA
<213> ORGANISM: Artificial sequence
<220> FEATURE:
<223> OTHER INFORMATION: Synthesized

<400> SEQUENCE: 337
cttggcaccc gagaattcca cagaggcggt gtcgagga 38

<210> SEQ ID NO 338
<211> LENGTH: 40
<212> TYPE: DNA
<213> ORGANISM: Artificial sequence
<220> FEATURE:
<223> OTHER INFORMATION: Synthesized

<400> SEQUENCE: 338
cttggcaccc gagaattcca acacagaaca gcttgcctga 40

<210> SEQ ID NO 339
<211> LENGTH: 44
<212> TYPE: DNA
<213> ORGANISM: Artificial sequence
<220> FEATURE:
<223> OTHER INFORMATION: Synthesized

<400> SEQUENCE: 339
cttggcaccc gagaattcca ctgggtcttc caaattactt ccca 44

<210> SEQ ID NO 340
<211> LENGTH: 46
<212> TYPE: DNA
<213> ORGANISM: Artificial sequence
<220> FEATURE:
<223> OTHER INFORMATION: Synthesized

<400> SEQUENCE: 340
cttggcaccc gagaattcca gtttctcttc caaaggtaag acagga 46

<210> SEQ ID NO 341
<211> LENGTH: 43
<212> TYPE: DNA
<213> ORGANISM: Artificial sequence
<220> FEATURE:
<223> OTHER INFORMATION: Synthesized

<400> SEQUENCE: 341
cttggcaccc gagaattcca acctgcctct acgtctaaca aca 43

<210> SEQ ID NO 342
<211> LENGTH: 47
<212> TYPE: DNA
<213> ORGANISM: Artificial sequence
<220> FEATURE:
<223> OTHER INFORMATION: Synthesized

<400> SEQUENCE: 342
cttggcaccc gagaattcca ttgtgagtcc aagggatact aacattg 47

<210> SEQ ID NO 343
<211> LENGTH: 44
<212> TYPE: DNA
<213> ORGANISM: Artificial sequence
<220> FEATURE:
<223> OTHER INFORMATION: Synthesized

<400> SEQUENCE: 343
cttggcaccc gagaattcca gggagtttgc cactcaggat taaa 44

<210> SEQ ID NO 344
<211> LENGTH: 47
<212> TYPE: DNA
<213> ORGANISM: Artificial sequence
<220> FEATURE:
<223> OTHER INFORMATION: Synthesized

<400> SEQUENCE: 344
cttggcaccc gagaattcca gggcaaatac ttggtaaggt taggata 47

<210> SEQ ID NO 345
<211> LENGTH: 49
<212> TYPE: DNA
<213> ORGANISM: Artificial sequence
<220> FEATURE:
<223> OTHER INFORMATION: Synthesized

<400> SEQUENCE: 345
cttggcaccc gagaattcca ccttccacag agtatgtaaa taatgccta 49

<210> SEQ ID NO 346
<211> LENGTH: 42
<212> TYPE: DNA
<213> ORGANISM: Artificial sequence
<220> FEATURE:
<223> OTHER INFORMATION: Synthesized

<400> SEQUENCE: 346
cttggcaccc gagaattcca ctcccatgct gtagctcttg tt 42

<210> SEQ ID NO 347
<211> LENGTH: 40
<212> TYPE: DNA
<213> ORGANISM: Artificial sequence
<220> FEATURE:
<223> OTHER INFORMATION: Synthesized

<400> SEQUENCE: 347
cttggcaccc gagaattcca gctgggtcca actggtgatc 40

<210> SEQ ID NO 348
<211> LENGTH: 40
<212> TYPE: DNA

<213> ORGANISM: Artificial sequence
<220> FEATURE:
<223> OTHER INFORMATION: Synthesized

<400> SEQUENCE: 348
cttggcaccc gagaattcca ccccaaaaga ccaccgtgtg 40

<210> SEQ ID NO 349
<211> LENGTH: 41
<212> TYPE: DNA
<213> ORGANISM: Artificial sequence
<220> FEATURE:
<223> OTHER INFORMATION: Synthesized

<400> SEQUENCE: 349
cttggcaccc gagaattcca tcttcctgac tgccgattgg t 41

<210> SEQ ID NO 350
<211> LENGTH: 40
<212> TYPE: DNA
<213> ORGANISM: Artificial sequence
<220> FEATURE:
<223> OTHER INFORMATION: Synthesized

<400> SEQUENCE: 350
cttggcaccc gagaattcca caagaccttg ggcaggttcc 40

<210> SEQ ID NO 351
<211> LENGTH: 43
<212> TYPE: DNA
<213> ORGANISM: Artificial sequence
<220> FEATURE:
<223> OTHER INFORMATION: Synthesized

<400> SEQUENCE: 351
cttggcaccc gagaattcca attctaaggc ttcccgatac aga 43

<210> SEQ ID NO 352
<211> LENGTH: 46
<212> TYPE: DNA
<213> ORGANISM: Artificial sequence
<220> FEATURE:
<223> OTHER INFORMATION: Synthesized

<400> SEQUENCE: 352
cttggcaccc gagaattcca acgctggatc ttctaaatta ttaccc 46

<210> SEQ ID NO 353
<211> LENGTH: 43
<212> TYPE: DNA
<213> ORGANISM: Artificial sequence
<220> FEATURE:
<223> OTHER INFORMATION: Synthesized

<400> SEQUENCE: 353
cttggcaccc gagaattcca gatccactca cagtttccat agg 43

<210> SEQ ID NO 354
<211> LENGTH: 40
<212> TYPE: DNA
<213> ORGANISM: Artificial sequence
<220> FEATURE:
<223> OTHER INFORMATION: Synthesized

<400> SEQUENCE: 354
cttggcaccc gagaattcca cagcccaacc cttgtcctta 40

<210> SEQ ID NO 355
<211> LENGTH: 41
<212> TYPE: DNA
<213> ORGANISM: Artificial sequence
<220> FEATURE:
<223> OTHER INFORMATION: Synthesized

<400> SEQUENCE: 355
cttggcaccc gagaattcca tgggagcttc atctggacct g 41

<210> SEQ ID NO 356
<211> LENGTH: 41
<212> TYPE: DNA
<213> ORGANISM: Artificial sequence
<220> FEATURE:
<223> OTHER INFORMATION: Synthesized

<400> SEQUENCE: 356
cttggcaccc gagaattcca gaagggacag aagatgacag g 41

<210> SEQ ID NO 357
<211> LENGTH: 41
<212> TYPE: DNA
<213> ORGANISM: Artificial sequence
<220> FEATURE:
<223> OTHER INFORMATION: Synthesized

<400> SEQUENCE: 357
cttggcaccc gagaattcca caagaagccc agacggaaac c 41

<210> SEQ ID NO 358
<211> LENGTH: 38
<212> TYPE: DNA
<213> ORGANISM: Artificial sequence
<220> FEATURE:
<223> OTHER INFORMATION: Synthesized

<400> SEQUENCE: 358
cttggcaccc gagaattcca cccctcaggg caactgac 38

<210> SEQ ID NO 359
<211> LENGTH: 44
<212> TYPE: DNA
<213> ORGANISM: Artificial sequence
<220> FEATURE:
<223> OTHER INFORMATION: Synthesized

<400> SEQUENCE: 359
cttggcaccc gagaattcca gtgctgtgac tgcttgtaga tggc 44

<210> SEQ ID NO 360
<211> LENGTH: 41
<212> TYPE: DNA
<213> ORGANISM: Artificial sequence
<220> FEATURE:
<223> OTHER INFORMATION: Synthesized

<400> SEQUENCE: 360
cttggcaccc gagaattcca atctgagcag cgctcatggt g 41

<210> SEQ ID NO 361
<211> LENGTH: 38
<212> TYPE: DNA
<213> ORGANISM: Artificial sequence
<220> FEATURE:

<223> OTHER INFORMATION: Synthesized

<400> SEQUENCE: 361
cttggcaccc gagaattcca ccctgtcgtc tctccagc 38

<210> SEQ ID NO 362
<211> LENGTH: 47
<212> TYPE: DNA
<213> ORGANISM: Artificial sequence
<220> FEATURE:
<223> OTHER INFORMATION: Synthesized

<400> SEQUENCE: 362
cttggcaccc gagaattcca ctatgtcgaa aagtgtttct gtcatcc 47

<210> SEQ ID NO 363
<211> LENGTH: 41
<212> TYPE: DNA
<213> ORGANISM: Artificial sequence
<220> FEATURE:
<223> OTHER INFORMATION: Synthesized

<400> SEQUENCE: 363
cttggcaccc gagaattcca gagaccccag ttgcaaacca g 41

<210> SEQ ID NO 364
<211> LENGTH: 38
<212> TYPE: DNA
<213> ORGANISM: Artificial sequence
<220> FEATURE:
<223> OTHER INFORMATION: Synthesized

<400> SEQUENCE: 364
cttggcaccc gagaattcca tgggcctccg gttcatgc 38

<210> SEQ ID NO 365
<211> LENGTH: 38
<212> TYPE: DNA
<213> ORGANISM: Artificial sequence
<220> FEATURE:
<223> OTHER INFORMATION: Synthesized

<400> SEQUENCE: 365
cttggcaccc gagaattcca gtgcagggtg gcaagtgg 38

<210> SEQ ID NO 366
<211> LENGTH: 39
<212> TYPE: DNA
<213> ORGANISM: Artificial sequence
<220> FEATURE:
<223> OTHER INFORMATION: Synthesized

<400> SEQUENCE: 366
cttggcaccc gagaattcca gacaggcaca aacacgcac 39

<210> SEQ ID NO 367
<211> LENGTH: 44
<212> TYPE: DNA
<213> ORGANISM: Artificial sequence
<220> FEATURE:
<223> OTHER INFORMATION: Synthesized

<400> SEQUENCE: 367
cttggcaccc gagaattcca ttcttgcgga gattctcttc ctct 44

<210> SEQ ID NO 368
<211> LENGTH: 40
<212> TYPE: DNA
<213> ORGANISM: Artificial sequence
<220> FEATURE:
<223> OTHER INFORMATION: Synthesized

<400> SEQUENCE: 368
cttggcaccc gagaattcca cgcttcttgt cctgcttgct 40

<210> SEQ ID NO 369
<211> LENGTH: 46
<212> TYPE: DNA
<213> ORGANISM: Artificial sequence
<220> FEATURE:
<223> OTHER INFORMATION: Synthesized

<400> SEQUENCE: 369
cttggcaccc gagaattcca acttgataag aggtcccaag acttag 46

<210> SEQ ID NO 370
<211> LENGTH: 38
<212> TYPE: DNA
<213> ORGANISM: Artificial sequence
<220> FEATURE:
<223> OTHER INFORMATION: Synthesized

<400> SEQUENCE: 370
cttggcaccc gagaattcca agcctgggca tccttgag 38

<210> SEQ ID NO 371
<211> LENGTH: 38
<212> TYPE: DNA
<213> ORGANISM: Artificial sequence
<220> FEATURE:
<223> OTHER INFORMATION: Synthesized

<400> SEQUENCE: 371
cttggcaccc gagaattcca caggaagggg ctgaggtc 38

<210> SEQ ID NO 372
<211> LENGTH: 44
<212> TYPE: DNA
<213> ORGANISM: Artificial sequence
<220> FEATURE:
<223> OTHER INFORMATION: Synthesized

<400> SEQUENCE: 372
cttggcaccc gagaattcca catgagtttt ttatggcggg aggt 44

<210> SEQ ID NO 373
<211> LENGTH: 41
<212> TYPE: DNA
<213> ORGANISM: Artificial sequence
<220> FEATURE:
<223> OTHER INFORMATION: Synthesized

<400> SEQUENCE: 373
cttggcaccc gagaattcca cagtggggaa caagaagtgg a 41

<210> SEQ ID NO 374
<211> LENGTH: 34
<212> TYPE: DNA
<213> ORGANISM: Artificial sequence
<220> FEATURE:
<223> OTHER INFORMATION: Synthesized

<400> SEQUENCE: 374
cttggcaccc gagaaggacg cttctacacg cgaa 34

<210> SEQ ID NO 375
<211> LENGTH: 38
<212> TYPE: DNA
<213> ORGANISM: Artificial sequence
<220> FEATURE:
<223> OTHER INFORMATION: Synthesized

<400> SEQUENCE: 375
cttggcaccc gagaacacga acgaaaagga acatgtct 38

<210> SEQ ID NO 376
<211> LENGTH: 32
<212> TYPE: DNA
<213> ORGANISM: Artificial sequence
<220> FEATURE:
<223> OTHER INFORMATION: Synthesized

<400> SEQUENCE: 376
cttggcaccc gagaacgagt tcgcggcttc gg 32

<210> SEQ ID NO 377
<211> LENGTH: 31
<212> TYPE: DNA
<213> ORGANISM: Artificial sequence
<220> FEATURE:
<223> OTHER INFORMATION: Synthesized

<400> SEQUENCE: 377
cttggcaccc gagaacagca gcagcagcgg g 31

<210> SEQ ID NO 378
<211> LENGTH: 39
<212> TYPE: DNA
<213> ORGANISM: Artificial sequence
<220> FEATURE:
<223> OTHER INFORMATION: Synthesized

<400> SEQUENCE: 378
cttggcaccc gagaacaaac ccacagggta tctatcagg 39

<210> SEQ ID NO 379
<211> LENGTH: 32
<212> TYPE: DNA
<213> ORGANISM: Artificial sequence
<220> FEATURE:
<223> OTHER INFORMATION: Synthesized

<400> SEQUENCE: 379
cttggcaccc gagaagctgg gcgtgcacga tc 32

<210> SEQ ID NO 380
<211> LENGTH: 32
<212> TYPE: DNA
<213> ORGANISM: Artificial sequence
<220> FEATURE:
<223> OTHER INFORMATION: Synthesized

<400> SEQUENCE: 380
cttggcaccc gagaacctgg catcgctcac cc 32

<210> SEQ ID NO 381
<211> LENGTH: 32

<212> TYPE: DNA
<213> ORGANISM: Artificial sequence
<220> FEATURE:
<223> OTHER INFORMATION: Synthesized

<400> SEQUENCE: 381
cttggcaccc gagaagaccg tggggctgtg ag 32

<210> SEQ ID NO 382
<211> LENGTH: 35
<212> TYPE: DNA
<213> ORGANISM: Artificial sequence
<220> FEATURE:
<223> OTHER INFORMATION: Synthesized

<400> SEQUENCE: 382
cttggcaccc gagaactctt caagctcgga atgga 35

<210> SEQ ID NO 383
<211> LENGTH: 31
<212> TYPE: DNA
<213> ORGANISM: Artificial sequence
<220> FEATURE:
<223> OTHER INFORMATION: Synthesized

<400> SEQUENCE: 383
cttggcaccc gagaagccgc tgcagacgga t 31

<210> SEQ ID NO 384
<211> LENGTH: 33
<212> TYPE: DNA
<213> ORGANISM: Artificial sequence
<220> FEATURE:
<223> OTHER INFORMATION: Synthesized

<400> SEQUENCE: 384
cttggcaccc gagaaaggag gggtggaacc cag 33

<210> SEQ ID NO 385
<211> LENGTH: 40
<212> TYPE: DNA
<213> ORGANISM: Artificial sequence
<220> FEATURE:
<223> OTHER INFORMATION: Synthesized

<400> SEQUENCE: 385
cttggcaccc gagaatggga gaagaaaaaa acacacacac 40

<210> SEQ ID NO 386
<211> LENGTH: 35
<212> TYPE: DNA
<213> ORGANISM: Artificial sequence
<220> FEATURE:
<223> OTHER INFORMATION: Synthesized

<400> SEQUENCE: 386
cttggcaccc gagaatttcg cgggacaaaa accac 35

<210> SEQ ID NO 387
<211> LENGTH: 35
<212> TYPE: DNA
<213> ORGANISM: Artificial sequence
<220> FEATURE:
<223> OTHER INFORMATION: Synthesized

<400> SEQUENCE: 387
cttggcaccc gagaatctaa gtggccaggg cactg 35

<210> SEQ ID NO 388
<211> LENGTH: 33
<212> TYPE: DNA
<213> ORGANISM: Artificial sequence
<220> FEATURE:
<223> OTHER INFORMATION: Synthesized

<400> SEQUENCE: 388
cttggcaccc gagaagatca gggcaccttg ggc 33

<210> SEQ ID NO 389
<211> LENGTH: 32
<212> TYPE: DNA
<213> ORGANISM: Artificial sequence
<220> FEATURE:
<223> OTHER INFORMATION: Synthesized

<400> SEQUENCE: 389
cttggcaccc gagaactgca acaccgcgag cc 32

<210> SEQ ID NO 390
<211> LENGTH: 35
<212> TYPE: DNA
<213> ORGANISM: Artificial sequence
<220> FEATURE:
<223> OTHER INFORMATION: Synthesized

<400> SEQUENCE: 390
cttggcaccc gagaacgctc tgcttacgtg ctgac 35

<210> SEQ ID NO 391
<211> LENGTH: 31
<212> TYPE: DNA
<213> ORGANISM: Artificial sequence
<220> FEATURE:
<223> OTHER INFORMATION: Synthesized

<400> SEQUENCE: 391
cttggcaccc gagaagccgc tgcagcagtc c 31

<210> SEQ ID NO 392
<211> LENGTH: 32
<212> TYPE: DNA
<213> ORGANISM: Artificial sequence
<220> FEATURE:
<223> OTHER INFORMATION: Synthesized

<400> SEQUENCE: 392
cttggcaccc gagaacgctg ttgccttggc ga 32

<210> SEQ ID NO 393
<211> LENGTH: 33
<212> TYPE: DNA
<213> ORGANISM: Artificial sequence
<220> FEATURE:
<223> OTHER INFORMATION: Synthesized

<400> SEQUENCE: 393
cttggcaccc gagaagccag ttgtagggag cga 33

<210> SEQ ID NO 394
<211> LENGTH: 35
<212> TYPE: DNA
<213> ORGANISM: Artificial sequence
<220> FEATURE:
<223> OTHER INFORMATION: Synthesized

<400> SEQUENCE: 394
cttggcaccc gagaacgaag aggtagaggc cctcg 35

<210> SEQ ID NO 395
<211> LENGTH: 32
<212> TYPE: DNA
<213> ORGANISM: Artificial sequence
<220> FEATURE:
<223> OTHER INFORMATION: Synthesized

<400> SEQUENCE: 395
cttggcaccc gagaagtccg ggctgagcgg at 32

<210> SEQ ID NO 396
<211> LENGTH: 35
<212> TYPE: DNA
<213> ORGANISM: Artificial sequence
<220> FEATURE:
<223> OTHER INFORMATION: Synthesized

<400> SEQUENCE: 396
cttggcaccc gagaagccct ccaccacggt tctat 35

<210> SEQ ID NO 397
<211> LENGTH: 33
<212> TYPE: DNA
<213> ORGANISM: Artificial sequence
<220> FEATURE:
<223> OTHER INFORMATION: Synthesized

<400> SEQUENCE: 397
cttggcaccc gagaagagtt cctcccagcc agc 33

<210> SEQ ID NO 398
<211> LENGTH: 34
<212> TYPE: DNA
<213> ORGANISM: Artificial sequence
<220> FEATURE:
<223> OTHER INFORMATION: Synthesized

<400> SEQUENCE: 398
cttggcaccc gagaagggac tggagggcgt agag 34

<210> SEQ ID NO 399
<211> LENGTH: 31
<212> TYPE: DNA
<213> ORGANISM: Artificial sequence
<220> FEATURE:
<223> OTHER INFORMATION: Synthesized

<400> SEQUENCE: 399
cttggcaccc gagaaacttc gcggcggctc a 31

<210> SEQ ID NO 400
<211> LENGTH: 34
<212> TYPE: DNA
<213> ORGANISM: Artificial sequence
<220> FEATURE:
<223> OTHER INFORMATION: Synthesized

<400> SEQUENCE: 400
cttggcaccc gagaaccaac tccacggttc ctgc 34

<210> SEQ ID NO 401
<211> LENGTH: 32
<212> TYPE: DNA
<213> ORGANISM: Artificial sequence
<220> FEATURE:
<223> OTHER INFORMATION: Synthesized

<400> SEQUENCE: 401
cttggcaccc gagaatgagg gcgaaggcct ga 32

<210> SEQ ID NO 402
<211> LENGTH: 34
<212> TYPE: DNA
<213> ORGANISM: Artificial sequence
<220> FEATURE:
<223> OTHER INFORMATION: Synthesized

<400> SEQUENCE: 402
cttggcaccc gagaaggtgg taccgatgag agcg 34

<210> SEQ ID NO 403
<211> LENGTH: 58
<212> TYPE: DNA
<213> ORGANISM: Artificial sequence
<220> FEATURE:
<223> OTHER INFORMATION: Synthesized

<400> SEQUENCE: 403
aatgatacgg cgaccaccga gatctacact ctttccctac acgacgctct tccgatct 58

<210> SEQ ID NO 404
<211> LENGTH: 24
<212> TYPE: DNA
<213> ORGANISM: Artificial sequence
<220> FEATURE:
<223> OTHER INFORMATION: Synthesized

<400> SEQUENCE: 404
caagcagaag acggcatacg agat 24

<210> SEQ ID NO 405
<211> LENGTH: 27
<212> TYPE: DNA
<213> ORGANISM: Artificial sequence
<220> FEATURE:
<223> OTHER INFORMATION: Synthesized

<400> SEQUENCE: 405
gtctcgtggg ctcggagatg tgtataa 27

<210> SEQ ID NO 406
<211> LENGTH: 29
<212> TYPE: DNA
<213> ORGANISM: Artificial sequence
<220> FEATURE:
<223> OTHER INFORMATION: Synthesized

<400> SEQUENCE: 406
cagaaaggga agaatttttt gatgaaaca 29

<210> SEQ ID NO 407
<211> LENGTH: 30
<212> TYPE: DNA
<213> ORGANISM: Artificial sequence
<220> FEATURE:
<223> OTHER INFORMATION: Synthesized

<400> SEQUENCE: 407
ctcagaataa aaattctttg tgcaacctac 30

<210> SEQ ID NO 408
<211> LENGTH: 26
<212> TYPE: DNA
<213> ORGANISM: Artificial sequence
<220> FEATURE:
<223> OTHER INFORMATION: Synthesized

<400> SEQUENCE: 408
gctcaaagca atttctacac gagatc 26

<210> SEQ ID NO 409
<211> LENGTH: 25
<212> TYPE: DNA
<213> ORGANISM: Artificial sequence
<220> FEATURE:
<223> OTHER INFORMATION: Synthesized

<400> SEQUENCE: 409
gcaagaggct ttggagtatt tcatg 25

<210> SEQ ID NO 410
<211> LENGTH: 28
<212> TYPE: DNA
<213> ORGANISM: Artificial sequence
<220> FEATURE:
<223> OTHER INFORMATION: Synthesized

<400> SEQUENCE: 410
tgactgaata taaacttgtg gtagttgg 28

<210> SEQ ID NO 411
<211> LENGTH: 25
<212> TYPE: DNA
<213> ORGANISM: Artificial sequence
<220> FEATURE:
<223> OTHER INFORMATION: Synthesized

<400> SEQUENCE: 411
cctgtctctt ggatattctc gacac 25

<210> SEQ ID NO 412
<211> LENGTH: 30
<212> TYPE: DNA
<213> ORGANISM: Artificial sequence
<220> FEATURE:
<223> OTHER INFORMATION: Synthesized

<400> SEQUENCE: 412
gcaagaagtt atggaattcc ttttattgaa 30

<210> SEQ ID NO 413
<211> LENGTH: 26
<212> TYPE: DNA
<213> ORGANISM: Artificial sequence
<220> FEATURE:
<223> OTHER INFORMATION: Synthesized

<400> SEQUENCE: 413
ttgaggatct tgaaggaaac tgaatt 26

<210> SEQ ID NO 414

<211> LENGTH: 26
<212> TYPE: DNA
<213> ORGANISM: Artificial sequence
<220> FEATURE:
<223> OTHER INFORMATION: Synthesized

<400> SEQUENCE: 414
tgagaaagtt aaaattcccg tcgcta 26

<210> SEQ ID NO 415
<211> LENGTH: 21
<212> TYPE: DNA
<213> ORGANISM: Artificial sequence
<220> FEATURE:
<223> OTHER INFORMATION: Synthesized

<400> SEQUENCE: 415
ctccaggaag cctacgtgat g 21

<210> SEQ ID NO 416
<211> LENGTH: 18
<212> TYPE: DNA
<213> ORGANISM: Artificial sequence
<220> FEATURE:
<223> OTHER INFORMATION: Synthesized

<400> SEQUENCE: 416
acctccaccg tgcagctc 18

<210> SEQ ID NO 417
<211> LENGTH: 22
<212> TYPE: DNA
<213> ORGANISM: Artificial sequence
<220> FEATURE:
<223> OTHER INFORMATION: Synthesized

<400> SEQUENCE: 417
ccgcagcatg tcaagatcac ag 22

<210> SEQ ID NO 418
<211> LENGTH: 22
<212> TYPE: DNA
<213> ORGANISM: Artificial sequence
<220> FEATURE:
<223> OTHER INFORMATION: Synthesized

<400> SEQUENCE: 418
ggttgaaaaa gccgaaggtc ac 22

<210> SEQ ID NO 419
<211> LENGTH: 30
<212> TYPE: DNA
<213> ORGANISM: Artificial sequence
<220> FEATURE:
<223> OTHER INFORMATION: Synthesized

<400> SEQUENCE: 419
catttgactt taccttatca atgtctcgaa 30

<210> SEQ ID NO 420
<211> LENGTH: 28
<212> TYPE: DNA
<213> ORGANISM: Artificial sequence
<220> FEATURE:
<223> OTHER INFORMATION: Synthesized

<400> SEQUENCE: 420
acttacctgt gactccatag aaaatctt 28

<210> SEQ ID NO 421
<211> LENGTH: 23
<212> TYPE: DNA
<213> ORGANISM: Artificial sequence
<220> FEATURE:
<223> OTHER INFORMATION: Synthesized

<400> SEQUENCE: 421
caatccattt ttgttgtcca gcc 23

<210> SEQ ID NO 422
<211> LENGTH: 22
<212> TYPE: DNA
<213> ORGANISM: Artificial sequence
<220> FEATURE:
<223> OTHER INFORMATION: Synthesized

<400> SEQUENCE: 422
tagctgtatc gtcaaggcac tc 22

<210> SEQ ID NO 423
<211> LENGTH: 21
<212> TYPE: DNA
<213> ORGANISM: Artificial sequence
<220> FEATURE:
<223> OTHER INFORMATION: Synthesized

<400> SEQUENCE: 423
ggtccctcat tgcactgtac t 21

<210> SEQ ID NO 424
<211> LENGTH: 32
<212> TYPE: DNA
<213> ORGANISM: Artificial sequence
<220> FEATURE:
<223> OTHER INFORMATION: Synthesized

<400> SEQUENCE: 424
tgtatttatt tcagtgttac ttacctgtct tg 32

<210> SEQ ID NO 425
<211> LENGTH: 20
<212> TYPE: DNA
<213> ORGANISM: Artificial sequence
<220> FEATURE:
<223> OTHER INFORMATION: Synthesized

<400> SEQUENCE: 425
accttataca ccgtgccgaa 20

<210> SEQ ID NO 426
<211> LENGTH: 24
<212> TYPE: DNA
<213> ORGANISM: Artificial sequence
<220> FEATURE:
<223> OTHER INFORMATION: Synthesized

<400> SEQUENCE: 426
actcacatcg aggatttcct tgtt 24

<210> SEQ ID NO 427
<211> LENGTH: 19
<212> TYPE: DNA

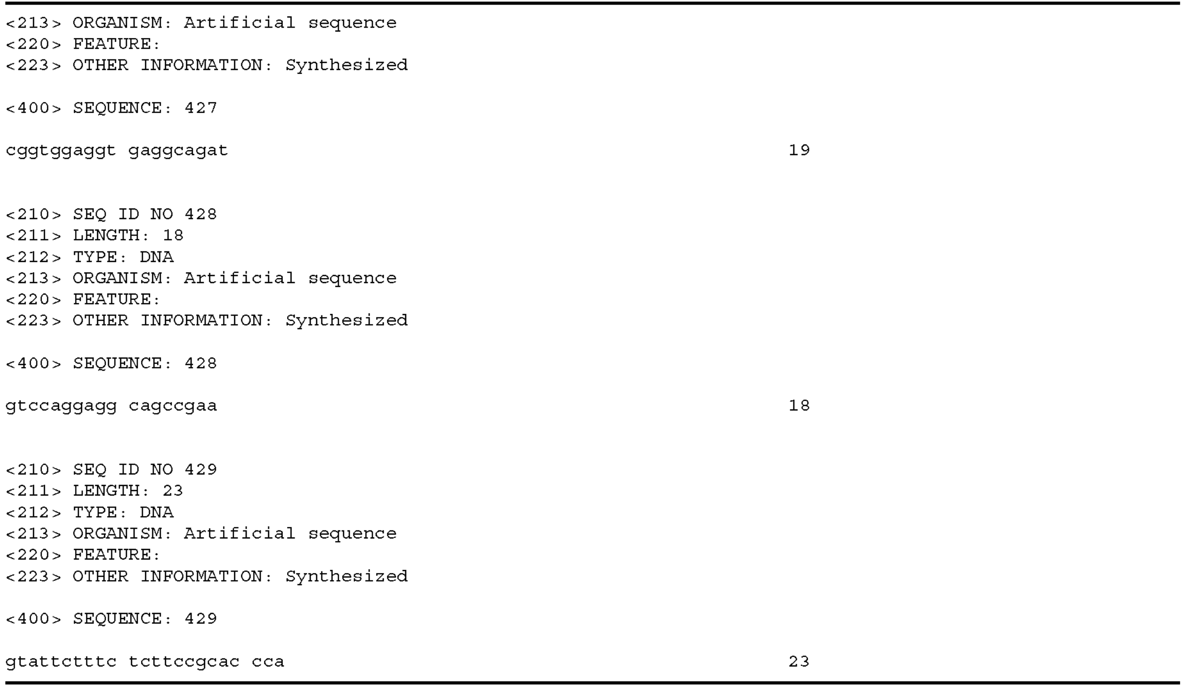

<213> ORGANISM: Artificial sequence
<220> FEATURE:
<223> OTHER INFORMATION: Synthesized

<400> SEQUENCE: 427
cggtggaggt gaggcagat 19

<210> SEQ ID NO 428
<211> LENGTH: 18
<212> TYPE: DNA
<213> ORGANISM: Artificial sequence
<220> FEATURE:
<223> OTHER INFORMATION: Synthesized

<400> SEQUENCE: 428
gtccaggagg cagccgaa 18

<210> SEQ ID NO 429
<211> LENGTH: 23
<212> TYPE: DNA
<213> ORGANISM: Artificial sequence
<220> FEATURE:
<223> OTHER INFORMATION: Synthesized

<400> SEQUENCE: 429
gtattctttc tcttccgcac cca 23

METHOD FOR DETECTING THE MUTATION AND METHYLATION OF TUMOR-SPECIFIC GENES IN ctDNA

RELATED APPLICATIONS

The present application is a U.S. National Phase of International Application Number PCT/CN2020/120560 filed Oct. 13, 2020, and claims priority to Chinese Application Number 201910983038.8 filed Oct. 16, 2019.

INCORPORATION BY REFERENCE

The sequence listing provided in the file entitled Amended_SQL_20220412.txt, which is an ASCII text file that was created on Mar. 20, 2026, and which comprises 79,916 bytes, is hereby incorporated by reference in its entirety.

TECHNICAL FIELD

The present invention belongs to the field of biomedicine, and specifically relates to a method for detecting the mutation and methylation of tumor-specific genes in ctDNA.

BACKGROUND

Circulating tumor DNA (ctDNA) is derived from DNA fragments produced by apoptosis, necrosis or secretion of tumor cells, and contains the same genetic variants and epigenetic modifications as tumor tissue DNA, such as point mutation, gene rearrangement, fusion, copy number variation, methylation modification, etc. The detection of ctDNA can be used in early cancer screening, diagnosis and staging, guidance of targeted drugs, efficacy evaluation, recurrence monitoring and other aspects. Combining the information of mutation and methylation of tumor-specific genes carried by ctDNA will help to improve the sensitivity and specificity of detection and detect cancer traces earlier, which is of great significance for early tumor screening.

The existing genetic variant detection and methylation detection need to follow different technical routes. The detection of ctDNA gene mutations is essentially the detection of low-frequency mutations due to the low proportion of ctDNA in cfDNA. The existing technologies are divided into two categories: 1) The PCR-based hot spot mutation detection method, which usually detects one or several hot spot mutation or known mutation, but cannot detect complex mutations such as gene fusion, and cannot detect unknown mutations, and of which the coverage is small; 2) Capture sequencing method: suitable for multiple target detection, including complex mutations, but the capture kits are generally expensive, complicated to operate, and time-consuming. In the application process, it is necessary to select a suitable detection method according to the number and characteristics of the target. The advantages of ctDNA methylation markers are clustered distribution, higher specificity than genetic variant, tissue-specific, being able to trace the origin of tumors, a larger number of markers, and higher sensitivity can be achieved; the detection methods thereof include: 1) Methylation PCR, due to the loss of DNA and the reduction of sequence diversity caused by the bisulfite conversion step, it is difficult for this method to achieve multiple target detection; 2) Methylation capture based on probe hybridization: it can cover 8%-13% of CpG sites and detect a large number of markers at the same time, but it is limited by the limited starting amount of ctDNA, and after bisulfite treatment, the genome sequence richness decreases, and it is not easy to guarantee the probe specificity; 3) MspI digestion-based RRBS (Reduced representation bisulfite sequencing, RRBS), the CpG sites it covers are determined by the enzyme cleavage site "CCGG", accounting for about 8%-10% of the CpG sites, and the recognition of methylated C bases also depends on bisulfite conversion. The methylation sites detected by RRBS are concentrated in CpG islands and promoter regions, and the cost is low. The above three methods have limited methylation PCR coverage sites; methylation capture can cover more sites and is more stable than RRBS data; RRBS has the lowest cost and can also cover a large number of methylation sites. In the application process, it is necessary to choose the method according to the number and characteristics of the target.

Currently, there is no simple, low-cost and reliable solution to simultaneously detect two important tumor-specific markers, genetic variant and methylation in ctDNA. There are mainly the following difficulties: 1) The amount of ctDNA samples obtained from one blood draw is limited, usually only enough to support 1-2 tests. As a result, ctDNA clinical testing is usually single-platform and disposable, and it is difficult to achieve mutation detection and methylation detection in one sample at the same time; in particular, methylation detection technology that relies on bisulfite conversion will cause more DNA loss during processing. 2) The bisulfite conversion step of the methylation detection technology will cause the DNA sequence fail to present most of the mutation information, and the loss of information carried by this part of the DNA may lead to reduce the sensitivity of low-frequency mutation detection. 3) In clinical testing, it is often necessary to judge the goals and plans of subsequent testing based on the results of the first testing, which requires redrawing blood in subsequent testing and prolonging the testing period; in addition, ctDNA-related clinical testing or research often needs to compare the pros and cons of multiple techniques, which requires specimens of several times the normal amount of blood drawn, which is usually unacceptable to patients. 4) Whether the PCR method or the capture method, the noise mutation generated during the amplification process will seriously interfere with the detection of low-frequency mutations in ctDNA, resulting in false positive results and misleading the diagnosis and treatment of patients. 5) The ctDNA mutation content is low, and it is easy for contamination to occur during the operation, resulting in false positive results.

SUMMARY OF THE INVENTION

The purpose of the present invention is to detect the mutation and/or methylation of multiple tumor-specific genes in ctDNA simultaneously.

The present invention first protects a method for constructing a sequencing library, comprising the following steps sequentially:

(1) taking a DNA sample and digesting it with a methylation-sensitive restriction endonuclease;

(2) the DNA sample digested in step (1) is subjected to end repair and adding A treatment at the 3' end sequentially;

(3) ligating the DNA sample processed in step (2) with the adapter in the adapter mixture, and obtaining a library after PCR amplification;

the adapter mixture consists of n adapters;

each adapter is formed by an upstream primer A and a downstream primer A to form a partial double-stranded structure; the upstream primer A has a sequencing adapter A, a random tag, an anchor sequence A and a base T at the end; the downstream primer A has an anchor sequence B and a sequencing adapter B; the partial double-stranded structure is formed by the reverse complementation of the anchor sequence A and the anchor sequence B;

the sequencing adapter A and sequencing adapter B are corresponding sequencing adapters selected according to different sequencing platforms;

the random tag is a random base of 8-14 bp (eg 8-10 bp, 10-14 bp, 8 bp, 10 bp or 14 bp);

the anchor sequence A has a length of 12-20 bp (eg 12-16 bp, 16-20 bp, 12 bp, 16 bp or 20 bp), and has ≤3 consecutive repeating bases;

the n adapters use n different anchor sequences A(s), and the four bases in each anchor sequence A are balanced, and the number of mismatched bases ≥3;

n is any natural number ≥8.

Usually, the adapter used for constructing a library is formed by annealing two sequences, with a "Y"-shaped structure, and the part of complementary pairing between the two sequences (ie, anchor sequence A and anchor sequence B) is called the anchor sequence. The anchor sequence can serve as a sequence-fixed built-in tag for labeling the original template molecule.

The anchor sequence does not interact with other parts of the primer (eg, to form hairpins, dimers, etc.).

The upstream primer A can include a sequencing adapter A, a random tag, an anchor sequence A and a base T sequentially from the 5' end.

The upstream primer A can be composed of a sequencing adapter A, a random tag, an anchor sequence A and a base T sequentially from the 5' end.

The downstream primer A can include an anchor sequence B and a sequencing adapter B sequentially from the 5' end.

The downstream primer A can be composed of an anchor sequence B and a sequencing adapter B sequentially from the 5' end.

The "four bases in each anchor sequence A are balanced", that is, A, T, C and G are evenly distributed.

The "number of mismatched bases ≥3" can be that the adapter mixture contains n anchor sequences A(s), and there are at least 3 differences in the bases between each anchor sequence A. The difference can be different positions or different sequences.

The DNA sample is a genomic DNA, cDNA, ct DNA or cf DNA sample.

The n may be 12 specifically.

The random tag can be random bases of 8 bp specifically.

The length of the anchor sequence A may specifically be 12 bp.

When n=12, the nucleotide sequence of the anchor sequence A can specifically be the 30th-41st positions from the 5' end of SEQ ID NO.1 in the sequence listing, the 30th-41st positions from the 5' end of SEQ ID NO.3 in the sequence listing, the 30th-41st positions from the 5' end of SEQ ID NO.5 in the sequence listing, the 30th-41st positions from the 5' end of SEQ ID NO.7 in the sequence listing, the 30th-41st positions from the 5' end of SEQ ID NO.9 in the sequence listing, the 30th-41st positions from the 5' end of SEQ ID NO.11 in the sequence listing, the 30th-41st positions from the 5' end of SEQ ID NO.13 in the sequence listing, the 30th-41st positions from the 5' end of SEQ ID NO.15 in the sequence listing, the 30th-41st positions from the 5' end of SEQ ID NO.17 in the sequence listing, the 30th-41st positions from the 5' end of SEQ ID NO.19 in the sequence listing, the 30th-41st positions from the 5' end of SEQ ID NO.21 in the sequence listing, the 30th-41st positions from the 5' end of SEQ ID NO.23 in the sequence listing, respectively.

The sequencing adapter A may specifically be a sequencing adapter from the Truseq sequencing kit from Illumina. The sequencing adapter A can be specifically shown as the 1-29th positions from the 5' end of SEQ ID NO.1 in the sequence listing.

The sequencing adapter B may specifically be a sequencing adapter from the nextera sequencing kit from Illumina. The sequencing adapter B can be specifically shown as the 13-41th positions from the 5' end of SEQ ID NO.2 in the sequence listing.

When n=12, the 12 adapters are as follows:

the adapter 1 can be obtained by forming a partial double-stranded structure from the single-stranded DNA molecule shown in SEQ ID NO.1 and the single-stranded DNA molecule shown in SEQ ID NO.2 in the sequence listing; the adapter 2 can be obtained by forming a partial double-stranded structure from the single-stranded DNA molecule shown in SEQ ID NO.3 and the single-stranded DNA molecule shown in SEQ ID NO.4 in the sequence listing; the adapter 3 can be obtained by forming a partial double-stranded structure from the single-stranded DNA molecule shown in SEQ ID NO.5 and the single-stranded DNA molecule shown in SEQ ID NO.6 in the sequence listing; the adapter 4 can be obtained by forming a partial double-stranded structure from the single-stranded DNA molecule shown in SEQ ID NO.7 and the single-stranded DNA molecule shown in SEQ ID NO.8 in the sequence listing; the adapter 5 can be obtained by forming a partial double-stranded structure from the single-stranded DNA molecule shown in SEQ ID NO.9 and the single-stranded DNA molecule shown in SEQ ID NO.10 in the sequence listing; the adapter 6 can be obtained by forming a partial double-stranded structure from the single-stranded DNA molecule shown in SEQ ID NO.11 and the single-stranded DNA molecule shown in SEQ ID NO.12 in the sequence listing; the adapter 7 can be obtained by forming a partial double-stranded structure from the single-stranded DNA molecule shown in SEQ ID NO.13 and the single-stranded DNA molecule shown in SEQ ID NO.14 in the sequence listing; the adapter 8 can be obtained by forming a partial double-stranded structure from the single-stranded DNA molecule shown in SEQ ID NO.15 and the single-stranded DNA molecule shown in SEQ ID NO.16 in the sequence listing; the adapter 9 can be obtained by forming a partial double-stranded structure from the single-stranded DNA molecule shown in SEQ ID NO.17 and the single-stranded DNA molecule shown in SEQ ID NO.18 in the sequence listing; the adapter 10 can be obtained by forming a partial double-stranded structure from the single-stranded DNA molecule shown in SEQ ID NO.19 and the single-stranded DNA molecule shown in SEQ ID NO.20 in the sequence listing; the adapter 11 can be obtained by forming a partial double-stranded structure from the single-stranded DNA molecule shown in SEQ ID NO.21 and the single-stranded DNA molecule shown in SEQ ID NO.22 in the sequence listing; the adapter 12 can be obtained by forming a partial double-stranded structure from the single-stranded DNA molecule shown in SEQ ID NO.23 and the single-stranded DNA molecule shown in SEQ ID NO.24 in the sequence listing.

The adapter can be obtained by annealing the upstream primer A and the downstream primer A.

In the adapter mixture, each adapter may be mixed in equimolar amount.

The method may further include the step of amplifying the library obtained in step (3). The primers for the amplification are designed according to the sequence of the adapter, that is, at least a sequence of the primer for amplification must be completely consistent with a certain sequence of the adapter. The primer pair used for the amplification can be specifically composed of two single-stranded DNA molecules shown in SEQ ID NO.25 and SEQ ID NO.26 in the sequence listing.

The single-stranded DNA molecule shown in SEQ ID NO.25 of the sequence listing is the 1st to 19th positions of the sequencing adapter A from the 5' end.

The single-stranded DNA molecule shown in SEQ ID NO.26 of the sequence listing is the 1st to 22nd positions of the sequencing adapter B from the 3' end.

The present invention also protects the DNA library constructed by the above-mentioned method.

The present invention also protects a kit for constructing a sequencing library, which can include any of the above-mentioned adapter mixtures and a methylation-sensitive restriction endonuclease.

The kit for constructing a sequencing library can be composed of any of the above-mentioned adapter mixtures and a methylation-sensitive restriction endonuclease.

The present invention also protects a kit for detecting tumor mutation and/or methylation in DNA samples, comprising any of the above-mentioned adapter mixtures and primer combinations; the primer combinations include primer set I, primer set II, primer set III, primer set IV, primer set V, primer set VI, primer set VII and primer set VIII;

- each primer in the primer set I and the primer set II is a specific primer designed according to the region related to tumor mutation, and its function is to locate at a specific position in the genome to achieve PCR enrichment of the target region; the primer set I and the primer set II are respectively used to detect the mutation sites of the DNA positive strand and the negative strand;
- each primer in the primer set III and the primer set IV is a specific primer designed according to the tumor-specific hypermethylated region, and its function is to locate at a specific position in the genome to achieve PCR enrichment of the target region; the primer set III and the primer set IV are respectively used to detect the methylation sites of the DNA positive strand and the negative strand;
- each primer in the primer set V, the primer set VI, the primer set VII and the primer set VIII includes a adapter sequence and a specific sequence, and the specific sequence is used for further enrichment of the target region;
- in the primer set V and the primer set I, the two primers designed for the same mutation site are “nested” relationship;
- in the primer set VI and the primer set II, the two primers designed for the same mutation site are “nested” relationship;
- in the primer set VII and the primer set III, the two primers designed for the same methylation site are “nested” relationship;
- in the primer set VIII and the primer set IV, the two primers designed for the same methylation site are “nested” relationship.

The “specific primers designed according to regions related to tumor mutation” may specifically be designed corresponding gene-specific primers according to regions of tumor-specific gene mutations (such as point mutation, insertion-deletion mutation, HBV integration and other mutation forms).

The “specific primers designed according to the tumor-specific hypermethylated regions” may specifically be designed corresponding gene-specific primers according to the tumor-specific methylated regions.

In the kit, the tumor can be a liver malignant tumor, that is, hepatocellular carcinoma.

The region associated with hepatocellular carcinoma mutation may specifically be the relevant regions of high-frequency mutation genes (TP53, CTNNB1, AXIN1, TERT) in hepatocellular carcinoma, and HBV integration hotspot regions.

In any of the above-mentioned kits, the primer set I includes 78 single-stranded DNA molecules, and the nucleotide sequences of the 78 single-stranded DNA molecules are shown as SEQ ID NO.28 to 105 in the sequence listing sequentially. The primer set II includes 82 single-stranded DNA molecules, and the nucleotide sequences of the 82 single-stranded DNA molecules are shown as SEQ ID NO.106 to 187 in the sequence listing sequentially. The primer set III includes 14 single-stranded DNA molecules, and the nucleotide sequences of the 14 single-stranded DNA molecules are shown as SEQ ID NO.188 to 201 in the sequence listing sequentially. The primer set IV includes 15 single-stranded DNA molecules, and the nucleotide sequences of the 15 single-stranded DNA molecules are shown as SEQ ID NO.202 to 216 in the sequence listing sequentially. The primer set V includes 75 single-stranded DNA molecules, and the 75 single-stranded DNA molecules sequentially include the nucleotide sequences shown as SEQ ID NO.220 to SEQ ID NO.294 of the sequence listing from the 16th position from the 5' end to the 3' end. The primer set VI includes 79 single-stranded DNA molecules, and the 79 single-stranded DNA molecules sequentially include the nucleotide sequences shown as SEQ ID NO.295 to SEQ ID NO.373 of the sequence listing from the 16th position from the 5' end to the 3' end. The primer set VII includes 14 single-stranded DNA molecules, and the 14 single-stranded DNA molecules sequentially include the nucleotide sequences shown as SEQ ID NO.374 to SEQ ID NO.387 of the sequence listing from the 16th position from the 5' end to the 3' end. The primer set VIII includes 15 single-stranded DNA molecules, and the 15 single-stranded DNA molecules sequentially include the nucleotide sequences shown as SEQ ID NO.388 to SEQ ID NO.402 of the sequence listing from the 16th position from the 5' end to the 3' end.

The nucleotide sequences of the 75 single-stranded DNA molecules in the primer set V can be shown as SEQ ID NO.220 to SEQ ID NO.294 in the sequence listing sequentially. The nucleotide sequences of the 79 single-stranded DNA molecules in the primer set VI can be shown as SEQ ID NO.295 to SEQ ID NO.373 in the sequence listing sequentially. The nucleotide sequences of the 14 single-stranded DNA molecules in the primer set VII can be shown as SEQ ID NO.374 to SEQ ID NO.387 in the sequence listing sequentially. The nucleotide sequences of the 15 single-stranded DNA molecules in the primer set VIII can be shown as SEQ ID NO.388 to SEQ ID NO.402 in the sequence listing sequentially.

The primer set I can specifically consist of the 78 single-stranded DNA molecules.

The primer set II can specifically consist of the 82 single-stranded DNA molecules.

The primer set III can specifically consist of the 14 single-stranded DNA molecules.

The primer set IV can specifically consist of the 15 single-stranded DNA molecules.

The primer set V can specifically consist of the 75 single-stranded DNA molecules.

The primer set VI can specifically consist of the 79 single-stranded DNA molecules.

The primer set VII can specifically consist of the 14 single-stranded DNA molecules.

The primer set VIII can specifically consist of the 15 single-stranded DNA molecules.

Any of the above-mentioned kits may specifically be composed of any of the above-mentioned adapter mixtures and the above-mentioned primer combinations.

Any of the above-mentioned primer combinations can specifically consist of the primer set I, the primer set II, the primer set III, the primer set IV, the primer set V, the primer set VI, the primer set VII and the primer set VIII.

Any of the above-mentioned kits may further include reagents for DNA extraction, reagents for DNA library construction, reagents for library purification, reagents for library capture, and other materials used for library construction.

The present invention also protects any one of the above-mentioned primer combinations. The primer combination can be used to detect tumor mutation and/or methylation in DNA samples.

The present invention also protects S1) or S2) or S3):

S1) application of any one of the above-mentioned primer combinations in the preparation of a kit for detecting tumor mutation and/or methylation in DNA samples;

S2) application of any one of the above-mentioned primer combinations in distinguishing blood samples from tumor patients and blood samples from non-tumor patients;

S3) application of any one of the above-mentioned kits in distinguishing blood samples from tumor patients and blood samples from non-tumor patients.

In the above application, the tumor may be a liver malignant tumor, ie, hepatocellular carcinoma.

The present invention also protects a method for detecting target mutation and/or methylation in a DNA sample, may comprising the following steps:

(1) constructing a library according to any of the methods described above;

(2) performing two rounds of nested PCR amplification to the library obtained in step (1), sequencing the product, and analyzing the occurrence of target mutation and/or methylation in the DNA sample according to the sequencing result;

in step (2), primer combination A is used to carry out the first round of PCR amplification;

primer combination A consists of upstream primer A and downstream primer combination A;

the upstream primer A is a library amplification primer used for library amplification in step (1);

the downstream primer combination A is a combination of Y primers designed according to X target sites; X and Y are both natural numbers greater than 1, and X≤Y;

using the product of the first round of PCR as a template, carrying out the second round of PCR amplification with primer combination B;

primer combination B consists of upstream primer B, downstream primer combination B and index primer;

the upstream primer B is a library amplification primer and the 3' end is the same as that of the upstream primer A, and is used for the amplification of the product of the first round of PCR;

the index primer includes a segment A for sequencing, an index sequence for distinguishing samples, and a segment B for sequencing from the 5' end;

the primer in the downstream primer combination B has the segment B and form a nested relationship with the primer detecting the same target site in the downstream primer combination A.

The nucleotide sequence of the upstream primer B can be shown as SEQ ID NO.217 in the sequence listing.

The index primer can specifically consist of the segment A, the index sequence and the segment B from the 5' end.

The nucleotide sequence of the segment A can be shown as SEQ ID NO.218 in the sequence Listing.

The nucleotide sequence of the segment B can be shown as SEQ ID NO.219 in the sequence listing.

The partial sequence of the upstream primer A is exactly the same as the sequence of the "sequencing adapter A of the upstream primer A of each adapter".

The upstream primer B is used to complete the adapter sequences of the library molecules, so that the amplification products can be directly sequenced. Partial nucleotide sequences of the upstream primer B and the upstream primer A (primer used in the first round of PCR amplification) are completely identical.

The nucleotide sequence of the upstream primer A can be specifically shown as SEQ ID NO.27 in the sequence listing.

The nucleotide sequence of the upstream primer B can be specifically shown as SEQ ID NO.188 in the sequence listing.

When the target mutation is hepatocellular carcinoma mutation, the downstream primer combination A is composed of any the primer set I and primer set II described above. The downstream primer combination B is composed of any the primer set V and primer set VI described above. The first round of PCR amplification is performed on the template using primer set I and primer set II, respectively. The product amplified with primer set I is used as template for the second round of amplification, and primer set V is used for amplification. The product amplified with primer set II is used as template for the second round of amplification, and primer set VI is used for amplification. Finally, equal volumes of amplification products are mixed.

When the target methylation is hepatocellular carcinoma methylation, the downstream primer combination A is composed of any primer set III and primer set IV described above. The downstream primer combination B is composed of any primer set VII and primer set VIII described above.

The first round of PCR amplification is performed on the template using primer set III and primer set IV, respectively. The product amplified with primer set III is used as the template for the second round of amplification, and primer set VII is used for amplification. The product amplified with primer set IV is used as the template for the second round of amplification, and primer set VIII is used for amplification. Finally, equal volumes of amplification products are mixed.

In the above method, the method for analyzing the target mutation in the DNA sample can be: DNA molecules whose sequencing data meet the criterion A are traced back to a molecular cluster; the molecular clusters which meet the criterion B are labeled as a pair of duplex molecular clusters; for a mutation, if the following (a1) or (a2) is satisfied, the mutation is a true mutation from the original DNA sample: (a1) supported by at least one pair of duplex molecular clusters (this condition only supports the capture of sequencing data, not applicable to race data); (a2) supported by at least 4 molecular clusters; criterion A means satisfying ①, ② and ③ at the same time; ① the length of the DNA inserts is the same and the sequences are the same except for the mutation sites; ② the random tag sequences are the same; ③ the anchor sequences are the same; criterion B means satisfying both ④ and ⑤; ④ the length of the DNA inserts is the same and the sequences are the same except for the mutation sites; ⑤ the anchor sequences at both ends of the molecular cluster are the same but in opposite positions.

In the above method, the method for analyzing methylation in the DNA sample can be: the DNA molecules whose sequencing data meet the criterion C are labeled as a cluster, and the number of clusters whose ends are the restriction sites of interest is calculated respectively, and recorded as unmethylated fragments; the number of all the clusters whose amplified fragments reach or exceed the first restriction site is calculated, and recorded as the total number of fragments; the average methylation level of the corresponding region is calculated according to the number of two fragments; the methylation level of the region=(1−the number of unmethylated fragments/the total number of fragments)×100%; criterion C means satisfying ⑥, ⑦ and ⑧ at the same time; ⑥ the random tag sequences are the same; ⑦ the anchor sequences are the same; ⑧ the length of the DNA inserts is the same and the sequences are the same except for the mutation sites.

The DNA inserts mentioned above specifically refer to the amplified DNA fragments other than the adapters.

The present invention also protects a method for detecting multiple target mutations and/or methylation in a DNA sample, may comprising the following steps:

(1) constructing a library according to any of the methods described above;

(2) enriching and sequencing the target region of the library of step (1), and analyzing the occurrence of target mutation and/or methylation in the DNA sample according to the sequencing result.

In the above method, the method for analyzing the target mutation in the DNA sample can be: DNA molecules whose sequencing data meet the criterion A are traced back to a molecular cluster; the molecular clusters which meet the criterion B are labeled as a pair of duplex molecular clusters; for a mutation, if the following (a1) or (a2) is satisfied, the mutation is a true mutation from the original DNA sample: (a1) supported by at least one pair of duplex molecular clusters; (a2) supported by at least 4 molecular clusters; criterion A means satisfying ①, ② and ③ at the same time; ① the length of the DNA inserts is the same and the sequences are the same except for the mutation sites; ② the random tag sequences are the same; ③ the anchor sequences are the same; criterion B means satisfying both ④ and ⑤; ④ the length of the DNA inserts is the same and the sequences are the same except for the mutation sites; ⑤ the anchor sequences at both ends of the molecular cluster are the same but in opposite positions.

In the above method, the method for analyzing methylation in the DNA sample can be: the DNA molecules whose sequencing data meet the criterion C are labeled as a cluster, and the number of clusters whose ends are the restriction sites of interest is calculated respectively, and recorded as unmethylated fragments; the number of all the clusters whose amplified fragments reach or exceed the first restriction site is calculated, and recorded as the total number of fragments; the average methylation level of the corresponding region is calculated according to the number of two fragments; the methylation level of the region=(1−the number of unmethylated fragments/the total number of fragments)×100%; criterion C means satisfying ⑥, ⑦ and ⑧ at the same time; ⑥ the random tag sequences are the same; ⑦ the anchor sequences are the same; ⑧ the length of the DNA inserts is the same and the sequences are the same except for the mutation sites.

The target region enrichment can be carried out by using a commercially available target capture kit (eg Agilent sureselect XT target capture kit, Agilent5190-8646), replacing the primer pair in the last step of PCR amplification with the primer pair consisting of primer A and primer B. The nucleotide sequence of the primer A can be shown as SEQ ID NO.403 in the sequence listing. The primer B may include segment A, an index sequence and segment B. The primer B can specifically consist of the segment A, the index sequence and the segment B. The nucleotide sequence of the segment A can be shown as SEQ ID NO.404 in the sequence listing. The nucleotide sequence of the segment B can be shown as SEQ ID NO.405 in the sequence listing.

In any of the above methods, the target mutation and/or methylation may be tumor mutation and/or methylation. The tumor may be a liver malignancy, i.e. hepatocellular carcinoma.

In the above, usually multiple libraries of different samples are mixed together for sequencing, and the index sequences are used to mark different samples. After the sequencing is completed, the total sequencing data is split according to different index sequences. The design principles for Index are basically similar to those for anchor sequences described earlier.

In the above, DNA samples are digested with methylation-sensitive restriction endonucleases to form DNA fragments (at this time, both ends of the DNA fragments form sticky ends, and the nucleotide sequence of the single-stranded part of the ends is the breakpoint sequence.); the DNA fragments are end-repaired and then ligated with adapters (the 5' end and the 3' end are each ligated with an adapter, which may be the same adapter or the opposite adapter), and for the DNA molecule at this time, the DNA fragment between the two adapters is the DNA insertion fragment.

The present invention provides a method which can simultaneously detect the mutation (including point mutation, insertion deletion mutation, HBV integration and other mutation forms) and/or methylation of tumor-specific genes of ctDNA in one sample. Not only the sample size requirement is small, but the MC library prepared by this method can support 10-20 subsequent detections. The results of each test can represent the mutation status of all the original ctDNA specimens and the methylation modification status of the region covered by the restriction sites, without reducing the sensitivity and specificity. The library constructed by this method can be used for PCR hotspots detection and capture sequencing at the same time; the added DNA barcode can effectively filter out false positive results and achieve high specificity sequencing based on duplex. At the same time, the library construction method is not only applicable to cfDNA samples, but also to genomic DNA or cDNA samples. The present invention has important clinical significance for early tumor screening, disease tracking, efficacy evaluation, prognosis prediction and the like, and has great application value.

EMBODIMENTS

Figure 1:
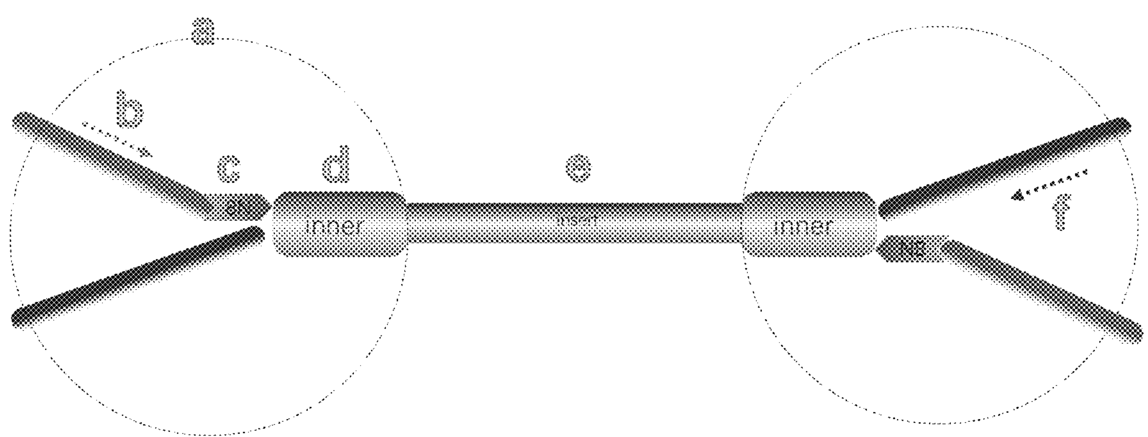
FIG. 1 is a schematic diagram of the adapter and primer architecture.

The following examples facilitate a better understanding of the present invention, but do not limit the present invention.

The experimental methods in the following examples, unless otherwise specified, are all conventional methods.

The experimental materials used in the following examples, unless otherwise specified, are all purchased from conventional biochemical reagent stores.

The quantitative experiments in the following examples are all set to repeat the experiment three times, and the results are averaged.

The TE buffer in the following examples is the product of ThermoFisher Company, the product catalog number is 12090015.

In the following examples, patients with hepatocellular carcinoma gave informed consent to the content of the present invention.

Example 1. Construction of MC Library

1. Methylation-Sensitive Restriction Endonuclease Digestion 5-40 ng of cfDNA was taken to configure the reaction system as shown in Table 1, and then enzyme digestion treatment was performed in the PCR machine according to the procedure in Table 2 to obtain the enzyme digestion product (stored at 4° C.).

Both Restriction Enzyme and Restriction Enzyme 10× Buffer are products of ThermoFisher Company. Restriction Enzyme and Restriction Enzyme 10× Buffer can be selected according to different target regions to be tested, and the selection criterion is that the region to be tested contains at least one restriction enzyme cleavage site of the methylation-sensitive restriction enzyme.

TABLE 1

| Reaction system | |
|---|---|
| Composition | Volume |
| cfDNA | 16.8 µl |
| Restriction Enzyme 10 × Buffer | 2 µl |
| Acetylated BSA (concentration: 10 µg/µl) | 0.2 µl |
| Restriction Enzyme (concentration: 10 U/µl) | 1 µl |
| total volume | 20 µl |

TABLE 2

| Reaction Procedure | |
|---|---|
| Temperature | Time |
| 37° C. | 2 h |

2. Purification of Enzyme Digestion Products

The enzyme digestion product obtained in step 1 was purified and enriched to obtain a purified product with Apostle MiniMax™ high-efficiency free DNA enrichment and isolation kit (standard version) (a product of Apostle Company, product catalog number is A17622-50)

3. Blunt End Repair and Adding a Treatment of Purified Products

The purified product obtained in step 2 was taken to configure the reaction system as shown in Table 3, and then end repair and adding A treatment at the 3' end in a PCR machine were performed according to the reaction procedure in Table 4 to obtain a reaction product (stored at 4° C.).

TABLE 3

| Reaction system | |
|---|---|
| Composition | Volume |
| Purified product | 50 µl |
| End Repair & A-Tailing Buffer (KAPA KK8505) | 7 µl |
| End Repair & A-Tailing Enzyme Mix (KAPA KK8505) | 3 µl |
| total volume | 60 µl |

TABLE 4

| reaction procedure | |
|---|---|
| Temperature | Time |
| 20° C. | 30 min |
| 65° C. | 30 min |

4. Ligation the Reaction Product to the Adapter

The reaction system was configured according to Table 5, and the reaction was carried out at 20° C. for 15 min to obtain a ligation product (stored at 4° C.).

TABLE 5

| Reaction system | |
|---|---|
| Composition | volume |
| Reaction product obtained in step 3 | 60 µl |
| Adapter Mix (50 µM) | 1.5 µl |
| DNase/RNase-Free Water | 8.5 µl |
| Ligation Buffer (KAPA KK8505) | 30 µl |
| DNA Ligase (KAPA KK8505) | 10 µl |
| Total volume | 110 µl |

Adapter sequence information is shown in Table 6.

The single-stranded DNA molecules in Table 6 were dissolved with TE buffer and diluted to a concentration of 100 µM, respectively. Two single-stranded DNA molecules in the same group were mixed in equal volumes (50 µl each), and then annealed (annealing program: 95° C., 15 min; 25° C., 2 h) to obtain 12 sets of DNA solutions. The 12 sets of DNA solutions were mixed in equal volumes to obtain Adapter Mix.

TABLE 6

| Adapter sequence information | | | |
|---|---|---|---|
| Group | Number | Name | Nucleotide sequence (5'-3') |
| 1 | 1 | R21_F | GACACGACGCTCTTCCGATCTNNNNNNNNCCACTAGTAGCC**T** (SEQ ID NO. 1) |
| | 2 | R21_R | GGCTACTAGTGGCTGTCTCTTATACACATCTCCGAGCCCAC (SEQ ID NO. 2) |
| 2 | 3 | R22_F | GACACGACGCTCTTCCGATCTNNNNNNNNGGACTGTGTCGG**T** (SEQ ID NO. 3) |
| | 4 | R22_R | CCGACACAGTCCCTGTCTCTTATACACATCTCCGAGCCCAC (SEQ ID NO. 4) |
| 3 | 5 | R23_F | GACACGACGCTCTTCCGATCTNNNNNNNNGGTACTGACAGG**T** (SEQ ID NO. 5) |
| | 6 | R23_R | CCTGTCAGTACCCTGTCTCTTATACACATCTCCGAGCCCAC (SEQ ID NO. 6) |
| 4 | 7 | R24 F | GACACGACGCTCTTCCGATCTNNNNNNNNCCTAGTACAGCC**T** (SEQ ID NO. 7) |
| | 8 | R24_R | GGCTGTACTAGGCTGTCTCTTATACACATCTCCGAGCCCAC (SEQ ID NO. 8) |
| 5 | 9 | R25_F | GACACGACGCTCTTCCGATCTNNNNNNNNGGTAGTCAGAGG**T** (SEQ ID NO. 9) |
| | 10 | R25_R | CCTCTGACTACCCTGTCTCTTATACACATCTCCGAGCCCAC (SEQ ID NO. 10) |
| 6 | 11 | R26_F | GACACGACGCTCTTCCGATCTNNNNNNNNTTCTCACGTGTT**T** (SEQ ID NO. 11) |
| | 12 | R26_R | AACACGTGAGAACTGTCTCTTATACACATCTCCGAGCCCAC (SEQ ID NO. 12) |
| 7 | 13 | R27_F | GACACGACGCTCTTCCGATCTNNNNNNNNAACTCCACGTAA**T** (SEQ ID NO. 13) |
| | 14 | R27_R | TTACGTGGAGTTCTGTCTCTTATACACATCTCCGAGCCCAC (SEQ ID NO. 14) |
| 8 | 15 | R28_F | GACACGACGCTCTTCCGATCTNNNNNNNNTTCTCGAGAATT**T** (SEQ ID NO. 15) |
| | 16 | R28_R | AATTCTCGAGAACTGTCTCTTATACACATCTCCGAGCCCAC (SEQ ID NO. 16) |
| 9 | 17 | R29_F | GACACGACGCTCTTCCGATCTNNNNNNNNAAACTCTTCCAA**T** (SEQ ID NO. 17) |
| | 18 | R29_R | TTGGAAGAGTTTCTGTCTCTTATACACATCTCCGAGCCCAC (SEQ ID NO. 18) |
| 10 | 19 | R30_F | GACACGACGCTCTTCCGATCTNNNNNNNNTTGGAACGTCTT**T** (SEQ ID NO. 19) |
| | 20 | R30_R | AAGACGTTCCAACTGTCTCTTATACACATCTCCGAGCCCAC (SEQ ID NO. 20) |
| 11 | 21 | R31_F | GACACGACGCTCTTCCGATCTNNNNNNNNCCGGACTCCTCC**T** (SEQ ID NO. 21) |
| | 22 | R31_R | GGAGGAGTCCGGCTGTCTCTTATACACATCTCCGAGCCCAC (SEQ ID NO. 22) |
| 12 | 23 | R32_F | GACACGACGCTCTTCCGATCTNNNNNNNNAAGGAGGAGTAA**T** (SEQ ID NO. 23) |
| | 24 | R32_R | TTACTCCTCCTTCTGTCTCTTATACACATCTCCGAGCCCAC (SEQ ID NO. 24) |

In Table 6, 8 Ns represent an 8-bp random tag. In practical applications, the random tag length can be 8-14 bp.

Underlined indicates the 12-bp anchor sequence. In the upstream sequence (the ones containing "F" in the name are upstream sequences) and downstream sequence (the ones containing "R" in the name are the downstream sequences) of each group, the underlined parts are reverse complementary, and the upstream and downstream sequences can be brought together to form a linker by annealing. At the same time, the anchor sequence can serve as a sequence-fixed built-in tag for labeling the original template molecule. In practical applications, the length of the anchor sequence can be 12-20 bp, with no more than 3 consecutive repeating bases, and it cannot interact with other parts of the primer (such as forming hairpin structures, dimers, etc.); in the 12 groups, the bases are balanced at each position (ie, A, T, C, and G are evenly distributed), and the number of mismatched bases ≥3 (that is, each anchor sequence differs by at least 3 bases, the difference can be different in position or order).

The bold T at the end in the upstream sequence is complementary to the "A" added at the end of the original molecule for TA ligation.

In the upstream sequence, positions 1 to 21 from the 5' end (from the Truseq sequencing kit of Illumina) is sequencing primer binding sequence, and positions 1 to 19 from the 5' end is the part of the library amplification primer.

In the downstream sequence, the non-underlined part (from the nextera sequencing kit of Illumina) is the sequencing primer binding sequence, and the positions 1 to 22 from the 3' end is the part of the library amplification primer.

Table 6 contains a total of 12 sets of linkers, which can form 12×12=144 kinds of marker combinations, combined with the sequence information of the molecule itself, which is enough to distinguish all molecules in the original sample.

In practical applications, the number of groups can be appropriately increased (increased synthesis cost) or decreased (with slightly weaker differentiation effect).

The structure of the ligation product is shown in FIG. 1. Wherein, a is the linker part, b and f are the library amplification primers respectively, c is the 8 bp random tag (indicated by 8 Ns in Table 6), d is the 12 bp anchor sequence (indicated by the underline in Table 6), and e is the insert fragment (cfDNA).

5. Purification of Ligation Products 110-220 μl (i.e. 1-2 times the volume) of AMPure XP magnetic beads (Beckman A63880) was added to the ligation product obtained in step 4, mixed by vortexing, placed at room temperature for 10 min, and adsorption on magnetic stand was kept for 5 min. After the solution was clear, the supernatant was discarded, then 200 μl of 80% (volume percent) ethanol aqueous solution was added to wash twice, and the supernatant was discarded. After the ethanol was air-dried, 30 μl of DNase/RNase-Free Water was added, mixed by vortexing, placed at room temperature for 10 min, and adsorption on magnetic stand was kept for 5 min. The supernatant solution was pipetted into a PCR tube as a PCR template.

6. Library Amplification and Purification (1) The PCR template obtained in step 5 was taken to configure the reaction system according to Table 7, and PCR amplification was performed according to Table 8 to obtain PCR amplification products (stored at 4° C.).

TABLE 7

| Reaction system | |
|---|---|
| Composition | volume |
| HIFI (KAPA KK8505) | 35 μl |
| MC_F (33 μM) | 2.5 μl |
| MC_R (33 μM) | 2.5 μl |
| PCR template | 30 μl |
| Total volume | 70 μl |

In Table 7 the rimer information is as follows:

```
MC_F (SEQ ID NO. 25):
5'-GACACGACGCTCTTCCGAT-3';

MC_R (SEQ ID NO. 26):
5'-GTGGGCTCGGAGATGTGTATAA-3'.
```

TABLE 8

| reaction procedure | | |
|---|---|---|
| Temperature | Time | Number of cycles |
| 98° C. | 45 s | |
| 98° C. | 15 s | 7-10 cycles |
| 57-60° C. | 30 s | |
| 72° C. | 30 s | |
| 72° C. | 5 min | |

(2) 70-140 μl (i.e. 1-2 times the volume) of AMPure XP magnetic beads was added to the PCR amplification product obtained in step (1), mixed by vortexing, placed at room temperature for 10 min, and adsorption on magnetic stand was kept for 5 min. After the solution was clear, the supernatant was discarded, then 200 μl of 80% (volume percent) ethanol aqueous solution was added to wash twice, and the supernatant was discarded. After the ethanol was air-dried, 100 μl of DNase/RNase-Free Water was added, mixed by vortexing, placed at room temperature for 10 min, and adsorption on magnetic stand was kept for 5 min. The supernatant solution was pipetted to obtain the product (stored at −20° C.). The product is the MC library that can be stored for a long time and used repeatedly.

After testing, the MC library could support 10-20 subsequent tests, and the results of each test could represent the mutation status of all the original samples and the methylation modification status in the areas covered by the restriction sites, without reducing the sensitivity and specificity. At the same time, the library construction method is not only applicable to cfDNA samples, but also to genomic DNA or cDNA samples.

Figure 2:
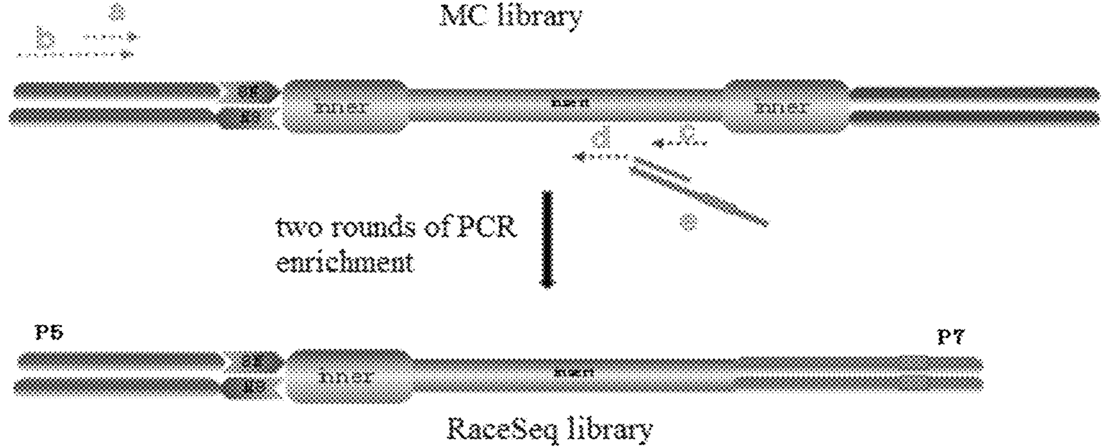
FIG. 2 is a schematic diagram of RaceSeq target enrichment and library construction.

Example 2. RaceSeq Target Region Enrichment and Construction of a Sequencing Library As shown in FIG. 2, primers designed for the relevant regions of high-frequency mutation genes (TP53, CTNNB1, AXIN1, TERT) in Chinese hepatocellular carcinoma, HBV integration hotspot regions and HCC-specific hypermethylated regions (EMX1, LRRC4, BDH1, etc.) were used in combination with fixed primers to perform two rounds of PCR amplification on the MC library. The amplified product was the sequencing library.

In FIG. 2, a is the upstream primer of the first round of library amplification; b is the upstream primer of the second round of library amplification; c is the downstream primer library of the first round of library amplification, which is used for enrichment of specific target sequences; d is the downstream primer library of the second round of library amplification, which is used for the enrichment of specific target sequences; e is the index primer, which is used to add the index sequence.

1. 300 ng of the MC library prepared by Example 1 was taken, divided into two parts, to configure the reaction system of Table 9 (one was added to GSP1A mix and the other was added to GSP1B mix). The first round of PCR amplification was carried out according to the reaction procedure of Table 11, and the first round of amplification products were obtained (a total of two first-round amplification products were obtained, one was the amplification product of the GSP1A mix, and the other was the amplification product of the GSP1B mix).

TABLE 9

| Reaction system | |
|---|---|
| Composition | volume |
| Hifi (KAPA KK8505) | 15 μl |
| upstream primer1355 | 3 μl |
| GSP1A mix/GSP1B mix | 2 μl |
| MC library | 10 μl |
| total volume | 30 μl |

In Table 9, the primer information is as follows:

```
Upstream primer 1355 (SEQ ID NO. 27):
5'-TCTTTCCCTACACGACGCTCTTCCGAT-3'.
```

GSP1A mix: each primer in the primer pool GSP1A in Table 10 was dissolved and diluted to a concentration of 100 μM with TE buffer, then mixed in equal volumes, and diluted to 0.3 μM with TE buffer. The primers in primer pool GSP1A were used to amplify the positive strand of the template.

GSP1B mix: each primer in the primer pool GSP1B in Table 10 was dissolved and diluted to a concentration of 100 μM with TE buffer, then mixed in equal volumes, and diluted to 0.3 μM with TE buffer. The primers in primer pool GSP1B were used to amplify the negative strand of the template.

In the primer pool GSP1A and the primer pool GSP1B, the primers with the same number (that is, the last four digits of the primer number are the same) detect the same mutation site from both positive and negative directions, and simultaneous use can maximize the enrichment of original molecular information.

TABLE 10

| Primer Information | | | |
|---|---|---|---|
| Gene Name | Primer Pool | Primer number | SEQ ID NO. Nucleotide sequence (5'-3') |
| AXIN1 | GSP1A | HA1009 | TGTATTAGGGTGCAGCGCTC (SEQ ID NO. 28) |
| AXIN1 | GSP1A | HA1010 | CGCTCGGATCTGGACCTG (SEQ ID NO. 29) |
| AXIN1 | GSP1A | HA1011 | TGGAGCCCTGTGACTCGAA (SEQ ID NO. 30) |
| AXIN1 | GSP1A | HA1012 | GTGACCAGGACATGGATGAGG (SEQ ID NO. 31) |
| AXIN1 | GSP1A | HA1013 | TCCTCCAGTAGACGGTACAGC (SEQ ID NO. 32) |
| AXIN1 | GSP1A | HA1014 | TGCTGCTTGTCCCCACAC (SEQ ID NO. 33) |
| AXIN1 | GSP1A | HA1015 | CCGCTTGGCACCACTTCC (SEQ ID NO. 34) |
| AXIN1 | GSP1A | HA1016 | GGCACGGGAAGCACGTAC (SEQ ID NO. 35) |
| AXIN1 | GSP1A | HA1017 | CCTTGCAGTGGGAAGGTG (SEQ ID NO. 36) |
| CTNNB1 | GSP1A | HA1018 | GACAGAAAAGCGGCTGTTAGTCA (SEQ ID NO. 37) |
| TERT | GSP1A | HA1019 | CCGACCTCAGCTACAGCAT (SEQ ID NO. 38) |
| TERT | GSP1A | HA1020 | ACTTGAGCAACCCGGAGTCTG (SEQ ID NO. 39) |
| TERT | GSP1A | HA1021 | CTCCTAGCTCTGCAGTCCGA (SEQ ID NO. 40) |
| TERT | GSP1A | HA1022 | GCGCCTGGCTCCATTTCC (SEQ ID NO. 41) |
| TERT | GSP1A | HA1023 | CGCCTGAGAACCTGCAAAGAG (SEQ ID NO. 42) |
| TERT | GSP1A | HA1024 | GTCCAGGGAGCAATGCGT (SEQ ID NO. 43) |
| TERT | GSP1A | HA1025 | CGGGTTACCCCACAGCCTA (SEQ ID NO. 44) |
| TERT | GSP1A | HA1026 | GGCTCCCAGTGGATTCGC (SEQ ID NO. 45) |
| TERT | GSP1A | HA1027 | GTCCTGCCCCTTCACCTT (SEQ ID NO. 46) |
| HBV-C | GSP1A | HA1028 | CCGACTACTGCCTCACCCATAT (SEQ ID NO. 47) |
| HBV-C | GSP1A | HA1029 | GGGTTTTTCTTGTTGACAAGAATCCT (SEQ ID NO. 48) |
| HBV-C | GSP1A | HA1030 | CCAACCTCCAATCACTCACCAA (SEQ ID NO. 49) |
| HBV-C | GSP1A | HA1031 | GGCGTTTTATCATATTCCTCTTCATCCT (SEQ ID NO. 50) |
| HBV-C | GSP1A | HA1032 | CTACTTCCAGGAACATCAACTACCAG (SEQ ID NO. 51) |
| HBV-C | GSP1A | HA1033 | CTGCACTTGTATTCCCATCCCAT (SEQ ID NO. 52) |
| HBV-C | GSP1A | HA1034 | TCAGTTTACTAGTGCCATTTGTTCAGT (SEQ ID NO. 53) |
| HBV-C | GSP1A | HA1035 | TACAACATCTTGAGTCCCTTTTTACCTC (SEQ ID NO. 54) |
| HBV-C | GSP1A | HA1036 | AGAATTGTGGGTCTTTTGGGCTT (SEQ ID NO. 55) |
| HBV-C | GSP1A | HA1037 | TGTAAACAATATCTGAACCTTTACCCTGTT (SEQ ID NO. 56) |
| HBV-C | GSP1A | HA1038 | GCATGCGTGGAACCTTTGTG (SEQ ID NO. 57) |
| HBV-C | GSP1A | HA1039 | AACTCTGTTGTCCTCTCTCGGAA (SEQ ID NO. 58) |
| HBV-C | GSP1A | HA1040 | CTGAATCCCGCGGACGAC (SEQ ID NO. 59) |

TABLE 10-continued

| Primer Information | | | |
|---|---|---|---|
| Gene Name | Primer Pool | Primer number | SEQ ID NO. Nucleotide sequence (5'-3') |
| HBV-C | GSP1A | HA1041 | CCGTCTGTGCCTTCTCATCTG (SEQ ID NO. 60) |
| HBV-C | GSP1A | HA1042 | GAACGCCCACCAGGTCTTG (SEQ ID NO. 61) |
| HBV-C | GSP1A | HA1043 | CCTTGAGGCGTACTTCAAAGACTG (SEQ ID NO. 62) |
| HBV-C | GSP1A | HA1044 | GGAGGCTGTAGGCATAAATTGGT (SEQ ID NO. 63) |
| HBV-C | GSP1A | HA1045 | GTCCTACTGTTCAAGCCTCCAA (SEQ ID NO. 64) |
| HBV-C | GSP1A | HA1046 | GGGCTTCTGTGGAGTTACTCTC (SEQ ID NO. 65) |
| HBV-C | GSP1A | HA1047 | TTGTATCGGGAGGCCTTAGAGT (SEQ ID NO. 66) |
| HBV-C | GSP1A | HA1048 | TTCTGTGTTGGGGTGAGTTGA (SEQ ID NO. 67) |
| HBV-C | GSP1A | HA1049 | CCAGCATCCAGGGAATTAGTAGTCA (SEQ ID NO. 68) |
| HBV-C | GSP1A | HA1050 | TTCCTGTCTTACCTTTGGAAGAGAAAC (SEQ ID NO. 69) |
| HBV-C | GSP1A | HA1051 | CCGGAAACTACTGTTGTTAGACGTA (SEQ ID NO. 70) |
| HBV-C | GSP1A | HA1052 | CGTCGCAGAAGATCTCAATCTCG (SEQ ID NO. 71) |
| HBV-C | GSP1A | HA1053 | AAACTCCCTCCTTTCCTAACATTCATTT (SEQ ID NO. 72) |
| HBV-C | GSP1A | HA1054 | TATGCCTGCTAGGTTCTATCCTAACC (SEQ ID NO. 73) |
| HBV-C | GSP1A | HA1055 | GGCATTATTTACATACTCTGTGGAAGG (SEQ ID NO. 74) |
| HBV-C | GSP1A | HA1056 | GTTGGTCTTCCAAACCTCGACA (SEQ ID NO. 75) |
| HBV-C | GSP1A | HA1057 | TTCAACCCCAACAAGGATCACT (SEQ ID NO. 76) |
| HBV-C | GSP1A | HA1058 | TTCCACCAATCGGCAGTCAG (SEQ ID NO. 77) |
| HBV-B | GSP1A | HA1059 | GCCCTGCTCAGAATACTGTCT (SEQ ID NO. 78) |
| HBV-B | GSP1A | HA1060 | ATTCGCAGTCCCAAATCTCC (SEQ ID NO. 79) |
| HBV-B | GSP1A | HA1061 | CATCTTCCTCTGCATCCTGCT (SEQ ID NO. 80) |
| HBV-B | GSP1A | HA1062 | TTCCAGGATCATCAACCACCAG (SEQ ID NO. 81) |
| HBV-B | GSP1A | HA1063 | GTCCCTTTATGCCGCTGT (SEQ ID NO. 82) |
| HBV-B | GSP1A | HA1064 | ACCCTTATAAAGAATTTGGAGCTACTGTG (SEQ ID NO. 83) |
| HBV-B | GSP1A | HA1065 | CTCCTGAACATTGCTCACCTCA (SEQ ID NO. 84) |
| TP53 | GSP1A | HA1071 | AGACTGCCTTCCGGGTCA (SEQ ID NO. 85) |
| TP53 | GSP1A | HA1072 | CCTGTGGGAAGCGAAAATTCCA (SEQ ID NO. 86) |
| TP53 | GSP1A | HA1073 | ACCTGGTCCTCTGACTGCT (SEQ ID NO. 87) |
| TP53 | GSP1A | HA1074 | AAGCAATGGATGATTTGATGCTGT (SEQ ID NO. 88) |
| TP53 | GSP1A | HA1075 | GACCCAGGTCCAGATGAAGC (SEQ ID NO. 89) |
| TP53 | GSP1A | HA1076 | TCCTGGCCCCTGTCATCT (SEQ ID NO. 90) |
| TP53 | GSP1A | HA1077 | GTGCCCTGACTTTCAACTCTGT (SEQ ID NO. 91) |
| TP53 | GSP1A | HA1078 | CAACTGGCCAAGACCTGC (SEQ ID NO. 92) |
| TP53 | GSP1A | HA1079 | CGCCATGGCCATCTACAAGC (SEQ ID NO. 93) |
| TP53 | GSP1A | HA1080 | GGTCCCCAGGCCTCTGAT (SEQ ID NO. 94) |
| TP53 | GSP1A | HA1081 | GAGTGGAAGGAAATTTGCGTGT (SEQ ID NO. 95) |
| TP53 | GSP1A | HA1082 | GCACTGGCCTCATCTTGGG (SEQ ID NO. 96) |
| TP53 | GSP1A | HA1083 | CCATCCACTACAACTACATGTGTAAC (SEQ ID NO. 97) |

TABLE 10-continued

| Primer Information | | | |
|---|---|---|---|
| Gene Name | Primer Pool | Primer number | SEQ ID NO. Nucleotide sequence (5'-3') |
| TP53 | GSP1A | HA1084 | TTTCCTTACTGCCTCTTGCTTCTC (SEQ ID NO. 98) |
| TP53 | GSP1A | HA1085 | GGGACGGAACAGCTTTGAGG (SEQ ID NO. 99) |
| TP53 | GSP1A | HA1086 | CACAGAGGAAGAGAATCTCCGCA (SEQ ID NO. 100) |
| TP53 | GSP1A | HA1087 | TGCCTCAGATTCACTTTTATCACCTT (SEQ ID NO. 101) |
| TP53 | GSP1A | HA1088 | CTCAGGTACTGTGTATATACTTACTTCTCC (SEQ ID NO. 102) |
| TP53 | GSP1A | HA1089 | CGTGAGCGCTTCGAGATGT (SEQ ID NO. 103) |
| TP53 | GSP1A | HA1090 | GTGATGTCATCTCTCCTCCCTG (SEQ ID NO. 104) |
| TP53 | GSP1A | HA1091 | TGAAGTCCAAAAAGGGTCAGTCTAC (SEQ ID NO. 105) |
| AXIN1 | GSP1B | HB1009 | GGGAGCATCTTCGGTGAAAC (SEQ ID NO. 106) |
| AXIN1 | GSP1B | HB1010 | CAGGCTTATCCCATCTTGGTCA (SEQ ID NO. 107) |
| AXIN1 | GSP1B | HB1011 | TTGGTGGCTGGCTTGGTC (SEQ ID NO. 108) |
| AXIN1 | GSP1B | HB1012 | GCTGTACCGTCTACTGGAGGA (SEQ ID NO. 109) |
| AXIN1 | GSP1B | HB1013 | GCTTGTTCTCCAGCTCTCGGA (SEQ ID NO. 110) |
| AXIN1 | GSP1B | HB1014 | GGGAAGTGGTGCCAAGCG (SEQ ID NO. 111) |
| AXIN1 | GSP1B | HB1015 | GCACACGCTGTACGTGCT (SEQ ID NO. 112) |
| AXIN1 | GSP1B | HB1016 | GCCTCCACCTGCTCCTTG (SEQ ID NO. 113) |
| AXIN1 | GSP1B | HB1017 | CCCTCAATGATCCACTGCATGA (SEQ ID NO. 114) |
| CTNNB1 | GSP1B | HB1018 | CTCATACAGGACTTGGGAGGTATC (SEQ ID NO. 115) |
| TERT | GSP1B | HB1019 | CACAACCGCAGGACAGCT (SEQ ID NO. 116) |
| TERT | GSP1B | HB1020 | CTCCAAGCCTCGGACTGC (SEQ ID NO. 117) |
| TERT | GSP1B | HB1021 | GCCTCACACCAGCCACAAC (SEQ ID NO. 118) |
| TERT | GSP1B | HB1022 | TCCCCACCATGAGCAAACCA (SEQ ID NO. 119) |
| TERT | GSP1B | HB1023 | GTGCCTCCCTGCAACACT (SEQ ID NO. 120) |
| TERT | GSP1B | HB1024 | GCACCACGAATGCCGGAC (SEQ ID NO. 121) |
| TERT | GSP1B | HB1025 | GTGGGGTAACCCGAGGGA (SEQ ID NO. 122) |
| TERT | GSP1B | HB1026 | GAGGAGGCGGAGCTGGAA (SEQ ID NO. 123) |
| TERT | GSP1B | HB1027 | AGCGCTGCCTGAAACTCG (SEQ ID NO. 124) |
| TERT | GSP1B | HB1028 | CGCACGAACGTGGCCAG (SEQ ID NO. 125) |
| HBV-C | GSP1B | HB1029 | GAGCCACCAGCAGGAAAGT (SEQ ID NO. 126) |
| HBV-C | GSP1B | HB1030 | CTAGGAATCCTGATGTTGTGCTCT (SEQ ID NO. 127) |
| HBV-C | GSP1B | HB1031 | CGCGAGTCTAGACTCTGTGGTA (SEQ ID NO. 128) |
| HBV-C | GSP1B | HB1032 | ATAGCCAGGACAAATTGGAGGACA (SEQ ID NO. 129) |
| HBV-C | GSP1B | HB1033 | GACAAACGGGCAACATACCTT (SEQ ID NO. 130) |
| HBV-C | GSP1B | HB1034 | CCGAAGGTTTTGTACAGCAACAA (SEQ ID NO. 131) |
| HBV-C | GSP1B | HB1035 | CTGAGCCAGGAGAAACGGACTGA (SEQ ID NO. 132) |
| HBV-C | GSP1B | HB1036 | GGGACTCAAGATGTTGTACAGACTTG (SEQ ID NO. 133) |
| HBV-C | GSP1B | HB1037 | GTTAAGGGAGTAGCCCCAACG (SEQ ID NO. 134) |

TABLE 10-continued

| Primer Information | | | |
|---|---|---|---|
| Gene Name | Primer Pool | Primer number | SEQ ID NO. Nucleotide sequence (5'-3') |
| HBV-C | GSP1B | HB1038 | CAGGCAGTTTTCGAAAACATTGCTT (SEQ ID NO. 135) |
| HBV-C | GSP1B | HB1039 | TTAAAGCAGGATAGCCACATTGTGTAA (SEQ ID NO. 136) |
| HBV-C | GSP1B | HB1040 | GGCAACAGGGTAAAGGTTCAGATAT (SEQ ID NO. 137) |
| HBV-C | GSP1B | HB1041 | CCACAAAGGTTCCACGCAT (SEQ ID NO. 138) |
| HBV-C | GSP1B | HB1042 | TGGAAAGGAAGTGTACTTCCGAGA (SEQ ID NO. 139) |
| HBV-C | GSP1B | HB1043 | GTCGTCCGCGGGATTCAG (SEQ ID NO. 140) |
| HBV-C | GSP1B | HB1044 | AAGGCACAGACGGGGAGA (SEQ ID NO. 141) |
| HBV-C | GSP1B | HB1045 | TCACGGTGGTCTCCATGC (SEQ ID NO. 142) |
| HBV-C | GSP1B | HB1046 | GGTCGTTGACATTGCTGAGAGT (SEQ ID NO. 143) |
| HBV-C | GSP1B | HB1047 | AACCTAATCTCCTCCCCCAACT (SEQ ID NO. 144) |
| HBV-C | GSP1B | HB1048 | GCAGAGGTGAAAAAGTTGCATGG (SEQ ID NO. 145) |
| HBV-C | GSP1B | HB1049 | CCACCCAAGGCACAGCTT (SEQ ID NO. 146) |
| HBV-C | GSP1B | HB1050 | ACTCCACAGAAGCCCCAA (SEQ ID NO. 147) |
| HBV-C | GSP1B | HB1051 | GCCTCCCGATACAAAGCAGA (SEQ ID NO. 148) |
| HBV-C | GSP1B | HB1052 | GATTCATCAACTCACCCCAACACA (SEQ ID NO. 149) |
| HBV-C | GSP1B | HB1053 | ACATAGCTGACTACTAATTCCCTGGAT (SEQ ID NO. 150) |
| HBV-C | GSP1B | HB1054 | ATCCACACTCCAAAAGACACCAAAT (SEQ ID NO. 151) |
| HBV-C | GSP1B | HB1055 | GCGAGGGAGTTCTTCTTCTAGG (SEQ ID NO. 152) |
| HBV-C | GSP1B | HB1056 | CAGTAAAGTTTCCCACCTTGTGAGT (SEQ ID NO. 153) |
| HBV-C | GSP1B | HB1057 | CCTCCTGTAAATGAATGTTAGGAAAGG (SEQ ID NO. 154) |
| HBV-C | GSP1B | HB1058 | GTTTAATGCCTTTATCCAAGGGCAAA (SEQ ID NO. 155) |
| HBV-C | GSP1B | HB1059 | CTCTTATATAGAATCCCAGCCTTCCAC (SEQ ID NO. 156) |
| HBV-C | GSP1B | HB1060 | CTTGTCGAGGTTTGGAAGACCA (SEQ ID NO. 157) |
| HBV-C | GSP1B | HB1061 | GTTTGAGTTGGCTCCGAACG (SEQ ID NO. 158) |
| HBV-C | GSP1B | HB1062 | CTGAGGGCTCCACCCCAA (SEQ ID NO. 159) |
| HBV-C | GSP1B | HB1063 | GTGAAGAGATGGGAGTAGGCTGT (SEQ ID NO. 160) |
| HBV-B | GSP1B | HB1064 | CCCATCTTTTTGTTTTGTGAGGGTTT (SEQ ID NO. 161) |
| HBV-B | GSP1B | HB1065 | TTAAAGCAGGATATCCACATTGCGTA (SEQ ID NO. 162) |
| HBV-B | GSP1B | HB1066 | TTGCTGAAAGTCCAAGAGTCCT (SEQ ID NO. 163) |
| HBV-B | GSP1B | HB1067 | GGTGAGCAATGTTCAGGAGATTC (SEQ ID NO. 164) |
| HBV-B | GSP1B | HB1068 | ACTACTAGATCCCTGGACGCTG (SEQ ID NO. 165) |
| HBV-B | GSP1B | HB1069 | GGTGGAGATAAGGGAGTAGGCTG (SEQ ID NO. 166) |
| TP53 | GSP1B | HB1071 | TGCCCTTCCAATGGATCCAC (SEQ ID NO. 167) |
| TP53 | GSP1B | HB1072 | GTCCCCAGCCCAACCCTT (SEQ ID NO. 168) |
| TP53 | GSP1B | HB1073 | CTCTGGCATTCTGGGAGCTT (SEQ ID NO. 169) |
| TP53 | GSP1B | HB1074 | TGGTAGGTTTTCTGGGAAGGGA (SEQ ID NO. 170) |
| TP53 | GSP1B | HB1075 | TGTCCCAGAATGCAAGAAGCC (SEQ ID NO. 171) |

TABLE 10-continued

| Primer Information | | | |
|---|---|---|---|
| Gene Name | Primer Pool | Primer number | SEQ ID NO. Nucleotide sequence (5'-3') |
| TP53 | GSP1B | HB1076 | GGCATTGAAGTCTCATGGAAGCCA (SEQ ID NO. 172) |
| TP53 | GSP1B | HB1077 | ACCTCCGTCATGTGCTGTGA (SEQ ID NO. 173) |
| TP53 | GSP1B | HB1078 | CTCACCATCGCTATCTGAGCA (SEQ ID NO. 174) |
| TP53 | GSP1B | HB1079 | GCAACCAGCCCTGTCGTC (SEQ ID NO. 175) |
| TP53 | GSP1B | HB1080 | GCACCACCACACTATGTCGAA (SEQ ID NO. 176) |
| TP53 | GSP1B | HB1081 | TTAACCCCTCCTCCCAGAGAC (SEQ ID NO. 177) |
| TP53 | GSP1B | HB1082 | TTCCAGTGTGATGATGGTGAGGAT (SEQ ID NO. 178) |
| TP53 | GSP1B | HB1083 | CAGCAGGCCAGTGTGCAG (SEQ ID NO. 179) |
| TP53 | GSP1B | HB1084 | CCGGTCTCTCCCAGGACA (SEQ ID NO. 180) |
| TP53 | GSP1B | HB1085 | GTGAGGCTCCCCTTTCTTGC (SEQ ID NO. 181) |
| TP53 | GSP1B | HB1086 | TGGTCTCCTCCACCGCTTC (SEQ ID NO. 182) |
| TP53 | GSP1B | HB1087 | GAAACTTTCCACTTGATAAGAGGTCC (SEQ ID NO. 183) |
| TP53 | GSP1B | HB1088 | CTCCCCCCTGGCTCCTTC (SEQ ID NO. 184) |
| TP53 | GSP1B | HB1089 | GGGGAGTAGGGCCAGGAAG (SEQ ID NO. 185) |
| TP53 | GSP1B | HB1090 | GCCCTTCTGTCTTGAACATGAGT (SEQ ID NO. 186) |
| TP53 | GSP1B | HB1091 | GTGGGAGGCTGTCAGTGG (SEQ ID NO. 187) |
| BDH1 | GSP1A | CA1001 | GCCACCCGGACGCTTC (SEQ ID NO. 188) |
| EMX1 | GSP1A | CA1002 | CAAACGAAACCCCACACGAAC (SEQ ID NO. 189) |
| LRRC4 | GSP1A | CA1003 | GCGGAGGGAGCGAGTTC (SEQ ID NO. 190) |
| LRRC4 | GSP1A | CA1004 | AACATAGTCCCCGCTGGCTA (SEQ ID NO. 191) |
| LRRC4 | GSP1A | CA1005 | GGAGCGCTCAAACCCACA (SEQ ID NO. 192) |
| LRRC4 | GSP1A | CA1006 | TACAACTGGCCCGTGTGG (SEQ ID NO. 193) |
| BDH1 | GSP1A | CA1007 | GTCCTTCTTCGCCTGGCATC (SEQ ID NO. 194) |
| CLEC11A | GSP1A | CA1008 | TGGGCTGGGAGACCGTG (SEQ ID NO. 195) |
| CLEC11A | GSP1A | CA1009 | CCACCGGCTCTTCAAGCTC (SEQ ID NO. 196) |
| CLEC11A | GSP1A | CA1010 | CATCGTCGCCGCTGCA (SEQ ID NO. 197) |
| HOXA1 | GSP1A | CA1011 | AACGCATAGGAGGGGTGGAA (SEQ ID NO. 198) |
| HOXA1 | GSP1A | CA1012 | CCTTTGGGTTGGGAGAAGAAAA (SEQ ID NO. 199) |
| EMX1 | GSP1A | CA1013 | CACCCGCCGTGTACGTTT (SEQ ID NO. 200) |
| AK055957 | GSP1A | CA1014 | CGGAATCGGGGTCTAAGTGG (SEQ ID NO. 201) |
| COTL1 | GSP1B | CB1001 | CCTAGCGATCAGGGCACC (SEQ ID NO. 202) |
| COTL1 | GSP1B | CB1002 | GATGAGAGAGCAGTCTGCGT (SEQ ID NO. 203) |
| COTL1 | GSP1B | CB1003 | CGTTCTCGCGCTCTGCTTAC (SEQ ID NO. 204) |
| ACP1 | GSP1B | CB1004 | GACCCCCGCTGCTCAC (SEQ ID NO. 205) |

TABLE 10-continued

| Primer Information | | | | |
|---|---|---|---|---|
| Gene Name | Primer Pool | Primer number | SEQ ID NO. | Nucleotide sequence (5'-3') |
| ACP1 | GSP1B | CB1005 | | CCCCCTAAGCCGCTGTT (SEQ ID NO. 206) |
| DAB2IP | GSP1B | CB1006 | | CCACACGGGCCAGTTGTA (SEQ ID NO. 207) |
| DAB2IP | GSP1B | CB1007 | | TGGCCGTTTTCGAAGAGGTAGA (SEQ ID NO. 208) |
| DAB2IP | GSP1B | CB1008 | | CACCGTTGGGCTGGTCC (SEQ ID NO. 209) |
| ACTB | GSP1B | CB1009 | | CGAGCTTGAAGAGCCGGTG (SEQ ID NO. 210) |
| BDH1 | GSP1B | CB1010 | | CGCCCACCCGAGTTCCT (SEQ ID NO. 211) |
| BDH1 | GSP1B | CB1011 | | TGGCCGGGACTGGAGG (SEQ ID NO. 212) |
| LRRC4 | GSP1B | CB1012 | | GGTAATACGTTCCGGCACTTCG (SEQ ID NO. 213) |
| LRRC4 | GSP1B | CB1013 | | GCCCCCACTTTCCAACTCC (SEQ ID NO. 214) |
| BDH1 | GSP1B | CB1014 | | GCGGTTCCGAAGTCCCTG (SEQ ID NO. 215) |
| LRRC4 | GSP1B | CB1015 | | CTCTCCAGCCCTCGGTG (SEQ ID NO. 216) |

TABLE 11

| Reaction Procedure | | |
|---|---|---|
| Temperature | Time | Number of cycles |
| 98° C. | 3 min | |
| 98° C. | 15 s | 6-10 cycles |
| 57-60° C. | 60-90 s | |
| 72° C. | 120 s | |
| 72° C. | 10 min | |

2. The two first-round amplification products obtained in step 1 were purified with 30-60 μl (i.e. 1-2 times the volume) of AMPure XP magnetic beads, respectively, then eluted with 25 d of DNase/RNase-Free Water to obtain the first round of purification product.

3. The first round of purification product obtained in step 2 was taken as templates to configure the reaction system of Table 12 (when using GSP1A mix amplification product as template, GSP2A mix was used for amplification; when using GSP1Bmix amplification product as template, GSP2B mix was used for amplification). The second round of PCR amplification was carried out according to the reaction procedure in Table 14 to obtain the second round of amplification product (stored at 4° C.).

TABLE 12

| Reaction system | |
|---|---|
| Composition | volume |
| KapaHifi | 15 μl |
| upstream primer3355 | 2 μl |
| GSP2Amix/GSP2Bmix | 1 μl |
| Index primer (10 μM) | 2 μl |
| template (GSP1A mix/GSP1Bmix) | 10 μl |
| Total volume | 30 μl |

In Table 12, the primer information is as follows:

Upstream primer 3355 (SEQ ID NO. 217):

-continued

5'-AATGATACGGCGACCACCGAGATCTACACTCTTTCCCTACACGACGCTCT-3'. The underlined part is the same part of the upstream primer 1355 of the first round, 3355 and 1355 are fixed sequences for sequencing on Illumina sequencing platform (can also be replaced with sequences that can be sequenced on other sequencing platforms).

GSP2A mix: Each primer in the primer pool GSP2A in Table 13 was dissolved and diluted to a concentration of 100 μM with TE buffer, then mixed in equal volumes, and diluted to 0.3 μM with TE buffer. The primers in the primer pool GSP2A were used to amplify the positive strand of the template.

GSP2B mix: Each primer in the primer pool GSP2B in Table 13 was dissolved and diluted to a concentration of 100 μM with TE buffer, then mixed in equal volumes, and diluted to 0.3 μM with TE buffer. The primers in the primer pool GSP2B were used to amplify the negative strand of the template.

In Table 13, positions 1 to 15 from the 5' end are the parts that bind to the Index primer.

The primers with the same primer number in GSP2A mix and GSP1A mix (that is, the last four digits of the primer number are the same) are designed for the same mutation site, and the two primers form a nested relationship.

The primers with the same primer number in GSP2B mix and GSP2A mix (that is, the last four digits of the primer number are the same) are designed for the same mutation site, and the two primers form a nested relationship.

Index primer: 5'-CAAGCAGAAGACGGCATACGAGAT (SEQ ID NO.218) ******GTGACTGGAGTTCCTTGGCACCCGAGAA-3' (SEQ ID NO.219); the underlined part is the part that binds to GSP2 mix. ****** is the index sequence position, the length of the index is 6-8 bp, the function is to distinguish the sequences between samples, and it is convenient for multiple samples to be mixed and sequenced. Except for the index sequence, the rest are fixed sequences of small RNA sequencing kit of Illumina.

TABLE 13

| Primer Information | | | |
|---|---|---|---|
| Gene name | Primer pool | Primer number | SEQ ID NO. Primer sequence (5'-3') |
| AXIN1 | GSP2A | HA2009 | CTTGGCACCCGAGAATTCCATTGTTCCTTGACGCAGAG (SEQ ID NO. 220) |
| AXIN1 | GSP2A | HA2010 | CTTGGCACCCGAGAATTCCAGACCTGGGGTATGAGCCTGA (SEQ ID NO. 221) |
| AXIN1 | GSP2A | HA2011 | CTTGGCACCCGAGAATTCCAAGGCTGAAGCTGGCGAGA (SEQ ID NO. 222) |
| AXIN1 | GSP2A | HA2012 | CTTGGCACCCGAGAATTCCATGAGGACGATGGCAGAGACG (SEQ ID NO. 223) |
| AXIN1 | GSP2A | HA2013 | CTTGGCACCCGAGAATTCCAGTACAGCGAAGGCAGAGAGT (SEQ ID NO. 224) |
| AXIN1 | GSP2A | HA2014 | CTTGGCACCCGAGAATTCCACACACAGGAGGAGGAAGGTGA (SEQ ID NO. 225) |
| AXIN1 | GSP2A | HA2015 | CTTGGCACCCGAGAATTCCATGTGTGGACATGGGCTGTG (SEQ ID NO. 226) |
| AXIN1 | GSP2A | HA2016 | CTTGGCACCCGAGAATTCCAACCCAAGTCAGGGGCGAA (SEQ ID NO. 227) |
| AXIN1 | GSP2A | HA2017 | CTTGGCACCCGAGAATTCCAGCGTGCAAAAGAAATGCCAAGAAG (SEQ ID NO. 228) |
| CTNNB1 | GSP2A | HA2018 | CTTGGCACCCGAGAATTCCATAGTCACTGGCAGCAACAGTC (SEQ ID NO. 229) |
| TERT | GSP2A | HA2019 | CTTGGCACCCGAGAATTCCACTGCAAGGCCTCGGGAGA (SEQ ID NO. 230) |
| TERT | GSP2A | HA2020 | CTTGGCACCCGAGAATTCCAATTCCTGGGAAGTCCTCAGCT (SEQ ID NO. 231) |
| TERT | GSP2A | HA2021 | CTTGGCACCCGAGAATTCCAGCTTGGAGCCAGGTGCCT (SEQ ID NO. 232) |
| TERT | GSP2A | HA2022 | CTTGGCACCCGAGAATTCCACATTTCCCACCCTTTCTCGACGG (SEQ ID NO. 233) |
| TERT | GSP2A | HA2023 | CTTGGCACCCGAGAATTCCAACGGGCCTGTGTCAAGGA (SEQ ID NO. 234) |
| TERT | GSP2A | HA2024 | CTTGGCACCCGAGAATTCCAATGCGTCCTCGGGTTCGT (SEQ ID NO. 235) |
| TERT | GSP2A | HA2025 | CTTGGCACCCGAGAATTCCAAGCCTAGGCCGATTCGAC (SEQ ID NO. 236) |
| TERT | GSP2A | HA2026 | CTTGGCACCCGAGAATTCCAGATTCGCGGGCACAGACG (SEQ ID NO. 237) |
| TERT | GSP2A | HA2027 | CTTGGCACCCGAGAATTCCATTCCAGCTCCGCCTCCTC (SEQ ID NO. 238) |
| HBV-C | GSP2A | HA2028 | CTTGGCACCCGAGAATTCCACCCATATCGTCAATCTTCTCGAGG (SEQ ID NO. 239) |
| HBV-C | GSP2A | HA2029 | CTTGGCACCCGAGAATTCCATCACAGTACCACAGAGTCTAGACTC (SEQ ID NO. 240) |
| HBV-C | GSP2A | HA2030 | CTTGGCACCCGAGAATTCCAAACCTCTTGTCCTCCAATTTGTCC (SEQ ID NO. 241) |
| HBV-C | GSP2A | HA2031 | CTTGGCACCCGAGAATTCCACCTGCTGCTATGCCTCATCTTC (SEQ ID NO. 242) |
| HBV-C | GSP2A | HA2032 | CTTGGCACCCGAGAATTCCACACGGGACCATGCAAGACC (SEQ ID NO. 243) |
| HBV-C | GSP2A | HA2033 | CTTGGCACCCGAGAATTCCATGGGCTTTCGCAAGATTCCTAT (SEQ ID NO. 244) |
| HBV-C | GSP2A | HA2034 | CTTGGCACCCGAGAATTCCACGTAGGGCTTTCCCCCACT (SEQ ID NO. 245) |
| HBV-C | GSP2A | HA2035 | CTTGGCACCCGAGAATTCCACCTCTATTACCAATTTTCTTTTGTCTTTGGG (SEQ ID NO. 246) |
| HBV-C | GSP2A | HA2036 | CTTGGCACCCGAGAATTCCAACACAATGTGGCTATCCTGCTT (SEQ ID NO. 247) |
| HBV-C | GSP2A | HA2037 | CTTGGCACCCGAGAATTCCAGGCAACGGTCAGGTCTCT (SEQ ID NO. 248) |
| HBV-C | GSP2A | HA2038 | CTTGGCACCCGAGAATTCCACTCTGCCGATCCATACTGCGGAA (SEQ ID NO. 249) |
| HBV-C | GSP2A | HA2039 | CTTGGCACCCGAGAATTCCACACTTCCTTTCCATGGCTGCTA (SEQ ID NO. 250) |
| HBV-C | GSP2A | HA2040 | CTTGGCACCCGAGAATTCCACCGTTTGGGACTCTACCGT (SEQ ID NO. 251) |
| HBV-C | GSP2A | HA2041 | CTTGGCACCCGAGAATTCCACGTGTGCACTTCGCTTCA (SEQ ID NO. 252) |
| HBV-C | GSP2A | HA2042 | CTTGGCACCCGAGAATTCCATTGCCCAAGGTCTTACATAAGAGG (SEQ ID NO. 253) |
| HBV-C | GSP2A | HA2043 | CTTGGCACCCGAGAATTCCAGTTTGTTTAAGGACTGGGAGGAGTT (SEQ ID NO. 254) |
| HBV-C | GSP2A | HA2044 | CTTGGCACCCGAGAATTCCAGGTCTGTTCACCAGCACCATG (SEQ ID NO. 255) |
| HBV-C | GSP2A | HA2045 | CTTGGCACCCGAGAATTCCACTGTGCCTTGGGTGGCTT (SEQ ID NO. 256) |

TABLE 13-continued

| Primer Information | | | |
|---|---|---|---|
| Gene name | Primer pool | Primer number | SEQ ID NO. Primer sequence (5'-3') |
| HBV-C | GSP2A | HA2046 | CTTGGCACCCGAGAATTCCATTGCCTTCTGATTTCTTTCCTTCTATT (SEQ ID NO. 257) |
| HBV-C | GSP2A | HA2047 | CTTGGCACCCGAGAATTCCAGAGTCTCCGGAACATTGTTCACC (SEQ ID NO. 258) |
| HBV-C | GSP2A | HA2048 | CTTGGCACCCGAGAATTCCAAGTTGATGAATCTGGCCACCT (SEQ ID NO. 259) |
| HBV-C | GSP2A | HA2049 | CTTGGCACCCGAGAATTCCACAGCTATGTTAATGTTAATATGGGCCTA (SEQ ID NO. 260) |
| HBV-C | GSP2A | HA2050 | CTTGGCACCCGAGAATTCCATATTTGGTGTCTTTTGGAGTGTGGAT (SEQ ID NO. 261) |
| HBV-C | GSP2A | HA2051 | CTTGGCACCCGAGAATTCCATAGAGGCAGGTCCCCTAGAAG (SEQ ID NO. 262) |
| HBV-C | GSP2A | HA2052 | CTTGGCACCCGAGAATTCCACAATGTTAGTATCCCTTGGACTCACA (SEQ ID NO. 263) |
| HBV- | GSP2A | HA2053 | CTTGGCACCCGAGAATTCCAACAGGAGGACATTATTGATAGATGTCA (SEQ ID NO. 264) |
| HBV-C | GSP2A | HA2054 | CTTGGCACCCGAGAATTCCAAACCTTACCAAGTATTTGCCCTT (SEQ ID NO. 265) |
| HBV-C | GSP2A | HA2055 | CTTGGCACCCGAGAATTCCATCTGTGGAAGGCTGGGATTCTATAT (SEQ ID NO. 266) |
| HBV-C | GSP2A | HA2056 | CTTGGCACCCGAGAATTCCAGGGACAAATCTTTCTGTTCCCA (SEQ ID NO. 267) |
| HBV-C | GSP2A | HA2057 | CTTGGCACCCGAGAATTCCAGGCCAGAGGCAAATCAGGT (SEQ ID NO. 268) |
| HBV-C | GSP2A | HA2058 | CTTGGCACCCGAGAATTCCACAGTCAGGAAGACAGCCTACTC (SEQ ID NO. 269) |
| HBV-B | GSP2A | HA2059 | CTTGGCACCCGAGAATTCCAAATACTGTCTCTGCCATATCGTCA (SEQ ID NO. 270) |
| HBV-B | GSP2A | HA2060 | CTTGGCACCCGAGAATTCCAGTGTGTTTCATGAGTGGGAGGA (SEQ ID NO. 271) |
| HBV-B | GSP2A | HA2061 | NA |
| HBV-B | GSP2A | HA2062 | NA |
| HBV-B | GSP2A | HA2063 | NA |
| HBV-B | GSP2A | HA2064 | CTTGGCACCCGAGAATTCCATTTGCCTTCTGACTTCTTTCCGTC (SEQ ID NO. 272) |
| HBV-B | GSP2A | HA2065 | CTTGGCACCCGAGAATTCCACACAGCACTCAGGCAAGCTA (SEQ ID NO. 273) |
| TP53 | GSP2A | HA2071 | CTTGGCACCCGAGAATTCCAGTCACTGCCATGGAGGAGC (SEQ ID NO. 274) |
| TP53 | GSP2A | HA2072 | CTTGGCACCCGAGAATTCCACCATGGGACTGACTTTCTGC (SEQ ID NO. 275) |
| TP53 | GSP2A | HA2073 | CTTGGCACCCGAGAATTCCAACTGCTCTTTTCACCCATCTACA (SEQ ID NO. 276) |
| TP53 | GSP2A | HA2074 | CTTGGCACCCGAGAATTCCATGTCCCCGGACGATATTGAAC (SEQ ID NO. 277) |
| TP53 | GSP2A | HA2075 | CTTGGCACCCGAGAATTCCACAGATGAAGCTCCCAGAATGCC (SEQ ID NO. 278) |
| TP53 | GSP2A | HA2076 | CTTGGCACCCGAGAATTCCATGTCATCTTCTGTCCCTTCCCA (SEQ ID NO. 279) |
| TP53 | GSP2A | HA2077 | CTTGGCACCCGAGAATTCCACAACTCTGTCTCCTTCCTCTTCCT (SEQ ID NO. 280) |
| TP53 | GSP2A | HA2078 | CTTGGCACCCGAGAATTCCATGTGCAGCTGTGGGTTGAT (SEQ ID NO. 281) |
| TP53 | GSP2A | HA2079 | CTTGGCACCCGAGAATTCCACAAGCAGTCACAGCACATGACG (SEQ ID NO. 282) |
| TP53 | GSP2A | HA2080 | CTTGGCACCCGAGAATTCCACCTCTGATTCCTCACTGATTGCT (SEQ ID NO. 283) |
| TP53 | GSP2A | HA2081 | CTTGGCACCCGAGAATTCCATTGCGTGTGGAGTATTTGGATG (SEQ ID NO. 284) |
| TP53 | GSP2A | HA2082 | CTTGGCACCCGAGAATTCCATCTTGGGCCTGTGTTATCTCCT (SEQ ID NO. 285) |
| TP53 | GSP2A | HA2083 | CTTGGCACCCGAGAATTCCAACATGTGTAACAGTTCCTGCATGG (SEQ ID NO. 286) |
| TP53 | GSP2A | HA2084 | CTTGGCACCCGAGAATTCCACTTGCTTCTCTTTTCCTATCCTGAGT (SEQ ID NO. 287) |
| TP53 | GSP2A | HA2085 | CTTGGCACCCGAGAATTCCACTTTGAGGTGCGTGTTTGTGC (SEQ ID NO. 288) |
| TP53 | GSP2A | HA2086 | CTTGGCACCCGAGAATTCCAGCAAGAAAGGGGAGCCTCA (SEQ ID NO. 289) |
| TP53 | GSP2A | HA2087 | CTTGGCACCCGAGAATTCCAATCACCTTTCCTTGCCTCTTTCC (SEQ ID NO. 290) |
| TP53 | GSP2A | HA2088 | CTTGGCACCCGAGAATTCCATTCTCCCCCTCCTCTGTTGC (SEQ ID NO. 291) |

TABLE 13-continued

| Primer Information | | | |
|---|---|---|---|
| Gene name | Primer pool | Primer number | SEQ ID NO. Primer sequence (5'-3') |
| TP53 | GSP2A | HA2089 | CTTGGCACCCGAGAATTCCACTTCGAGATGTTCCGAGAGCT (SEQ ID NO. 292) |
| TP53 | GSP2A | HA2090 | CTTGGCACCCGAGAATTCCACCTCCCTGCTTCTGTCTCCTA (SEQ ID NO. 293) |
| TP53 | GSP2A | HA2091 | CTTGGCACCCGAGAATTCCATCAGTCTACCTCCCGCCATA (SEQ ID NO. 294) |
| AXIN1 | GSP2B | HB2009 | CTTGGCACCCGAGAATTCCAGAAACTTGCTCCGAGGTCCA (SEQ ID NO. 295) |
| AXIN1 | GSP2B | HB2010 | CTTGGCACCCGAGAATTCCACATCCAGCAGGGAATGCAGT (SEQ ID NO. 296) |
| AXIN1 | GSP2B | HB2011 | CTTGGCACCCGAGAATTCCAGACACGATGCCATTGTTATCAAGASEQ ID NO. 297) |
| AXIN1 | GSP2B | HB2012 | CTTGGCACCCGAGAATTCCACTGTCTCCAGGAGCAGCTTC (SEQ ID NO. 298) |
| AXIN1 | GSP2B | HB2013 | CTTGGCACCCGAGAATTCCACGGAGGTGAGTACAGAAAGTGG (SEQ ID NO. 299) |
| AXIN1 | GSP2B | HB2014 | CTTGGCACCCGAGAATTCCAGGAGGCAGCTTGTGACACG (SEQ ID NO. 300) |
| AXIN1 | GSP2B | HB2015 | CTTGGCACCCGAGAATTCCACTCGTCCAGGATGCTCTCAG (SEQ ID NO. 301) |
| AXIN1 | GSP2B | HB2016 | CTTGGCACCCGAGAATTCCAGTGGTGGACGTGGTGGTG (SEQ ID NO. 302) |
| AXIN1 | GSP2B | HB2017 | CTTGGCACCCGAGAATTCCATGATTTTCTGGTTCTTCTCCGCAT (SEQ ID NO. 303) |
| CTNNB1 | GSP2B | HB2018 | CTTGGCACCCGAGAATTCCAGAGGTATCCACATCCTCTTCCTCA (SEQ ID NO. 304) |
| TERT | GSP2B | HB2019 | CTTGGCACCCGAGAATTCCAAGGACTTCCCAGGAATCCAG (SEQ ID NO. 305) |
| TERT | GSP2B | HB2020 | CTTGGCACCCGAGAATTCCAAGCTAGGAGGCCCGACTT (SEQ ID NO. 306) |
| TERT | GSP2B | HB2021 | CTTGGCACCCGAGAATTCCAACAACGGCCTTGACCCTG (SEQ ID NO. 307) |
| TERT | GSP2B | HB2022 | CTTGGCACCCGAGAATTCCACCACCCCAAATCTGTTAATCACC (SEQ ID NO. 308) |
| TERT | GSP2B | HB2023 | CTTGGCACCCGAGAATTCCAAACACTTCCCCGCGACTTGG (SEQ ID NO. 309) |
| TERT | GSP2B | HB2024 | CTTGGCACCCGAGAATTCCACGTGAAGGGGAGGACGGA (SEQ ID NO. 310) |
| TERT | GSP2B | HB2025 | CTTGGCACCCGAGAATTCCAGGGGCCATGATGTGGAGG (SEQ ID NO. 311) |
| TERT | GSP2B | HB2026 | CTTGGCACCCGAGAATTCCAAAGGTGAAGGGGCAGGAC (SEQ ID NO. 312) |
| TERT | GSP2B | HB2027 | CTTGGCACCCGAGAATTCCAGCGGAAAGGAAGGGGAGG (SEQ ID NO. 313) |
| TERT | GSP2B | HB2028 | CTTGGCACCCGAGAATTCCAGCAGCACCTCGCGGTAG (SEQ ID NO. 314) |
| HBV-C | GSP2B | HB2029 | CTTGGCACCCGAGAATTCCAGGAAAGTATAGGCCCCTCACTC (SEQ ID NO. 315) |
| HBV-C | GSP2B | HB2030 | CTTGGCACCCGAGAATTCCACTCTCCATGTTCGGGGCA (SEQ ID NO. 316) |
| HBV-C | GSP2B | HB2031 | CTTGGCACCCGAGAATTCCAGAGGATTCTTGTCAACAAGAAAAACCC (SEQ ID NO. 317) |
| HBV-C | GSP2B | HB2032 | CTTGGCACCCGAGAATTCCAACAAGAGGTTGGTGAGTGATTGG (SEQ ID NO. 318) |
| HBV-C | GSP2B | HB2033 | CTTGGCACCCGAGAATTCCAGTCCAGAAGAACCAACAAGAAGATGA (SEQ ID NO. 319) |
| HBV-C | GSP2B | HB2034 | CTTGGCACCCGAGAATTCCACATAGAGGTTCCTTGAGCAGGAATC (SEQ ID NO. 320) |
| HBV-C | GSP2B | HB2035 | CTTGGCACCCGAGAATTCCACACTCCCATAGGAATCTTGCGAA (SEQ ID NO. 321) |
| HBV-C | GSP2B | HB2036 | CTTGGCACCCGAGAATTCCACCCCCAATACCACATCATCCATA (SEQ ID NO. 322) |
| HBV-C | GSP2B | HB2037 | CTTGGCACCCGAGAATTCCAAGGGTTCAAATGTATACCCAAAGACAA (SEQ ID NO. 323) |
| HBV-C | GSP2B | HB2038 | CTTGGCACCCGAGAATTCCAAGTTTTAGTACAATATGTTCTTGCGGTA (SEQ ID NO. 324) |
| HBV-C | GSP2B | HB2039 | CTTGGCACCCGAGAATTCCACATTGTGTAAAAGGGGCAGCA (SEQ ID NO. 325) |
| HBV-C | GSP2B | HB2040 | CTTGGCACCCGAGAATTCCATGTTTACACAGAAAGGCCTTGTAAGT (SEQ ID NO. 326) |
| HBV-C | GSP2B | HB2041 | CTTGGCACCCGAGAATTCCACATGCGGCGATGGCCAATA (SEQ ID NO. 327) |
| HBV-C | GSP2B | HB2042 | CTTGGCACCCGAGAATTCCATTCCGAGAGAGGACAACAGAGTTGT (SEQ ID NO. 328) |

TABLE 13-continued

| Primer Information | | | |
|---|---|---|---|
| Gene name | Primer pool | Primer number | SEQ ID NO. Primer sequence (5'-3') |
| HBV-C | GSP2B | HB2043 | CTTGGCACCCGAGAATTCCAGACGGGACGTAAACAAAGGAC (SEQ ID NO. 329) |
| HBV-C | GSP2B | HB2044 | CTTGGCACCCGAGAATTCCAGGAGACCGCGTAAAGAGAGG (SEQ ID NO. 330) |
| HBV-C | GSP2B | HB2045 | CTTGGCACCCGAGAATTCCAGTGCAGAGGTGAAGCGAAGT (SEQ ID NO. 331) |
| HBV-C | GSP2B | HB2046 | CTTGGCACCCGAGAATTCCATCCAAGAGTCCTCTTATGTAAGACC (SEQ ID NO. 332) |
| HBV-C | GSP2B | HB2047 | CTTGGCACCCGAGAATTCCACAACTCCTCCCAGTCCTTAAACA (SEQ ID NO. 333) |
| HBV-C | GSP2B | HB2048 | CTTGGCACCCGAGAATTCCAGGTGCTGGTGAACAGACCAA (SEQ ID NO. 334) |
| HBV-C | GSP2B | HB2049 | CTTGGCACCCGAGAATTCCACTTGGAGGCTTGAACAGTAGGA (SEQ ID NO. 335) |
| HBV-C | GSP2B | HB2050 | CTTGGCACCCGAGAATTCCAAATTCTTTATACGGGTCAATGTCCA (SEQ ID NO. 336) |
| HBV-C | GSP2B | HB2051 | CTTGGCACCCGAGAATTCCACAGAGGCGGTGTCGAGGA (SEQ ID NO. 337) |
| HBV-C | GSP2B | HB2052 | CTTGGCACCCGAGAATTCCAACACAGAACAGCTTGCCTGA (SEQ ID NO. 338) |
| HBV-C | GSP2B | HB2053 | CTTGGCACCCGAGAATTCCACTGGGTCTTCCAAATTACTTCCCA (SEQ ID NO. 339) |
| HBV-C | GSP2B | HB2054 | CTTGGCACCCGAGAATTCCAGTTTCTCTTCCAAAGGTAAGACAGGA (SEQ ID NO. 340) |
| HBV-C | GSP2B | HB2055 | CTTGGCACCCGAGAATTCCAACCTGCCTCTACGTCTAACAACA (SEQ ID NO. 341) |
| HBV-C | GSP2B | HB2056 | CTTGGCACCCGAGAATTCCATTGTGAGTCCAAGGGATACTAACATTG (SEQ ID NO. 342) |
| HBV-C | GSP2B | HB2057 | CTTGGCACCCGAGAATTCCAGGGAGTTTGCCACTCAGGATTAAA (SEQ ID NO. 343) |
| HBV-C | GSP2B | HB2058 | CTTGGCACCCGAGAATTCCAGGGCAAATACTTGGTAAGGTTAGGATA (SEQ ID NO. 344) |
| HBV-C | GSP2B | HB2059 | CTTGGCACCCGAGAATTCCACCTTCCACAGAGTATGTAAATAATGCCTA (SEQ ID NO. 345) |
| HBV-C | GSP2B | HB2060 | CTTGGCACCCGAGAATTCCACTCCCATGCTGTAGCTCTTGTT (SEQ ID NO. 346) |
| HBV-C | GSP2B | HB2061 | CTTGGCACCCGAGAATTCCAGCTGGGTCCAACTGGTGATC (SEQ ID NO. 347) |
| HBV-C | GSP2B | HB2062 | CTTGGCACCCGAGAATTCCACCCCAAAAGACCACCGTGTG (SEQ ID NO. 348) |
| HBV-C | GSP2B | HB2063 | CTTGGCACCCGAGAATTCCATCTTCCTGACTGCCGATTGGT (SEQ ID NO. 349) |
| HBV-B | GSP2B | HB2064 | NA |
| HBV-B | GSP2B | HB2065 | NA |
| HBV-B | GSP2B | IB2066 | CTTGGCACCCGAGAATTCCACAAGACCTTGGGCAGGTTCC (SEQ ID NO. 350) |
| HBV-B | GSP2B | HB2067 | CTTGGCACCCGAGAATTCCAATTCTAAGGCTTCCCGATACAGA (SEQ ID NO. 351) |
| HBV-B | GSP2B | HB2068 | CTTGGCACCCGAGAATTCCAACGCTGGATCTTCTAAATTATTACCC (SEQ ID NO. 352) |
| HBV-B | GSP2B | HB2069 | NA |
| TP53 | GSP2B | HB2071 | CTTGGCACCCGAGAATTCCAGATCCACTCACAGTTTCCATAGG (SEQ ID NO. 353) |
| TP53 | GSP2B | HB2072 | CTTGGCACCCGAGAATTCCACAGCCCAACCCTTGTCCTTA (SEQ ID NO. 354) |
| TP53 | GSP2B | HB2073 | CTTGGCACCCGAGAATTCCATGGGAGCTTCATCTGGACCTG (SEQ ID NO. 355) |
| TP53 | GSP2B | HB2074 | CTTGGCACCCGAGAATTCCAGAAGGGACAGAAGATGACAGG (SEQ ID NO. 356) |
| TP53 | GSP2B | HB2075 | CTTGGCACCCGAGAATTCCACAAGAAGCCCAGACGGAAACC (SEQ ID NO. 357) |
| TP53 | GSP2B | HB2076 | CTTGGCACCCGAGAATTCCACCCCTCAGGGCAACTGAC (SEQ ID NO. 358) |
| TP53 | GSP2B | HB2077 | CTTGGCACCCGAGAATTCCAGTGCTGTGACTGCTTGTAGATGGC (SEQ ID NO. 359) |
| TP53 | GSP2B | HB2078 | CTTGGCACCCGAGAATTCCAATCTGAGCAGCGCTCATGGTG (SEQ ID NO. 360) |
| TP53 | GSP2B | HB2079 | CTTGGCACCCGAGAATTCCACCCTGTCGTCTCTCCAGC (SEQ ID NO. 361) |
| TP53 | GSP2B | HB2080 | CTTGGCACCCGAGAATTCCACTATGTCGAAAAGTGTTTCTGTCATCC (SEQ ID NO. 362) |
| TP53 | GSP2B | HB2081 | CTTGGCACCCGAGAATTCCAGAGACCCCAGTTGCAAACCAG (SEQ ID NO. 363) |

TABLE 13-continued

| Primer Information | | | |
|---|---|---|---|
| Gene name | Primer pool | Primer number | SEQ ID NO. Primer sequence (5'-3') |
| TP53 | GSP2B | HB2082 | CTTGGCACCCGAGAATTCCATGGGCCTCCGGTTCATGC (SEQ ID NO. 364) |
| TP53 | GSP2B | HB2083 | CTTGGCACCCGAGAATTCCAGTGCAGGGTGGCAAGTGG (SEQ ID NO. 365) |
| TP53 | GSP2B | HB2084 | CTTGGCACCCGAGAATTCCAGACAGGCACAAACACGCAC (SEQ ID NO. 366) |
| TP53 | GSP2B | HB2085 | CTTGGCACCCGAGAATTCCATTCTTGCGGAGATTCTCTTCCTCT (SEQ ID NO. 367) |
| TP53 | GSP2B | HB2086 | CTTGGCACCCGAGAATTCCACGCTTCTTGTCCTGCTTGCT (SEQ ID NO. 368) |
| TP53 | GSP2B | HB2087 | CTTGGCACCCGAGAATTCCAACTTGATAAGAGGTCCCAAGACTTAG (SEQ ID NO. 369) |
| TP53 | GSP2B | HB2088 | CTTGGCACCCGAGAATTCCAAGCCTGGGCATCCTTGAG (SEQ ID NO. 370) |
| TP53 | GSP2B | HB2089 | CTTGGCACCCGAGAATTCCACAGGAAGGGGCTGAGGTC (SEQ ID NO. 371) |
| TP53 | GSP2B | HB2090 | CTTGGCACCCGAGAATTCCACATGAGTTTTTTATGGCGGGAGGT (SEQ ID NO. 372) |
| TP53 | GSP2B | HB2091 | CTTGGCACCCGAGAATTCCACAGTGGGGAACAAGAAGTGGA (SEQ ID NO. 373) |
| BDH1 | GSP2A | CA2001 | CTTGGCACCCGAGAAGGACGCTTCTACACGCGAA (SEQ ID NO. 374) |
| EMX1 | GSP2A | CA2002 | CTTGGCACCCGAGAACACGAACGAAAAGGAACATGTCT (SEQ ID NO. 375) |
| LRRC4 | GSP2A | CA2003 | CTTGGCACCCGAGAACGAGTTCGCGGCTTCGG (SEQ ID NO. 376) |
| LRRC4 | GSP2A | CA2004 | CTTGGCACCCGAGAACAGCAGCAGCAGCGGG (SEQ ID NO. 377) |
| LRRC4 | GSP2A | CA2005 | CTTGGCACCCGAGAACAAACCCACAGGGTATCTATCAGG (SEQ ID NO. 378) |
| LRRC4 | GSP2A | CA2006 | CTTGGCACCCGAGAAGCTGGGCGTGCACGATC (SEQ ID NO. 379) |
| BDH1 | GSP2A | CA2007 | CTTGGCACCCGAGAACCTGGCATCGCTCACCC (SEQ ID NO. 380) |
| CLEC11A | GSP2A | CA2008 | CTTGGCACCCGAGAAGACCGTGGGGCTGTGAG (SEQ ID NO. 381) |
| CLEC11A | GSP2A | CA2009 | CTTGGCACCCGAGAACTCTTCAAGCTCGGAATGGA (SEQ ID NO. 382) |
| CLEC11A | GSP2A | CA2010 | CTTGGCACCCGAGAAGCCGCTGCAGACGGAT (SEQ ID NO. 383) |
| HOXA1 | GSP2A | CA2011 | CTTGGCACCCGAGAAAGGAGGGGTGGAACCCAG (SEQ ID NO. 384) |
| HOXA1 | GSP2A | CA2012 | CTTGGCACCCGAGAATGGGAGAAGAAAAAAACACACACAC (SEQ ID NO. 385) |
| EMX1 | GSP2A | CA2013 | CTTGGCACCCGAGAATTTCGCGGGACAAAAACCAC (SEQ ID NO. 386) |
| AK055957 | GSP2A | CA2014 | CTTGGCACCCGAGAATCTAAGTGGCCAGGGCACTG (SEQ ID NO. 387) |
| COTL1 | GSP2B | CB2001 | CTTGGCACCCGAGAAGATCAGGGCACCTTGGGC (SEQ ID NO. 388) |
| COTL1 | GSP2B | CB2002 | CTTGGCACCCGAGAACTGCAACACCGCGAGCC (SEQ ID NO. 389) |
| COTL1 | GSP2B | CB2003 | CTTGGCACCCGAGAACGCTCTGCTTACGTGCTGAC (SEQ ID NO. 390) |
| ACP1 | GSP2B | CB2004 | CTTGGCACCCGAGAAGCCGCTGCAGCAGTCC (SEQ ID NO. 391) |
| ACP1 | GSP2B | CB2005 | CTTGGCACCCGAGAACGCTGTTGCCTTGGCGA (SEQ ID NO. 392) |
| DAB2IP | GSP2B | CB2006 | CTTGGCACCCGAGAAGCCAGTTGTAGGGAGCGA (SEQ ID NO. 393) |
| DAB2IP | GSP2B | CB2007 | CTTGGCACCCGAGAACGAAGAGGTAGAGGCCCTCG (SEQ ID NO. 394) |
| DAB2IP | GSP2B | CB2008 | CTTGGCACCCGAGAAGTCCGGGCTGAGCGGAT (SEQ ID NO. 395) |
| ACTB | GSP2B | CB2009 | CTTGGCACCCGAGAAGCCCTCCACCACGGTTCTAT (SEQ ID NO. 396) |
| BDH1 | GSP2B | CB2010 | CTTGGCACCCGAGAAGAGTTCCTCCCAGCCAGC (SEQ ID NO. 397) |
| BDH1 | GSP2B | CB2011 | CTTGGCACCCGAGAAGGGACTGGAGGGCGTAGAG (SEQ ID NO. 398) |
| LRRC4 | GSP2B | CB2012 | CTTGGCACCCGAGAAACTTCGCGGCGGCTCA (SEQ ID NO. 399) |
| LRRC4 | GSP2B | CB2013 | CTTGGCACCCGAGAACCAACTCCACGGTTCCTGC (SEQ ID NO. 400) |

TABLE 13-continued

| Primer Information | | | |
|---|---|---|---|
| Gene name | Primer pool | Primer number | SEQ ID NO. Primer sequence (5'-3') |
| BDH1 | GSP2B | CB2014 | CTTGGCACCCGAGAATGAGGGCGAAGGCCTGA (SEQ ID NO. 401) |
| LRRC4 | GSP2B | CB2015 | CTTGGCACCCGAGAAGGTGGTACCGATGAGAGCG (SEQ ID NO. 402) |

Note: NA means no primer.

TABLE 14

| Reaction Procedure | | |
|---|---|---|
| Temperature | Time | Number of cycles |
| 98° C. | 3 min | |
| 98° C. | 15 s | 6-10 cycles |
| 57-60° C. | 60-90 s | |
| 72° C. | 90 s | |
| 98° C. | 15 s | 6-10 cycles |
| 57-60° C. | 30-60 s | |
| 72° C. | 30 s | |
| 72° C. | 10 min | |

4. The product of the second round of amplification using GSP2A mix obtained in step 3 and the product of the second round of amplification using GSP1B mix were mixed in equal volumes, purified with AMPure XP magnetic beads at a ratio of 1:(1-2), then eluted with 50 μl of DNase/RNase-Free Water to obtain the product of the second round of purification, which was the sequencing library that could be sequenced on the Illumina Hiseq X platform.

DNA random tags on the MC library were added to the downstream of the Read1 sequence of the sequencing library along with the cfDNA sequences. During sequencing, DNA random tag sequence, anchor sequence, and cfDNA sequence (c, d, and e sequences in FIG. 1) were obtained sequentially.

The analysis method of hepatocellular carcinoma-specific gene variation was as follows: DNA molecules whose sequencing data met the criterion A were traced back to a molecular cluster; the molecular clusters which met the criterion B were labeled as a pair of duplex molecular clusters; for a mutation, if the following (a1) or (a2) is satisfied, the mutation is a true mutation from the original DNA sample: (a1) supported by at least one pair of duplex molecular clusters; (a2) supported by at least 4 molecular clusters; criterion A means satisfying ①, ② and ③ at the same time; ① the length of the DNA inserts is the same and the sequences are the same except for the mutation sites; ② the random tag sequences are the same; ③ the anchor sequences are the same; criterion B means satisfying both ④ and ⑤; ④ the length of the DNA inserts is the same and the sequences are the same except for the mutation sites; ⑤ the anchor sequences at both ends of the molecular cluster are the same but in opposite positions.

The analysis method for the degree of hepatocellular carcinoma-specific methylation modification was as follows: the DNA molecules whose sequencing data met the criterion C were labeled as a cluster, and the number of clusters whose ends were the restriction sites of interest was calculated respectively, and recorded as unmethylated fragments; the number of all the clusters whose amplified fragments reached or exceeded the first restriction site was calculated, and recorded as the total number of fragments. The average methylation level of the corresponding region was calculated according to the number of two fragments. The methylation level of the region=(1−the number of unmethylated fragments/the total number of fragments)×100%. Criterion C means satisfying ⑥, ⑦ and ⑧ at the same time; ⑥ the random tag sequences are the same; ⑦ the anchor sequences are the same; ⑧ the length of the DNA inserts is the same and the sequences are the same except for the mutation sites.

Example 3. Capture and Sequencing of MC Library

Figure 3:
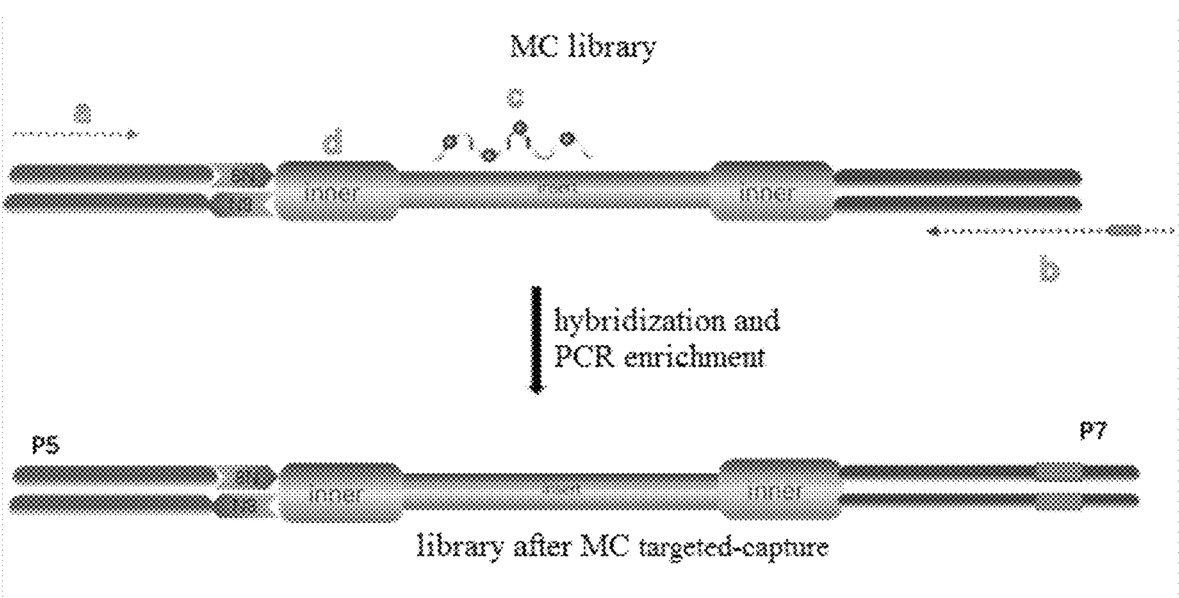
FIG. 3 is a schematic diagram of MC library capture and duplex sequencing.

As shown in FIG. 3, target region enrichment can be captured based on the optimized design of existing commercial target capture kits. For example: methylated region-based capture can refer to Roche SeqCap Epi CpGiant Enrichment Kit (Roche 07138881001) or Illumina Infinium Methylation EPIC BeadChipWG-317-1001), the design of targeted capture of methylated regions needs to be screened according to the coverage of the restriction sites, and the bases converted based on bisulfite treatment in the probe should be adjusted. For the capture based on gene variation region, could refer to Agilent sureselect XT target capture kit (Agilent5190-8646), only the primers amplified in the last step of PCR were replaced with the following primers:

The upstream primer is: 5'-AATGATACGGCGACCACCGAGATCTACACTCTTTCCCTACACGACGCTC TTCCGATCT-3' (SEQ ID NO.403) ("a" in FIG. 3), the underlined part is the same as the MC_F part of the primer), the function is to amplify the library, and the rest is the fixed sequence required for sequencing on the illumina sequencing platform.

The downstream primer is: 5'-CAAGCAGAAGACGGCATACGAGAT (SEQ ID NO.404) ******GTCTCGTGGGCTCGGAGATGTGTATAA-3' (SEQ ID NO.405) ("b" in FIG. 3), the underlined part is the same as the primer MC_R, and the function is to amplify the library. ****** is the index sequence position, the length of the index is 6-8 bp, the function is to distinguish the sequences between samples, and it is convenient for multiple samples to be mixed and sequenced. The rest is the fixed sequence required for sequencing on the illumina sequencing platform.

The captured library has the same DNA random tag sequence, anchor sequence and cfDNA sequence as the MC library, which are located downstream of Read1 sequentially.

DNA molecules whose sequencing data met the criterion A were traced back to a molecular cluster; criterion A means satisfying ①, ② and ③ at the same time; ① the length of the DNA inserts is the same and the sequences are the same except for the mutation sites; ② the random tag sequences are the same; ③ the anchor sequences are the same. The molecular clusters which met the criterion B were labeled as a pair of duplex molecular clusters. Criterion B means satisfying both ④ and ⑤; ④ the length of the DNA inserts is the same and the sequences are the same except for the mutation sites; ⑤ the anchor sequences at both ends of the molecular cluster are the same but in opposite positions. For a mutation, if the following (a1) or (a2) is satisfied, the mutation is a true mutation from the original DNA sample: (a1) supported by at least one pair of duplex molecular clusters; (a2) supported by at least 4 molecular clusters. Mutations supported by a pair of duplex clusters are more reliable and it can reduce false positive mutations by 90%.

The DNA molecules whose sequencing data met the criterion C were labeled as a cluster, and the number of clusters whose ends were the restriction sites of interest was calculated respectively and recorded as unmethylated fragments; the number of all the clusters whose amplified fragments reached or exceeded the first restriction site was calculated, and recorded as the total number of fragments. The average methylation level of the corresponding region was calculated according to the number of two fragments. The methylation level of the region=(1−the number of unmethylated fragments/the total number of fragments)×100%. Criterion C means satisfying ⑥, ⑦ and ⑧ at the same time; ⑥ the random tag sequences are the same; ⑦ the anchor sequences are the same; ⑧ the length of the DNA inserts is the same and the sequences are the same except for the mutation sites.

Example 4. Comparison of Detection Method

1. Comparison 1 of Detection Methods (1) cfDNA specimens from 21 hepatocellular carcinoma patients were collected.

(2) After completing step 1, each cfDNA sample was taken, and the MC library was constructed according to the method in Example 1. Then, the RaceSeq target region was enriched and sequenced according to the method in Example 2 to obtain the methylation level of the AK055957 gene.

(3) After completing step 1, each cfDNA specimen was taken, and the Padlock method (Xu R H, Wei W, Krawczyk M, et al. Circulating tumour DNA methylation markers for diagnosis and prognosis of hepatocellular carcinoma[J]. Nature Materials, 2017, 16(11):1155.) was used to detect the methylation level of the AK055957 gene. Padlock is a methylation-targeted sequencing technology, and the conformation of Padlock probe is similar to that of padlock. It can be applied to high-throughput methylation-targeted sequencing, and is an efficient library construction method after bisulfite conversion, known as "BSPP". After the cfDNA is converted by bisulfite, it can be amplified and ligated into a circular shape when paired complementary to the capture arm of a bisulfite padlock probe (BSPP). Padlock probes ligated into circles can be screened with exonuclease, and the corresponding DNA methylation information can be obtained by sequencing the amplified products.

Figure 4:
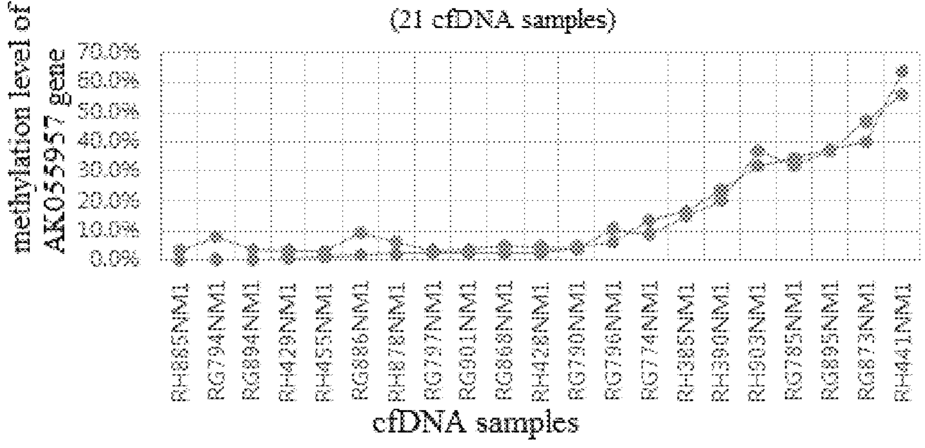
FIG. 4 shows the detection results of the methylation level of the AK055957 gene by the Padlock method and the mutation/methylation co-detection method (ie, the method provided by the present invention).

The test results are shown in FIG. 4. The results show that the Padlock method and the mutation/methylation co-detection method (that is, the method provided by the present invention) have basically the same detection results on the methylation level of the AK055957 gene (a hepatocellular carcinoma-specific gene).

2. Comparison 2 of Detection Methods (1) Mutation and Mutation Frequency Detected by Mutation/Methylation Co-Detection Method ① cfDNA of a hepatocellular carcinoma patient was collected.

② After completing step ①, 5-40 ng of cfDNA was taken to configure the reaction system as shown in Table 1, and then enzyme digestion was performed in the PCR machine to obtain the enzyme-digested product (stored at 4° C.). Wherein the time of enzyme digestion was 0 h, 0.2 h, 0.4 h, 0.6 h, 0.8 h or 1 h.

③ After completing step ②, the enzyme digestion product was taken to construct the MC library according to the methods of 2 to 6 in Example 1, then, RaceSeq target region enrichment and sequencing were performed according to the method in Example 2. During data analysis, the sequencing data of DNA molecules with the same random tag sequence, the same DNA insert length, and the same sequence except for the mutation sites, were traced back to a molecular cluster. If the number of molecules in the cluster is >5 and the concordance rate of molecular mutation within the cluster is >80% and the number of clusters is ≥5, the mutation is a true mutation from the original DNA sample. The proportion of clusters containing this molecular mutation is the mutation frequency.

(3) Detection of Mutation and Mutation Frequency by Single Mutation Detection Method ① cfDNA of a hepatocellular carcinoma patient was collected.

② After completing step ①, 5-40 ng of cfDNA was taken to configure the reaction system as shown in Table 3, and then end repair and adding A treatment at the 3' end in a PCR machine were performed according to the reaction procedure in Table 4 to obtain a reaction product (stored at 4° C.).

③ After completing step ②, the enzyme digestion product was taken to construct the MC library according to the methods of 2 to 6 in Example 1, then, RaceSeq target region enrichment and sequencing were performed according to the method in Example 2. During data analysis, the sequencing data of DNA molecules with the same random tag sequence, the same DNA insert length, and the same sequence except for the mutation sites, were traced back to a molecular cluster. If the number of molecules in the cluster is >5 and the concordance rate of molecular mutation within the cluster is >80% and the number of clusters is ≥5, the mutation is a true mutation from the original DNA sample. The proportion of clusters containing this molecular mutation is the mutation frequency.

(4) The mutation frequency of each mutation site obtained according to the mutation/methylation co-detection method was taken as the abscissa, the mutation frequency obtained by the single mutation detection method was taken as the ordinate, a scatter plot was drawn, and linear fitting curve and correlation coefficient R2 was added.

Figure 5:
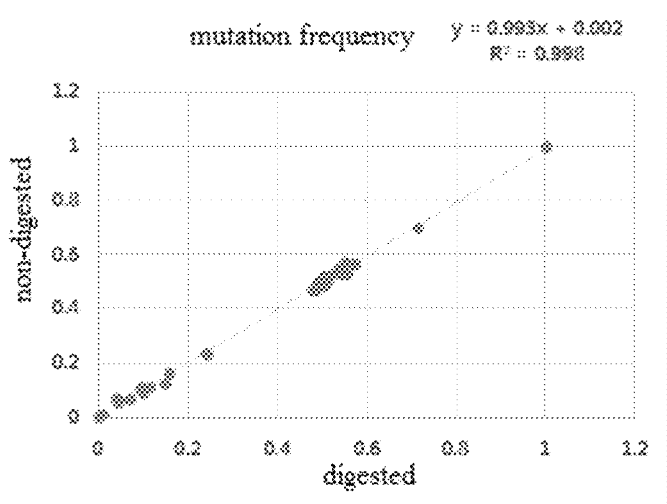
FIG. 5 shows the results of mutation and mutation frequency detection by single mutation detection method and mutation/methylation co-detection method.

The test results are shown in FIG. 5. The results show that mutation/methylation co-detection method and single mutation detection method have basically the same detection results for mutation and mutation frequency, that is, methylation detection does not affect the detection of mutation.

Example 5. Accuracy Experiment

The mutation standard is a product of Horizon Discovery Company, catalog number HD701.

1. Accuracy Experiment 1

(1) The mutation standard was taken to construct the MC library according to the methods of 1 to 6 in Example 1, then, RaceSeq target region enrichment and sequencing were performed according to the method (only GSP2A mix in step 3 was replaced with GSP2A mix-1 and GSP2B mix was replaced with GSP2B mix-1) in Example 2.

GSP2A mix-1: Each primer in the primer pool GSP2A in Table 15 was dissolved and diluted to a concentration of 100 μM with TE buffer, then mixed in equal volumes, and diluted to 0.3 μM with TE buffer. The primers in the primer pool GSP2A were used to amplify the positive strand of the template.

GSP2B mix-1: Each primer in the primer pool GSP2B in Table 15 was dissolved and diluted to a concentration of 100 μM with TE buffer, then mixed in equal volumes, and diluted to 0.3 μM with TE buffer. The primers in the primer pool GSP2B were used to amplify the negative strand of the template.

TABLE 15

| Primer sequences | | | | | |
|---|---|---|---|---|---|
| Gene name | Chromosome | Mutation site | Primer pool | Primer number | Primer sequence (5'-3') |
| PIK3CA | 3 | 178916875 | GSP2A | HA2094 | Cagaaagggaagaatttttgatgaaaca (SEQ ID NO: 406) |
| PIK3CA | 3 | 178921551 | GSP2A | HA2095 | ctcagaataaaaattctttgtgcaacctac (SEQ ID NO: 407) |
| PIK3CA | 3 | 178936082 | GSP2A | HA2096 | gctcaaagcaatttctacacgagatc (SEQ ID NO: 408) |
| PIK3CA | 3 | 178952072 | GSP2A | HA2097 | gcaagaggctttggagtatttcatg(SEQ ID NO: 409) |
| KRAS | 12 | 25398285 | GSP2A | HA2115 | tgactgaatataaacttgtggtagttgg (SEQ ID NO: 410) |
| KRAS | 12 | 25380277 | GSP2A | HA2116 | cctgtctcttggatattctcgacac (SEQ ID NO: 411) |
| KRAS | 12 | 25378562 | GSP2A | HA2117 | gcaagaagttatggaattccttttattgaa (SEQ ID NO: 412) |
| EGFR | 7 | 55241707 | GSP2A | HA2121 | ttgaggatcttgaaggaaactgaatt (SEQ ID NO: 413) |
| EGFR | 7 | 55242463 | GSP2A | HA2122 | tgagaaagttaaaattcccgtogcta (SEQ ID NO: 414) |
| EGFR | 7 | 55249004 | GSP2A | HA2123 | ctccaggaagcctacgtgatg (SEQ ID NO: 415) |
| EGFR | 7 | 55249071 | GSP2A | HA2124 | acctccaccgtgcagctc (SEQ ID NO: 416) |
| EGFR | 7 | 55259514 | GSP2A | HA2125 | ccgcagcatgtcaagatcacag (SEQ ID NO: 417) |
| PIK3CA | 3 | 178916875 | GSP2B | HB2094 | ggttgaaaaagccgaaggtcac (SEQ ID NO: 418) |
| PIK3CA | 3 | 178921551 | GSP2B | HB2095 | catttgactttaccttatcaatgtctcgaa (SEQ ID NO: 419) |
| PIK3CA | 3 | 178936082 | GSP2B | HB2096 | acttacctgtgactccatagaaaatott (SEQ ID NO: 420) |
| PIK3CA | 3 | 178952072 | GSP2B | HB2097 | caatccatttttgttgtccagcc (SEQ ID NO: 421) |
| KRAS | 12 | 25398285 | GSP2B | HB2115 | tagctgtatcgtcaaggcactc (SEQ ID NO: 422) |
| KRAS | 12 | 25380277 | GSP2B | HB2116 | ggtccctcattgcactgtact (SEQ ID NO: 423) |
| KRAS | 12 | 25378562 | GSP2B | HB2117 | tgtatttatttcagtgttacttacctgtcttg (SEQ ID NO: 424) |
| EGFR | 7 | 55241707 | GSP2B | HB2121 | accttatacaccgtgccgaa (SEQ ID NO: 425) |
| EGFR | 7 | 55242463 | GSP2B | HB2122 | actcacatcgaggatttccttgtt (SEQ ID NO: 426) |
| EGFR | 7 | 55249004 | GSP2B | HB2123 | cggtggaggtgaggcagat (SEQ ID NO: 427) |
| EGFR | 7 | 55249071 | GSP2B | HB2124 | gtccaggaggcagccgaa (SEQ ID NO: 428) |
| EGFR | | 55259514 | GSP2B | HB2125 | gtattotttctottccgcaccca (SEQ ID NO: 429) |

(2) According to the sequencing results, the mutation frequency of the mutation site was obtained.

The test results are shown in Table 16. The results show that the mutation frequency of the mutation site is basically close to the theoretical value by using the mutation/methylation co-detection method to detect the mutation standard. It can be seen that the mutation/methylation co-detection method has high accuracy for the mutation detection of hepatocellular carcinoma-specific genes (such as CTNNB1 gene, TP53 gene, and AXIN1 gene).

TABLE 16

| Accuracy experiment | | | | | | | |
|---|---|---|---|---|---|---|---|
| | | Mutation/methylation co-detection results | | Mutation frequency of | | | |
| Gene name | geneID | Sequencing depth | Mutation frequency | mutation standard | Mutation type | Ref | Alt |
| EGFR | ENSG00000146648 | 10191 | 0.0147 | 0.01 | INS | — | C |
| PIK3CA | ENSG00000121879 | 5020 | 0.07749 | 0.09 | SNP | G | A |
| PIK3CA | ENSG00000121879 | 9192 | 0.19093 | 0.175 | SNP | A | G |
| EGFR | ENSG00000146648 | 3988 | 0.27282 | 0.245 | SNP | G | A |
| EGFR | ENSG00000146648 | 10147 | 0.00581 | 0.02 | SNP | C | T |
| EGFR | ENSG00000146648 | 12716 | 0.03374 | 0.03 | SNP | T | G |
| KRAS | ENSG00000133703 | 12604 | 0.14392 | 0.15 | SNP | C | T |
| KRAS | ENSG00000133703 | 12609 | 0.06138 | 0.06 | SNP | C | T |

Note:
geneID represents the gene number in the Ensemble database, Ref is the normal type, Alt is the type after gene mutation, INS stands for insertion, DEL for deletion, and SNP for single nucleotide polymorphism.

2. Accuracy Experiment 2

Human methylation and non-methylation standards are products of Zymo Research, Catalog No. D5014.

(1) The methylation standard and the non-methylation standard in the human methylation and non-methylation standard are mixed according to different ratios to obtain the sample to be tested. In the sample to be tested, the proportion of methylation standard is 0%, 20% or 100%, namely tumor-specific genes (BDH1 gene, EMX1 gene, LRRC4 gene, CLEC11A gene, HOXA1 gene, AK055957 gene, COTL1 gene, ACP1 gene or DAB2IP gene) were methylated at 0%, 20% or 100%.

(2) The sample to be tested was taken, the MC library was constructed according to the method in Example 1, and then the RaceSeq target region was enriched and sequenced according to the method in Example 2 to obtain the detection value of the methylation site.

The test results are shown in Table 17 and Table 18 (the last four digits of the sample type are the names of tumor-specific genes). The methylation standard was detected by mutation/methylation co-detection method, and the detected value was basically close to the theoretical value. It can be seen that the mutation/methylation co-detection method has high accuracy in the detection of methylation levels of tumor-specific genes (such as BDH1 gene, EMX1 gene, LRRC4 gene, CLEC11A gene, HOXA1 gene, AK055957 gene, COTL1 gene, ACP1 gene, DAB2IP gene).

TABLE 17

| Accuracy test results for methylation standards (positive strand) | | | |
|---|---|---|---|
| Sample type | 0% methylation standard | 20% methylation standard | 100% methylation standard |
| CA2001_BDH1 | 2% | 18% | 97% |
| CA2002_EMX1 | 3% | 19% | 96% |
| CA2003_LRRC4 | 2% | 9% | 100% |
| CA2004_LRRC4 | 3% | 32% | 97% |
| CA2006_CLEC11A | 2% | 20% | 97% |
| CA2007_CLEC11A | 2% | 25% | 99% |
| CA2008_HOXA1 | 3% | 20% | 99% |
| CA2009_HOXA1 | 3% | 23% | 99% |
| CA2010_EMX1 | 3% | 32% | 99% |
| CA2011_AK055957 | 3% | 23% | 99% |
| CA2012_COTL1 | 3% | 18% | 98% |
| CA2013_ACP1 | 4% | 27% | 98% |
| CA2014_DAB2IP | 2% | 21% | 98% |

TABLE 18

| Accuracy test results for methylation standards (negative strand) | | | |
|---|---|---|---|
| Sample type | 0% methylation standard | 20% methylation standard | 100% methylation standard |
| CB2001_BDH1 | 3% | 21% | 96% |
| CB2002_LRRC4 | 3% | 17% | 98% |
| CB2004_LRRC4 | 2% | 9% | 96% |
| CB2005_DAB2IP | 2% | 3% | 99% |
| CB2007_CLEC11A | 4% | 50% | 94% |
| CB2008_CLEC11A | 3% | 18% | 97% |
| CB2009_HOXA1 | 2% | 20% | 98% |
| CB2011_EMX1 | 3% | 23% | 99% |
| CB2012_AK055957 | 4% | 19% | 100% |
| CB2013_RASSF2 | 7% | 60% | 94% |
| CB2015_DAB2IP | 3% | 23% | 99% |

Example 6. Application of Mutation/Methylation Co-Detection Method in cfDNA of Patients with Hepatocellular Carcinoma 1. Blood samples from 1 normal person, 1 patient with liver cirrhosis and 3 patients with hepatocellular carcinoma were collected, and cfDNA was extracted.

2. 5-40 ng of cfDNA was taken to construct the MC library according to Example 1, and RaceSeq target region enrichment and sequencing was performed according to the method in Example 2.

3. The methylation detection results are shown in Table 19 and Table 20.

The results showed that HCC-specific hypermethylated genes had higher methylation levels in the examined HCC samples than in non-HCC samples.

Mutation/methylation co-detection method can be applied to the detection of hepatocellular carcinoma cfDNA samples.

TABLE 19

Detection results of methylation levels in target regions of cfDNA samples (positive strand)

| Sample type | Normal | Cirrhosis | HCC1 | HCC2 | HCC3 |
|---|---|---|---|---|---|
| CA2001_BDH1 | 3% | 3% | 28% | 25% | 47% |
| CA2002_EMX1 | 4% | 6% | 11% | 26% | 4% |
| CA2003_LRRC4 | 3% | 5% | 16% | 28% | 28% |
| CA2004_LRRC4 | 3% | 6% | 29% | 46% | 48% |
| CA2006_CLEC11A | 3% | 4% | 11% | 20% | 2% |
| CA2007_CLEC11A | 3% | 5% | 22% | 25% | 10% |
| CA2008_HOXA1 | 4% | 4% | 24% | 33% | 5% |
| CA2009_HOXA1 | 8% | 7% | 10% | 11% | 11% |
| CA2010_EMX1 | 7% | 9% | 21% | 47% | 8% |
| CA2011_AK055957 | 5% | 9% | 40% | 43% | 45% |
| CA2012_COTL1 | 5% | 9% | 17% | 19% | 5% |
| CA2013_ACP1 | 1% | 3% | 5% | 5% | 14% |
| CA2014_DAB2IP | 5% | 7% | 19% | 27% | 50% |

TABLE 20

Detection results of methylation levels in target regions of cfDNA samples (negative strand)

| Sample type | Normal | Cirrhosis | HCC1 | HCC2 | HCC3 |
|---|---|---|---|---|---|
| CB2001_BDH1 | 5% | 5% | 24% | 23% | 56% |
| CB2002_LRRC4 | 4% | 13% | 40% | 47% | 50% |
| CB2004_LRRC4 | 1% | 4% | 11% | 17% | 28% |
| CB2005_DAB2IP | 4% | 5% | 10% | 16% | 27% |
| CB2007_CLEC11A | 11% | 8% | 17% | 38% | 6% |
| CB2008_CLEC11A | 2% | 5% | 22% | 23% | 7% |
| CB2009_HOXA1 | 4% | 2% | 10% | 21% | 3% |
| CB2011_EMX1 | 12% | 11% | 20% | 39% | 7% |
| CB2012_AK055957 | 3% | 9% | 39% | 38% | 43% |
| CB2013_RASSF2 | 5% | 1% | 4% | 18% | 4% |
| CB2015_DAB2IP | 9% | 6% | 18% | 31% | 57% |

INDUSTRIAL APPLICATION

The present invention discloses a method for simultaneously detecting the mutation (including point mutation, insertion-deletion mutation, HBV integration and other mutation forms) and/or methylation of tumor-specific genes in ctDNA in one sample. Not only the sample size requirement is low, but the MC library prepared by this method can support 10-20 subsequent detections. The results of each test can represent the mutation status of all the original ctDNA specimens and the methylation modification status of the region covered by the restriction sites, without reducing the sensitivity and specificity. At the same time, the library construction method is not only applicable to cfDNA samples, but also to genomic DNA or cDNA samples. The invention has important clinical significance for early tumor screening, disease tracking, efficacy evaluation, prognosis prediction and the like, and has great application value.

The invention claimed is:

1. A method for constructing a sequencing library, comprising the following steps sequentially:

(1) taking a DNA sample and digesting it with a methylation-sensitive restriction endonuclease;

(2) the DNA sample digested in step (1) is subjected to end repair and adding A treatment at the 3' end sequentially;

(3) ligating the DNA sample processed in step (2) with an adapter in an adapter mixture, and obtaining a library after PCR amplification;

(4) amplifying the library obtained in step (3);

the adapter mixture consists of n adapters;

each adapter is formed by an upstream primer A and a downstream primer A to form a partial double-stranded structure; the upstream primer A includes a sequencing adapter A, a random tag, an anchor sequence A and a base T sequentially from the 5' end; the downstream primer A includes an anchor sequence B and a sequencing adapter B sequentially from the 5' end; the partial double-stranded structure is formed by the reverse complementation of the anchor sequence A and the anchor sequence B;

the sequencing adapter A and sequencing adapter B are corresponding sequencing adapters selected according to different sequencing platforms;

the random tag is 8-14 bases in length;

the anchor sequence A has a length of 12-20 bp, and has ≤3 consecutive repeating bases;

the n adapters use n different anchor sequences A(s), and the four bases in each anchor sequence A are balanced, and the number of mismatched bases ≥3;

n is any natural number ≥8;

a primer pair used for amplification in step (4) consists of two single-stranded DNA molecules shown in SEQ ID NO. 25 and SEQ ID NO. 26 in the sequence listing;

wherein, the number of mismatched bases ≥3 means that the adapter mixture contains n anchor sequences A(s), and there are at least 3 differences in the bases between each anchor sequence A; the difference is different positions or different sequences.

2. The construction method according to claim 1, wherein:

the DNA sample is a genomic DNA, cDNA, ct DNA or cf DNA sample.

3. A DNA library constructed by the method according to claim 1; wherein, DNA molecules in the DNA library contain double-stranded adapters, which are Y-shaped adapters, each DNA molecule includes a random tag composed of 8-14 random bases and an anchor sequence with a length of 12-20 bp on one or both ends of the adapter; the DNA library contains an adapter mixture employing n distinct anchor sequences, where n≥8; each anchor sequence is balanced of the four nucleotide bases, and the number of mismatched bases between any two anchor sequences is ≥3.

4. A kit for detecting tumor mutation and/or methylation in DNA samples, comprising the adapter mixture and primer combinations according to claim 1;

wherein the tumor is a liver malignant tumor;

the primer combinations include primer set I, primer set II, primer set III, primer set IV, primer set V, primer set VI, primer set VII and primer set VIII, wherein:

the primer set I includes 78 single-stranded DNA molecules, and the nucleotide sequences of the 78 single-stranded DNA molecules are shown in SEQ ID NO. 28 to SEQ ID NO. 105 in the sequence listing sequentially;

the primer set II includes 82 single-stranded DNA molecules, and the nucleotide sequences of the 82 single-stranded DNA molecules are shown in SEQ ID NO. 106 to SEQ ID NO. 187 in the sequence listing sequentially;

the primer set III includes 14 single-stranded DNA molecules, and the nucleotide sequences of the 14 single-stranded DNA molecules are shown in SEQ ID NO. 188 to SEQ ID NO. 201 in the sequence listing sequentially;

the primer set IV includes 15 single-stranded DNA molecules, and the nucleotide sequences of the 15 single-stranded DNA molecules are shown in SEQ ID NO. 202 to SEQ ID NO. 216 in the sequence listing sequentially;

the primer set V includes 75 single-stranded DNA molecules, and the 75 single-stranded DNA molecules sequentially include the nucleotide sequences shown in SEQ ID NO. 220 to SEQ ID NO. 294 of the sequence listing from the 16th position from the 5' end to the 3' end;

the primer set VI includes 79 single-stranded DNA molecules, and the 79 single-stranded DNA molecules sequentially include the nucleotide sequences shown in SEQ ID NO. 295 to SEQ ID NO. 373 of the sequence listing from the 16th position from the 5' end to the 3' end;

the primer set VII includes 14 single-stranded DNA molecules, and the 14 single-stranded DNA molecules sequentially include the nucleotide sequences shown in SEQ ID NO. 374 to SEQ ID NO. 387 of the sequence listing from the 16th position from the 5' end to the 3' end;

the primer set VIII includes 15 single-stranded DNA molecules, and the 15 single-stranded DNA molecules sequentially include the nucleotide sequences shown in SEQ ID NO. 388 to SEQ ID NO. 402 of the sequence listing from the 16th position from the 5' end to the 3' end.

5. A method for detecting target mutation and/or methylation in a DNA sample, comprising the following steps:

(1) constructing a library;

(2) performing two rounds of nested PCR amplification to the library obtained in step (1), sequencing the product, and analyzing the occurrence of target mutation and/or methylation in the DNA sample according to the sequencing result;

in the step (2), primer combination A is used to carry out the first round of PCR amplification;

primer combination A consists of upstream primer A and downstream primer combination A;

the upstream primer A is a library amplification primer used for library amplification in step (1);

the downstream primer combination A is a combination of Y primers designed according to X target sites; X and Y are both natural numbers greater than 1, and X≤Y;

using the product of the first round of PCR as a template, carrying out the second round of PCR amplification with primer combination B;

primer combination B consists of upstream primer B, downstream primer combination B and index primer;

the upstream primer B is a library amplification primer and the 3' end is the same as that of the upstream primer A, and is used for the amplification of the product of the first round of PCR;

the index primer includes a segment A for sequencing, an index sequence for distinguishing samples, and a segment B for sequencing from the 5' end;

the primer in the downstream primer combination B has the segment B and form a nested relationship with the primer detecting the same target site in the downstream primer combination A;

wherein, the method for constructing a library in step (1) comprises the following steps sequentially:

1) taking a DNA sample and digesting it with a methylation-sensitive restriction endonuclease;

2) the DNA sample digested in step 1) is subjected to end repair and adding A treatment at the 3' end sequentially;

3) ligating the DNA sample processed in step 2) with an adapter in an adapter mixture, and obtaining a library after PCR amplification;

4) amplifying the library obtained in step 3);

the adapter mixture consists of n adapters;

each adapter is formed by an upstream primer A and a downstream primer A to form a partial double-stranded structure; the upstream primer A includes a sequencing adapter A, a random tag, an anchor sequence A and a base T sequentially from the 5' end; the downstream primer A includes an anchor sequence B and a sequencing adapter B sequentially from the 5' end; the partial double-stranded structure is formed by the reverse complementation of the anchor sequence A and the anchor sequence B;

the sequencing adapter A and sequencing adapter B are corresponding sequencing adapters selected according to different sequencing platforms;

the random tag is 8-14 bases in length;

the anchor sequence A has a length of 12-20 bp, and has ≤3 consecutive repeating bases;

the n adapters use n different anchor sequences A(s), and the four bases in each anchor sequence A are balanced, and the number of mismatched bases ≥3;

n is any natural number ≥8;

a primer pair used for amplification in step 4) consists of two single-stranded DNA molecules shown in SEQ ID NO. 25 and SEQ ID NO. 26 in the sequence listing.

6. The method according to claim 5, wherein:

the method for analyzing the target mutation in the DNA sample is: DNA molecules whose sequencing data meet the criterion A are traced back to a molecular cluster; the molecular clusters which meet the criterion B are labeled as a pair of duplex molecular clusters; for a mutation, if the following (a1) or (a2) is satisfied, the mutation is a true mutation from the original DNA sample: (a1) supported by at least one pair of duplex molecular clusters; (a2) supported by at least 4 molecular clusters; criterion A means satisfying (I), (II) and (III) at the same time; (I) the length of the DNA inserts is the same and the sequences are the same except for the mutation sites; (II) the random tag sequences are the same; (III) the anchor sequences are the same; criterion B means satisfying both IV and (V); (IV) the length of the DNA inserts is the same and the sequences are the same except for the mutation sites; (V) the anchor sequences at both ends of the molecular cluster are the same but in opposite positions;

the method for analyzing methylation in the DNA sample is: the DNA molecules whose sequencing data meet the criterion C are labeled as a cluster, and the number of clusters whose ends are the restriction sites of interest is calculated respectively, and recorded as unmethylated fragments; the number of all the clusters whose amplified fragments reach or exceed the first restriction site is calculated, and recorded as the total number of fragments; the average methylation level of the corresponding region is calculated according to the number of two fragments; the methylation level of the region=(1−the number of unmethylated fragments/the total number of fragments)×100%; criterion C means satisfying (VI), (VII), and (VIII) at the same time; (VI) the random tag sequences are the same; (VII) the anchor sequences are the same; (VIII) the length of the DNA inserts is the same and the sequences are the same except for the mutation sites.

7. A method for detecting multiple target mutations and/or methylation in a DNA sample, comprising the following steps:

(1) constructing a library according to the method described in claim 1;

(2) enriching and sequencing the target region of the library of step (1), and analyzing the occurrence of target mutation and/or methylation in the DNA sample according to the sequencing result.

8. The method according to claim 7, wherein:

the method for analyzing the target mutation in the DNA sample is: DNA molecules whose sequencing data meet the criterion A are traced back to a molecular cluster; the molecular clusters which meet the criterion B are labeled as a pair of duplex molecular clusters; for a mutation, if the following (a1) or (a2) is satisfied, the mutation is a true mutation from the original DNA sample: (a1) supported by at least one pair of duplex molecular clusters; (a2) supported by at least 4 molecular clusters; criterion A means satisfying (I), (II), and (III) at the same time; (I) the length of the DNA inserts is the same and the sequences are the same except for the mutation sites; (II) the random tag sequences are the same; (III) the anchor sequences are the same; criterion B means satisfying both (IV) and (V); (IV) the length of the DNA inserts is the same and the sequences are the same except for the mutation sites; (V) the anchor sequences at both ends of the molecular cluster are the same but in opposite positions; the method for analyzing methylation in the DNA sample is: the DNA molecules whose sequencing data meet the criterion C are labeled as a cluster, and the number of clusters whose ends are the restriction sites of interest is calculated respectively, and recorded as unmethylated fragments; the number of all the clusters whose amplified fragments reach or exceed the first restriction site is calculated, and recorded as the total number of fragments; the average methylation level of the corresponding region is calculated according to the number of two fragments; the methylation level of the region=(1−the number of unmethylated fragments/the total number of fragments)×100%; criterion C means satisfying (VI), (VII), and (VIII) at the same time; (VI) the random tag sequences are the same; (VII) the anchor sequences are the same; (VIII) the length of the DNA inserts is the same and the sequences are the same except for the mutation sites.

9. A method for distinguishing blood samples from tumor patients and blood samples from non-tumor patients, comprising the following steps:

constructing a library according to the method described in claim 1;

enriching and sequencing the target region of the library, and analyzing the occurrence of target mutation and/or methylation in the DNA sample according to the sequencing result;

distinguishing blood samples from tumor patients and blood samples from non-tumor patients according to occurrence of target mutation and/or methylation in the DNA sample.

* * * * *